US008455479B2

(12) United States Patent
Jain et al.

(10) Patent No.: US 8,455,479 B2
(45) Date of Patent: Jun. 4, 2013

(54) HETEROCYCLIC COMPOUNDS

(75) Inventors: Rajesh Jain, New Delhi (IN); Sanjay Trehan, New Delhi (IN); Jagattaran Das, New Delhi (IN); Nishan Singh, New Delhi (IN); Gurmeet Kaur Nanda, New Delhi (IN); Sitaram Kumar Magadi, New Delhi (IN); Sudhir Kumar Sharma, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 159 days.

(21) Appl. No.: 12/863,016

(22) PCT Filed: Jan. 23, 2009

(86) PCT No.: PCT/IN2009/000061
§ 371 (c)(1),
(2), (4) Date: Jul. 15, 2010

(87) PCT Pub. No.: WO2009/093269
PCT Pub. Date: Jul. 30, 2009

(65) Prior Publication Data
US 2010/0311732 A1 Dec. 9, 2010

(30) Foreign Application Priority Data

Jan. 24, 2008 (IN) .............................. 202/DEL/2008
Mar. 18, 2008 (IN) .............................. 688/DEL/2008

(51) Int. Cl.
| C07D 243/14 | (2006.01) |
| C07D 403/06 | (2006.01) |
| C07D 413/12 | (2006.01) |
| C07D 487/04 | (2006.01) |
| A61K 31/551 | (2006.01) |
| A61P 3/10   | (2006.01) |

(52) U.S. Cl.
USPC .......... 514/220; 514/221; 540/510; 540/558; 540/561; 540/562; 540/563

(58) Field of Classification Search
USPC .................. 514/220, 221; 540/510, 558, 561, 540/562, 563
See application file for complete search history.

(56) References Cited

FOREIGN PATENT DOCUMENTS

| WO | 03/004498 A    | 1/2003  |
| WO | 2004/007468 A  | 1/2004  |
| WO | 2004/032836 A  | 4/2004  |
| WO | 2004/058266 A  | 7/2004  |
| WO | 2004/103276 A  | 12/2004 |

*Primary Examiner* — Bruck Kifle
(74) *Attorney, Agent, or Firm* — Lowe Hauptman Ham & Berner, LLP

(57) ABSTRACT

The present invention relates to novel compounds of Formula I, their pharmaceutically acceptable derivatives, tautomeric forms, stereoisomers including R and S isomers, polymorphs, prodrugs, metabolites, salts or solvates thereof. The invention also relates to the processes for the synthesis of novel compounds of Formula I, their pharmaceutically acceptable derivatives, tautomeric forms, stereoisomers, polymorphs, prodrugs, metabolites, salts or solvates thereof. The present invention also provides pharmaceutical compositions comprising compounds of Formula I and methods of treating or preventing one or more conditions that may be regulated or normalized via inhibition of dipeptidyl peptidase IV (DPP-IV).

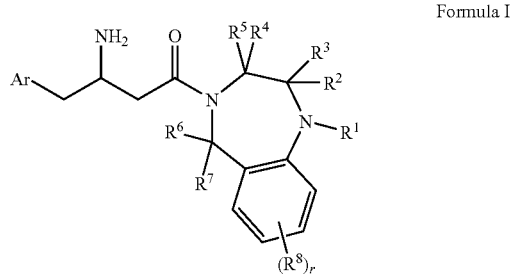

Formula I

22 Claims, No Drawings

HETEROCYCLIC COMPOUNDS

FIELD OF THE INVENTION

The present invention relates to novel compounds of Formula I, their pharmaceutically acceptable derivatives, tautomeric forms, stereoisomers including R and S isomers, polymorphs, prodrugs, metabolites, salts or solvates thereof. The invention also relates to the processes for the synthesis of novel compounds of Formula I, their pharmaceutically acceptable derivatives, tautomeric forms, stereoisomers, polymorphs, prodrugs, metabolites, salts or solvates thereof. The present invention also provides pharmaceutical compositions comprising compounds of Formula I and methods of treating or preventing one or more conditions that may be regulated or normalized via inhibition of dipeptidyl peptidase IV (DPP-IV).

BACKGROUND OF THE INVENTION

Type 2 diabetes mellitus is a multifaceted and heterogeneous metabolic syndrome, which accounts for 90-95% of all diabetes. This disorder is rapidly emerging as a global health care problem that threatens to reach pandemic levels by 2030; the number of people with diabetes worldwide is expected to rise from 171 million in 2000 to 366 million by 2030. This increase is expected to be most noticeable in developing countries, where the number of people with diabetes is expected to grow from 84 million to 228 million.

A key component of the pathophysiology of Type 2 diabetes mellitus involves an impaired pancreatic β-cell function which eventually contributes to decreased insulin secretion in response to elevated plasma glucose. An early defect in Type 2 diabetes mellitus is insulin resistance which is a state of reduced responsiveness to circulating concentrations of insulin and is often present years before the onset of hyperglycemia and the clinical diagnosis of diabetes. The β-cell compensates for increasing insulin resistance by increasing insulin secretion eventually resulting in reduced β-cell mass. Consequently, blood glucose levels stay at abnormally high levels, which in the long run leads to severe health problems in these patients including, obesity, hypertension and dyslipidemia. Uncontrolled hyperglycemia can further, lead to complications such as nephropathy, neuropathy, retinopathy and premature atherosclerosis.

Glucose-dependent insulin secretion is mainly promoted by incretins, predominantly glucose-dependent insulinotropic peptide (GIP) and glucagon-like peptide 1 (GLP-1) (7-36). These gut peptides are released from the gastrointestinal tract in response to nutrition ingestion and promote nutrient assimilation via potentiation of glucose dependent insulin secretion. Based on its physiological profile, the actions of GLP-1 (7-36) are useful for lowering blood glucose in subjects with Type 2 diabetes mellitus and thus have strong potential as chronic therapies for diabetes. Studies in which Type 2 diabetic patients have been infused with GLP-1 have demonstrated efficacy in normalizing both fasted and postprandial glycemia. However, GLP-1 (7-36) has been shown to have a short half-life in vivo (about 1.5 min) as it undergoes rapid amino terminal (His-Ala) degradation by dipeptidyl peptidase (DPP-IV). DPP-IV is a member of the s9b family of serine peptidases. Dipeptidyl peptidase IV (DPP-IV), also called adenosine deaminase binding protein (ADAbp) or CD26, is a 220-kD homodimeric, Type 2 transmembrane glycoprotein, widely expressed on the surface of a variety of epithelial, endothelial, and lymphoid cell types. DPP-IV regulates various physiological processes by cleaving Xaa-Pro dipeptides from the N-terminus of regulatory peptides, including many chemokines, neuropeptides, and peptide hormones.

GLP-1 (7-36) is degraded by DPP-IV efficiently to GLP-1 (9-36), which has been speculated to act as a physiological antagonist to GLP-1 (7-36) and totally reduces the activity of GLP-1 (7-36). The short half-life of GLP-1 in the circulation is a major obstacle to its use as a therapeutic agent. To circumvent this drawback of GLP-1, DPP-IV inhibition represents a useful strategy for prolonging GLP-1 action leading to sustained lowering of blood glucose. Clinical evidence shows that specific DPP-IV inhibitors lower blood glucose levels in Type 2 Diabetics. Advantageously, since the incretins are produced by the body only when food is consumed and their action, is glucose dependent, DPP-IV inhibition is not expected to increase the level of insulin at inappropriate times, such as between meals, which can lead to hypoglycemic events. Inhibition of DPP-IV is therefore expected to increase insulin without increasing the risk of hypoglycemia, which is a dangerous side effect associated with the use of other insulin secretagogues. The compounds shown below are the DPP-IV inhibitors which have either reached advanced stages of human clinical trials or are either awaiting regulatory approval: Merck's "Sitagliptin" with Formula A is the first DPP-IV inhibitor which has been launched under the name "Januvia", (*Expert Opinion*, 2007, 7, 557; *Current Topics in Medicinal Chemistry*, 2007, 533), Formula B represents Novartis' "Vildagliptin", Formula C represents Bristol Myers Squibb's "Saxagliptin", Formula D represents Syrrx's "Alogliptin" and Formula E represents Abbott's "ABT-279".

Formula A

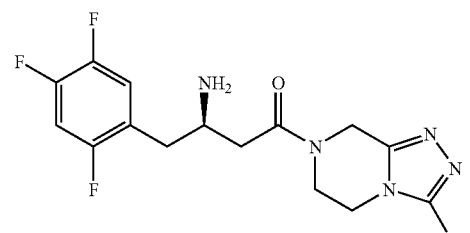

Formula B

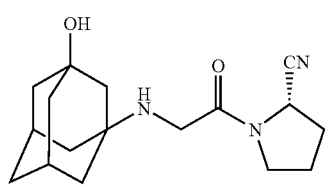

Formula C

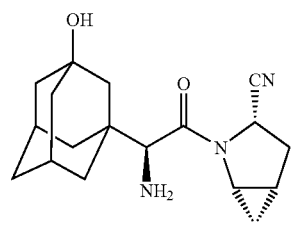

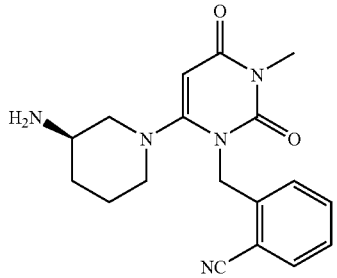

Formula D

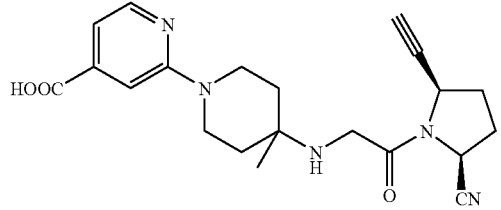

Formula E

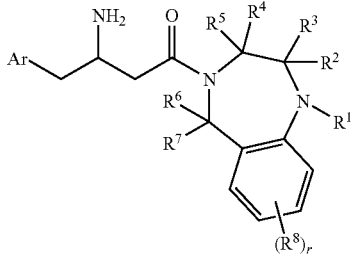

Formula I

A large number of DPP-IV inhibitors have been described in the art. For example, PCT publications WO-199819998; WO-2000034241, WO-2006127530, U.S. Pat. No. 6,110,949, U.S. Pat. No. 6,011,155, U.S. Pat. No. 7,169,806 and Japanese publication JP-2005139107 disclose cyanopyrrolidines as DPP-IV inhibitors. PCT publication WO-2004161514 discloses cyanofluoropyrrolidiries having DPP-IV inhibitory activity. US publications US 20006110949, US 20006107317 and PCT publication WO 199961431 disclose cyanothiazolidines as DPP-IV inhibitors. Aminopiperidine derivatives have been disclosed in, for example, PCT publications WO-2006058064, WO-2006039325, WO-2006058064. Others are pyrrolidine; thiazolidine, piperadine, or pyridine derivatives (see for example. WO-2006116157, WO-2005120494, WO-03084940, WO-2006062063, WO-2005042488). Still others are xanthine and purine derivatives (see for example PCT publications WO-2004018467, WO-2004018469).

β-amino acid based DPP-IV inhibitors have been disclosed in PCT publications, for example, WO-2004043940, WO-2005044195, WO-2006009886, WO-2006023750, WO-2006039325, WO-2003004498, WO-2005116029, WO-2005113510, WO-2006097175, WO-2005120494, WO-2005121131, WO-2005123685, WO-2005040095 WO-2007063928, WO-2007054577, WO-2007053819, WO-2006081151, WO-2004085378 and US patents such as U.S. Pat. No. 7,259,160, U.S. Pat. No. 7,101,871 and U.S. Pat. No. 7,208,498.

The present invention is directed to a class of β-amino acid based DPP-IV inhibitors using novel heterocycles, structurally unrelated to any DPP-IV inhibitors known so far.

Although a number of DPP-IV inhibitors have been described in the art, nonetheless, a need still exists for new DPP-IV inhibitors that have better half life, advantageous potency, stability, selectivity, less toxicity and/or better pharmacodynamics properties. There is a need for DPP-IV inhibitors that can increase the amount of circulating GLP-1 over prolonged period of time, thus leading to better control of diabetes related complications. In this regard, a novel class of DPP-IV inhibitors is provided herein.

SUMMARY OF THE INVENTION

The present invention relates to the compounds of Formula I, their pharmaceutically acceptable derivatives, tautomeric forms, stereoisomers including R and S isomers, polymorphs, prodrugs, metabolites, salts or solvates thereof, wherein:

Ar represents aryl which may be phenyl; which may further be unsubstituted or may be optionally substituted at any available position by one or more substituents selected from but not limited to halogen, CN, hydroxyl, $NH_2$, $C_{1-12}$ alkyl or $C_{1-12}$ alkoxy;

$R^1$ is selected from the group consisting of but not limited to $(CH_2)_nCONR^aR^b$, $(CH_2)_nCOOR^a$, $(CH_2)_nNR^aR^b$, $(CH_2)_nNR^aCOR^b$, $(CH_2)_nC(=L)R^a$ (wherein L is O or S), $(CH_2)_nOR^a$ (wherein each methylene group may be substituted by one or more halogen atoms), $-(CO)R^a$, $-(CO)NR^aR^b$, hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, each of which may be optionally substituted at any available position by one or more substituents selected from but not limited to hydrogen, halogen, CN, $C_{1-12}$ alkyl, $C_{1-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, oxo, $-OR^a$, $SR^a$, $-NO_2$, $-NR^aR^b$, $N(R^a)(CO)R^b$, $N(R^a)(CO)OR^b$, $N(R^a)(CO)NR^aR^b$, $-(CO)R^a$, $-(CO)NR^aR^b$, $-O(CO)R^a$, $-O(CO)NR^aR^b$, $-COOR^a$, $C_{3-8}$ cycloalkyl, $S(O)_mR^a$, $SO_2NR^aR^b$; cycloalkyl which may be optionally substituted at any available position by one or more substituents independently selected from $R^c$ or $R^{c'}$; aryl which may be optionally substituted at any available position by one or more substituents independently selected from $R^c$ or $R^{c'}$; heteroaryl which may be optionally substituted at any available position by one or more substituents independently selected from $R^c$ or $R^{c'}$; or heterocyclyl which may be optionally substituted at any available position by one or more substituents independently selected from $R^c$ or $R^{c'}$;

$R^2$ and $R^3$ together represents a single oxygen or sulphur atom which is linked to the diazepine ring by a double bond; or $R^1$ and $R^2$ together forms a double bond in the diazepine ring and $R^3$ represents the group $-NR^aR^b$; or $R^1$ and $R^3$ together with the nitrogen atom to which $R^1$ is attached forms a heterocyclic or heteroaryl ring which may additionally contain from one to three heteroatoms independently selected from O, S and N; the ring formed may optionally be substituted, with one or more substituents selected from $R^c$ or $R^{c'}$ and $R^2$ represent hydrogen or a double bond;

$R^4$ and $R^5$ are independently selected from the group consisting of hydrogen, halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, $-OR^a$, $-SR^a$, $-NO_2$, $-NR^aR^b$, $N(R^a)(CO)R^b$, $N(R^a)(CO)OR^b$, $N(R^a)(CO)NR^aR^b$, $-(CO)R^a$, $-(CO)NR^aR^b$, $-O(CO)R^a$, —O(CO)NR$^a$R$^b$, —COOR$^a$, C$_{3-8}$ cycloalkyl, S(O)$_m$R$^a$, SO$_2$NR$^a$R$^b$; cycloalkyl which may be optionally substituted at any available position by one or more substituents independently selected from R$^c$ or R$^{c'}$; aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

R$^6$ and R$^7$ are independently selected from the group consisting of hydrogen, halogen, CN, C$_{1-12}$ alkyl, C$_{2-12}$ alkenyl, C$_{2-12}$ alkynyl, C$_{1-12}$ alkoxy, C$_{1-12}$ haloalkyl, C$_{1-12}$ haloalkoxy, C$_{2-12}$ haloalkenyl, C$_2$-C$_{12}$ haloalkynyl, C$_{1-12}$ alkylcarbonyl, C$_{1-12}$ alkoxycarbonyl, —OR$^a$, —SR$^a$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, C$_{3-8}$ cycloalkyl, S(O)$_m$R$^a$, SO$_2$NR$^a$R$^b$; cycloalkyl which may be optionally substituted at any available position by one or more substituents independently selected from R$^c$ or R$^{c'}$; aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

R$^8$ is independently selected from hydrogen, halogen, CN, C$_{1-12}$ alkyl, C$_{1-12}$ haloalkyl, C$_{1-12}$ alkoxy, C$_{1-12}$ haloalkoxy, C$_{2-12}$ haloalkenyl C$_{1-12}$ alkylcarbonyl, C$_{1-12}$ alkoxycarbonyl, —OR$^a$, —SR$^a$, —CF$_3$, —OCF$_3$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, C$_{3-6}$ cycloalkyl, S(O)$_m$R$^a$, SO$_2$NR$^a$R$^b$; cycloalkyl which may be optionally substituted at any available position by one or more substituents independently selected from R$^c$ or R$^{c'}$; heteroaryl which may optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

R$^a$ and R$^b$ are independently selected from hydrogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-8}$ cycloalkyl, heterocyclyl, aryl, heteroaryl, (CH$_2$)$_n$-cycloalkyl, (CH$_2$)$_n$-heterocyclyl, (CH$_2$)$_n$-aryl, (CH$_2$)$_n$-heteroaryl; each of which may be optionally substituted with halogen, hydroxyl, C$_{1-12}$ alkyl, C$_{2-12}$ alkenyl, C$_{2-12}$ alkynyl, C$_{1-12}$ alkoxy, C$_{1-12}$ alkylcarbonyl, C$_{1-12}$ alkoxycarbonyl, C$_{3-8}$ cycloalkyl, C$_{1-12}$ haloalkyl, C$_{1-12}$ haloalkoxy, C$_{2-12}$ haloalkenyl, aryl, heterocyclyl, heteroaryl, (CH$_2$)$_n$-aryl, (CH$_2$)$_n$-heterocyclyl, (CH$_2$)$_n$-heteroaryl, (CH$_2$)$_n$-cycloalkyl, oxo, —CN, —OR$^9$, —NO$_2$, —NR$^9$R$^{10}$, N(R$^9$)(CO)R$^{10}$, N(R$^9$)(CO)OR$^{10}$, N(R$^9$)(CO)NR$^9$R$^{10}$, —C(=L)R$^9$ (wherein L is O or S); —(CO)NR$^9$R$^{10}$, —O(CO)R$^9$, —O(CO)NR$^9$R$^{10}$, —COOR$^9$, —SR$^9$, S(O)$_m$R$^9$, SO$_2$NR$^9$R$^{10}$; SO$_3$H, NHSO$_2$R$^9$, P(O)R$^9$R$^{10}$; or R$^a$ and R$^b$ may be joined together along with the nitrogen atom to which they are attached to form a heterocyclic or heteroaryl ring which may additionally contain from one to three heteroatoms independently selected from O, S and N, the ring formed may optionally be substituted with one or more substituents selected from hydrogen, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-8}$ cycloalkyl, heterocyclyl, aryl, heteroaryl, (C$_2$)$_n$—cycloalkyl, (CH$_2$)$_n$-heterocyclyl, (CH$_2$)$_n$-aryl, (CH$_2$)$_n$-heteroaryl, C$_{1-12}$ alkylcarbonyl, C$_{1-12}$ alkoxycarbonyl, oxo, CN, —OR$^9$, —CF$_3$, —OCF$_3$CH$_2$CF$_3$, CF$_2$CF$_3$, —NO$_2$, —NR$^9$R$^{10}$), N(R$^9$)(CO)R$^{10}$, N(R$^9$)(CO)OR$^{10}$, N(R$^9$)(CO)NR$^9$R$^{10}$, —C(=L)R$^9$ (wherein L is O or S), —(CO)NR$^9$R$^{10}$, —O(CO)C$_1$-C$_{12}$ alkyl, —O(CO)NR$^9$R$^{10}$, —COOR$^9$, —SR$^9$, S(O)$_m$R$^9$, SO$_2$NR$^9$R$^{10}$; SO$_3$H, —NHSO$_2$R$^9$, —P(O)R$^9$R$^{10}$; the ring thus formed may further be fused with 3 to 7 membered unsaturated or saturated ring, which may contain from one to three heteroatoms independently selected from O, S or N, the fused ring may optionally be substituted with one or more substituents R$^c$ or R$^{c'}$;

R$^c$ or R$^{c'}$ is independently selected from the group consisting of but not limited to hydrogen, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{1-12}$ alkoxy, C$_{1-12}$ haloalkoxy, C$_{3-8}$ cycloalkyl, heterocyclyl, aryl, heteroaryl, (CH$_2$)$_n$-cycloalkyl, (CH$_2$)$_n$-heterocyclyl; (CH$_2$)-aryl, (CH$_2$)$_n$-heteroaryl, C$_{1-12}$ alkylcarbonyl, C$_{1-12}$ alkoxycarbonyl, CN, —OR$^9$, —OCF$_3$, —NO$_2$, =NOR$^{10}$, —NR$^9$R$^{10}$, N(R$^9$)(CO)R$^{10}$, N(R$^9$)(CO)OR$^{10}$, N(R$^9$)(CO)NR$^9$R$^{10}$, —C(=L)R$^9$ (wherein L is O or S), —(CO)NR$^9$R$^{10}$, —O(CO)R$^9$, —O(CO)NR$^9$R$^{10}$, —COOR$^9$, —SR$^9$, S(O)$_m$R$^9$, SO$_2$NR$^9$R$^{10}$; SO$_3$H, NHSO$_2$R$^9$, P(O)R$^9$R$^{10}$;

R$^9$ and R$^{10}$ are independently selected from hydrogen, C$_{1-12}$ alkyl, C$_{2-12}$ alkenyl, C$_{2-12}$ alkynyl, C$_{1-12}$ haloalkyl, C$_{2-12}$ haloalkenyl, C$_{3-8}$ cycloalkyl, heterocyclyl, aryl, heteroaryl, (CH$_2$)$_n$-cycloalkyl, (CH$_2$)$_n$-heterocyclyl, (CH$_2$)$_n$-aryl, (CH$_2$)$_n$-heteroaryl, each of which may be optionally substituted with halogen, hydroxyl or C$_{1-6}$ alkoxy, or R$^9$ and R$^{10}$ may be joined together to form a heterocyclic or heteroaryl ring which may contain from one to three heteroatoms independently selected from O, S and N, which may optionally be substituted with one or more substituents independently selected from R$^c$ or R$^{c'}$;

m is 1 or 2;
n is 1, 2, 3 or 4;
r is 1, 2, 3 or 4.

Another aspect of the invention provides the processes for the preparation of the novel compounds of Formula I, their pharmaceutically acceptable derivatives, tautomeric forms, stereoisomers including R and S isomers; polymorphs, prodrugs, metabolites, salts or solvates thereof.

A further aspect of the present invention provides pharmaceutical compositions, containing compounds of Formula I, their pharmaceutically acceptable derivatives, tautomeric forms, stereoisomers including R and S isomers, polymorphs; prodrugs, metabolites, salts or solvates thereof in combination with one or more pharmaceutically acceptable carrier(s).

Another aspect of the present invention is the use of the compounds of Formula I for the prophylaxis, amelioration and/or treatment of one or more condition(s)/disease(s)/disorder(s) that may be regulated or normalized via inhibition of DPP-IV.

Yet another aspect of the invention is to provide methods of using the compounds of Formula I of the present invention or compositions comprising the compounds of Formula I for the prophylaxis, amelioration and/or treatment of disease(s)/disorder(s) mediated by DPP-IV which comprises administering to a subject in need thereof the compounds of Formula I or compositions comprising a pharmaceutically effective amount of the compounds of Formula I.

A further aspect of the present invention is the use of a compound of Formula I for the manufacture of a medicament for the prophylaxis, amelioration and/or treatment of one or more condition(s)/disease(s)/disorder(s) mediated by DPP-IV in a subject in need thereof.

The present invention also encompasses prodrugs and active, metabolites of the compounds of the Formula I.

Other aspects of the invention will be set forth in the description which follows, and in part will be apparent from the description, or may be learnt by the practice of the invention.

DETAILED DESCRIPTION OF THE INVENTION

The present invention relates, to the compounds of Formula I, their pharmaceutically acceptable derivatives, tautomeric forms, stereoisomers including R and S isomers, polymorphs, prodrugs, metabolites, salts or solvates thereof, wherein:

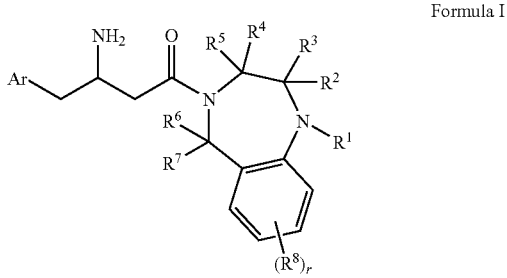

Formula I

Ar represents aryl which may be phenyl; which may further be unsubstituted or may be optionally substituted at any available position by one or more substituents selected from but not limited to halogen, CN, hydroxyl, $NH_2$, $C_{1-12}$ alkyl or $C_{1-12}$ alkoxy;

$R^1$ is selected from the group consisting of but not limited to $(CH_2)_nCONR^aR^b$, $(CH_2)_nCOOR^a$, $(CH_2)_nNR^aR^b$, $(CH_2)NR^aCOR^b$, $(CH_2)_nC(=L)R^a$ (wherein L is; O or S), $(CH_2)_nOR^a$ (wherein each methylene group may be substituted by one or more halogen atoms), $—(CO)R^a$, $—(CO)NR^aR^b$, hydrogen, $C_{1-12}$ alkyl, $C_{2-12}$ alkenyl, $C_{1-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(C_2)_n$-heteroaryl, each of which may be optionally substituted at any available position by one or more substituents selected from but not limited to hydrogen, halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, oxo, $—OR^a$, $—SR^a$, $—NO_2$, $—NR^aR^b$, $N(R^a)(CO)R^b$, $N(R^a)(CO)OR^b$, $N(R^a)(CO)NR^aR^b$, $—(CO)R^a$, $—(CO)NR^aR^b$, $—O(CO)R^a$, $—O(CO)NR^aR^b$, $—COOR^a$, $C_{3-8}$ cycloalkyl, $S(O)_mR^a$, $SO_2NR^aR^b$ cycloalkyl which may be optionally substituted at any available position by one or more substituents independently selected from $R^c$ or $R^{c'}$; aryl which may be optionally substituted at any available position by one or more substituents independently selected from $R^c$ or $R^{c'}$; heteroaryl which may be optionally substituted at any available position by one or more substituents independently selected from $R^c$ or $R^{c'}$; or heterocyclyl which may be optionally substituted at any available position by one or more substituents independently selected from $R^c$ or $R^{c'}$;

$R^2$ and $R^3$ together represents a single oxygen or sulphur atom which is linked to the diazepine ring by a double bond; or $R^1$ and $R^2$ together forms a double bond in the diazepine ring and $R^3$ represents the group $—NR^aR^b$; or $R^1$ and $R^3$ together with the nitrogen atom to which $R^1$ is attached forms a heterocyclic or heteroaryl ring which may additionally contain from one to three heteroatoms independently selected from O, S and N; the ring formed may optionally be substituted with one or more substituents selected from $R^c$ or $R^{c'}$ and $R^2$ represent hydrogen or a double bond;

$R^4$ and $R^5$ are independently selected from the group consisting of hydrogen, halogen, CN, $C_{1-12}$ alkyl, $C_{2-12}$ alkenyl, $C_{2-12}$ alkynyl, $Cl_{1-12}$ alkoxy, $C_{1-12}$ haloalkyl, $Cl_{1-12}$ haloalkoxy, $C_{2-12}$ haloalkenyl, $C_{2-12}$ haloalkynyl, $Cl_{1-12}$ alkylcarbonyl, $C_{1-12}$ alkoxycarbonyl, $—OR^a$, $—SR^a$, $NO_2$, $—NR^aR^b$, $N(R^a)(CO)R^b$, $N(R^a)(C)OR^b$, $N(R^a)(CO)NR^aR^b$, $—(CO)R^a$, $—(CO)NR^aR^b$, $—O(CO)R^a$, $—O(CO)NR^aR^b$, $—COOR^a$, $C_{3-8}$ cycloalkyl, $S(O)_mR^a$; $SO_2NR^aR^b$; cycloalkyl which may be optionally substituted at any available position by one or more substituents independently selected from $R^c$ or $R^{c'}$; aryl which may be optionally substituted at any available position by one or more substituents independently selected, from $R^c$ or $R^{c'}$; heteroaryl which may be optionally substituted at any available position by one or more substituents independently selected from $R^c$ or $R^{c'}$; or heterocyclyl which may be optionally substituted at any available position by one or more substituents independently selected from $R^c$ or $R^{c'}$;

$R^6$ and $R^7$ are independently selected from the group consisting of hydrogen, halogen CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, $—OR^a$, $—SR^a$, $—NO_2$, $—NR^aR^b$, $N(R^a)(CO)R^b$, $N(R^a)(CO)OR^b$, $N(R^a)(CO)NR^aR^b$, $—(CO)R^a$, $—(CO)NR^aR^b$, $—O(CO)R^a$, $—O(CO)NR^aR^b$, $—COOR^a$, cycloalkyl, $S(O)_mR^a$, $SO_2NR^aR^b$; cycloalkyl which may be optionally substituted at any available position by one or more substituents independently selected from $R^c$ or $R^{c'}$; aryl which may be optionally substituted at any available position by one or more substituents independently selected from $R^c$ or $R^{c'}$; heteroaryl which may be optionally substituted at any available position by one or more substituents independently selected from $R^C$ or $R^{c'}$; or heterocyclyl which may be optionally substituted at any available position by one or more substituents independently selected from $R^c$ or $R^{c'}$;

$R^8$ is independently selected from hydrogen, halogen, CN, $C_{1-12}$ alkyl, $C_{1-12}$ haloalkyl, $C_{1-12}$ alkoxy, $C_{1-12}$ haloalkoxy, $C_{2-12}$ haloalkenyl, $C_{1-12}$ alkylcarbonyl, $C_{1-12}$ alkoxycarbonyl, $—OR^a$; $—SR^a$, $—CF_3$, $—OCF_3$, $—NO_2$, $—NR^aR^b$, $—N(R^a)(CO)R^b$, $N(R^a)(CO)OR^b$, $N(R^a)(CO)NR^aR^b$, $—(CO)R^a$, $—(CO)NR^aR^b$, $—O(CO)R^a$, $—O(CO)NR^aR^b$, $—COOR^a$, $C_{3-6}$ cycloalkyl, $S(O)_mR^a$, $SO_2NR^aR^b$; cycloalkyl which may be optionally substituted at any available position by one or more substituents independently selected from $R^c$ or $R^{c'}$; aryl which may be optionally substituted at any available position by one or more substituents independently selected from $R^c$ or $R^{c'}$; heteroaryl which may be optionally substituted at any available position by one or more substituents independently selected from $R^c$ or $R^{c'}$; or heterocyclyl which may be optionally substituted at any available position by one or more substituents independently selected from $R^c$ or $R^{c'}$;

$R^a$ and $R^b$ are independently selected from, hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl; heterocyclyl, aryl, heteroaryl, $(CH_2)_n$-cycloalkyl, $(CH_2)_n$-heterocyclyl, $(CH_2)_n$-aryl, $(CH_2)_n$-heteroaryl; each of which may be optionally substituted with halogen, hydroxyl, $C_{1-12}$ alkyl, $C_{2-12}$ alkenyl, $C_{2-12}$ alkynyl, $C_{1-12}$ alkoxy, $C_{1-12}$ alkylcarbonyl, $C_{1-12}$ alkoxycarbonyl, $C_{3-8}$ cycloalkyl, $C_{1-12}$ haloalkyl, $C_{1-12}$ haloalkoxy, $C_{2-12}$ haloalkenyl, aryl, heterocyclyl, heteroaryl, $(CH_2)_n$-aryl, $(CH_2)_n$-heterocyclyl, $(CH_2)_n$-heteroaryl, $(CH_2)_n$-cycloalkyl, oxo, —CN, —$OR^9$, $NO_2$, $NR^9R^{10}$, $N(R^9)(CO)R^{10}$, $N(R^9)(CO)OR^{10}$; $N(R^9)(CO)NR^9R^{10}$, —$C(=L)R^9$ (wherein L is O or S); —$(CO)NR^9R^{10}$, —$O(CO)R^9$, —$O(CO)NR^9R^{10}$, —$COOR^9$, —$SR^9$, $S(O)_mR^9$, $SO_2NR^9R^{10}$; $SO_3H$, $NHSO_2R^9$, $P(O)R^9R^{10}$; or $R^a$ and $R^b$ may be joined together along with the nitrogen atom to which they are attached to form a heterocyclic or heteroaryl ring which may additionally contain from one to three heteroatoms independently selected from O, S and N, the ring formed may optionally be substituted with one or more substituents selected from hydrogen, halogen, $Cl_{1-12}$ alkyl, $C_{2-12}$ alkenyl, $C_{2-12}$ alkynyl, $Cl_{1-12}$ haloalkyl, $C_{2-12}$ haloalkenyl, $C_{2-12}$ haloalkynyl, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, $C_{1-12}$ alkylcarbonyl, $C_{1-12}$ alkoxycarbonyl, oxo, CN, —$OR^9$, —$CF_3$, —$OCF_3CH_2CF_3$, $CF_2CF_3$, —$NO_2$, —$NR^9R^{10}$, $N(R^9)(CO)R^{10}$, $N(R^9)(CO)OR^{10}$, $N(R^9)(CO)NR^9R^{10}$, —$C(=L)R^9$ (wherein L is O or S), —$(CO)NR^9R^{10}$, —$O(CO)C_1-C_{12}$ alkyl, —$O(CO)NR^9R^{10}$, —$COOR^9$, —$SR^9$, $S(O)_mR^9$, $SO_2NR^9R^{10}$; $SO_3H$, $NHSO_2R^9$, $P(O)R^9R^{10}$; the ring thus formed may further be fused with 3 to 7 membered unsaturated or saturated ring, which may contain from one to three heteroatoms independently selected from O, S or N, the fused ring may optionally be substituted with one or more substituents $R^c$ or $R^{c'}$;

$R^c$ or $R^{c'}$ is independently selected from the group consisting of but not limited to hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{1-12}$ alkoxy, $C_{1-12}$ haloalkoxy, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, $C_{1-12}$ alkylcarbonyl, $C_{1-12}$ alkoxycarbonyl, CN, —$OR^9$, —$OCF_3$, —$NO_2$, =$NOR^{10}$, —$NR^9R^{10}$, $N(R^9)(CO)R^{10}$, $N(R^9)(CO)OR^{10}$, $N(R^9)(CO)NR^9R^{10}$, —$C(=L)R^9$ (wherein L is O or S), —$(CO)NR^9R^{10}$, —$O(CO)R^9$, —$O(CO)NR^9R^{10}$, —$COOR^9$, —$SR^9$, $S(O)_mR^9$, $SO_2NR^9R^{10}$; $SO_3H$, $NHSO_2R^9$, $P(O)R^9R^{10}$;

$R^9$ and $R^{10}$ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, each of which may be optionally substituted with halogen, hydroxyl or $C_{1-6}$ alkoxy, or $R^9$ and $R^{10}$ may be joined together to form a heterocyclic or heteroaryl ring which may contain from one to three heteroatoms independently selected from O, S and N, which may optionally be substituted with one or more substituents independently selected from $R^c$ or $R^{c'}$;

m is 1 or 2;

n is 1, 2, 3 or 4;

r is 1, 2, 3 or 4.

One embodiment of the present invention provides compounds of Formula Ia, wherein

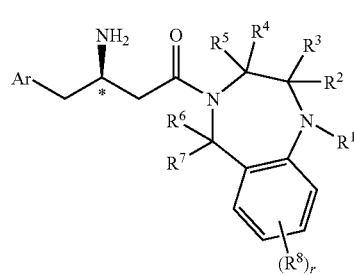

Formula Ia r, Ar, $R^1$, $R^2$, $R^3$, $R^4$, $R^5$, $R^6$, $R^7$ and $R^8$ are as defined herein; their pharmaceutically acceptable derivatives, tautomeric forms, stereoisomers, polymorphs, prodrugs, metabolites, salts or solvates thereof.

Another embodiment of the present invention provides compounds of Formula Ib, wherein

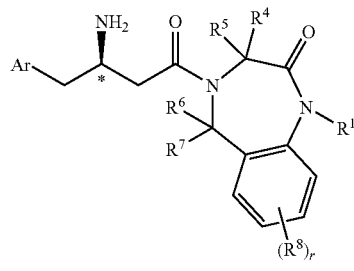

Formula Ib $R^2$ and $R^3$ together represent a single oxygen which is linked to the diazepine ring by a double bond; r, Ar, $R^1$, $R^4$, $R^5$, $R^6$, $R^7$ and $R^8$ are defined herein; their pharmaceutically acceptable derivatives, tautomeric forms, stereoisomers, polymorphs, prodrugs, metabolites, salts or solvates thereof.

Another embodiment of the present invention provides compounds of Formula Ic, wherein

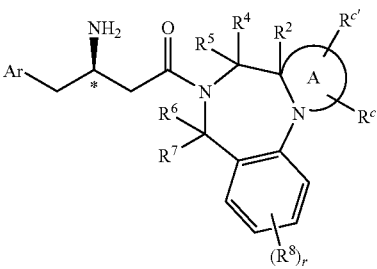

Formula Ic $R^1$ and $R^3$ together with the nitrogen atom to which $R^1$ is attached, form a heterocyclic or heteroaryl ring A, which is optionally substituted at any available position by one or more substituents independently selected from $R^c$ or $R^{C'}$; $R^2$ either represents hydrogen or a double bond; r, Ar, $R^4$, $R^5$, $R^6$, $R^7$, $R^8$, $R^c$ and $R^{c'}$ are as defined herein; their pharmaceutically acceptable derivatives, tautomeric forms, stereoisomers, polymorphs, prodrugs, metabolites, salts or solvates thereof.

Another embodiment of the present invention provides compounds of Formula Id, wherein

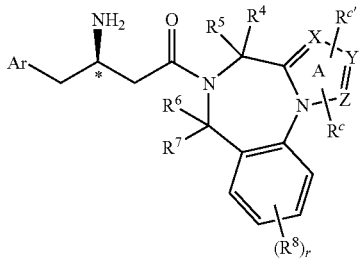

Formula Id $R^1$ and $R^3$ together with the nitrogen atom to which $R^1$ is attached, form a 5-membered heterocyclyl or heteroaryl ring A wherein X, Y and Z are independently selected from the group consisting of N and —CH, the ring A is optionally substituted at any available position by one or more substituents independently selected from $R^c$ or $R^{c'}$; $R^2$ represents a double bond; r, Ar, $R^4$, $R^5$, $R^6$, $R^7$, $R^8$, $R^c$ and $R^{c'}$ are as defined herein; their pharmaceutically acceptable derivatives, tautomeric forms, stereoisomers, polymorphs, prodrugs, metabolites, salts or solvates thereof.

Another embodiment of the present invention provides compounds of Formula Ie, wherein

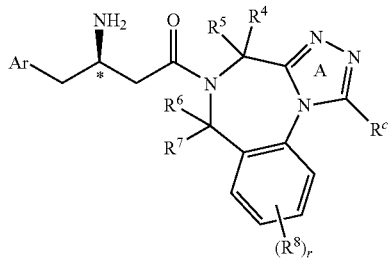

Formula Ie ring A is optionally substituted by $R^c$; $R^2$ represents a double bond; r, Ar, $R^4$, $R^5$, $R^6$, $R^7$, $R^8$ and $R^c$ are defined herein; their pharmaceutically acceptable derivatives, tautomeric forms, stereoisomers, polymorphs, prodrugs, metabolites, salts or solvates thereof.

Still another embodiment of the present invention provides compounds of Formula If, wherein

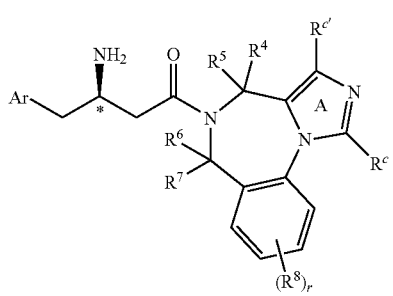

Formula If ring A is optionally substituted by one or more substituents independently selected from $R^c$ or $R^{c'}$; $R^2$ represents a double bond; r, Ar, $R^4$, $R^5$, $R^6$, $R^7$, $R^8$, $R^c$ and $R^{c'}$ are defined herein; their pharmaceutically acceptable derivatives; tautomeric forms, stereoisomers, polymorphs, prodrugs, metabolites, salts or solvates thereof.

Another embodiment of the present invention provides compounds of Formula Ig, wherein

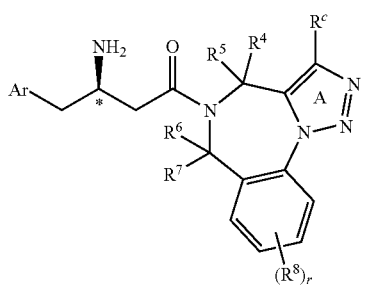

Formula Ig ring A is optionally substituted by $R^c$; $R^2$ represents a double bond; r, Ar, $R^4$, $R^5$, $R^6$, $R^7$, $R^8$ and $R^c$ are defined herein; their pharmaceutically acceptable derivatives, tautomeric forms, stereoisomers, polymorphs, prodrugs, metabolites, salts or solvates thereof.

Another embodiment of the present invention provides compounds of Formula Ih, wherein

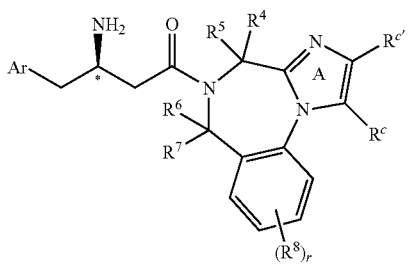

Formula Ih ring A is optionally substituted by one or more substituents independently selected from $R^c$ or $R^{c'}$; $R^2$ represents a double bond; r, Ar, $R^4$, $R^5$, $R^6$, $R^7$; $R^8$, $R^c$ and $R^{c'}$ are defined herein; their pharmaceutically acceptable derivatives, tautomeric forms, stereoisomers; polymorphs, prodrugs, metabolites, salts or solvates thereof.

In another embodiment of the compounds of the present invention, Ar is phenyl which is unsubstituted or substituted with 1-5 substituents independently selected from the group consisting of fluoro, bromo and $C_{1-12}$ alkyl.

In a further embodiment of the compounds of the present invention, it is preferred that Ar is selected from the group consisting of 2,4,5-trifluorophenyl, 2-fluorophenyl, 3,4-difluorophenyl and 2,5-difluorophenyl.

In another embodiment of the compounds of the present invention, it is preferred that $R^8$ is selected from the group consisting of hydrogen, halogen, $C_{1-12}$ alkyl, $C_{1-12}$ alkoxy and $C_{1-12}$ alkoxycarbonyl.

In a further embodiment of the compounds of the present invention, it is more preferred that $R^8$ is selected from the group consisting of hydrogen, fluoro, chloro and methoxy.

In a further embodiment of the compounds of the present invention, it is still more preferred that $R^8$ is independently selected from hydrogen and fluoro.

In another embodiment of the compounds of the present invention, $R^1$ is selected from the group consisting of hydrogen, $(CH_2)_n$, $CONR^aR^b$, $—(CO)NR^aR^b$, $—(CO)R^a$, $(CH_2)_n$, $COOR^a$, $(CH_2)_nNR^aR^b$, $(CH_2)_n$, $NCOR^a$, $(CH_2)_nC(=L)R^a$ (wherein L is O or S), $C_{1-12}$ alkyl, $C_{2-12}$ alkenyl, $C_{1-12}$ haloalkyl, $C_{1-12}$ haloalkoxy, $C_{2-12}$ haloalkenyl, $C_{2-12}$ alkenyl, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, each of which is unsubstituted or substituted, at any available position, with one or more substituents independently selected from the group consisting of halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{1-12}$ haloalkenyl, $C_{2-12}$ haloalkynyl, $C_{1-12}$ alkylcarbonyl, $C_{1-12}$ alkoxycarbonyl, oxo, $—OR^a$, $—SR^a$, $—NO_2$, $—NR^aR^b$, $—N(R^a)(CO)R^b$, $—N(R^a)(CO)OR^b$, $—N(R^a)(CO)NR^aR^b$, $—(CO)R^a$, $—(CO)NR^aR^b$, $—O(CO)R^a$, $—O(CO)NR^aR^b$, $—COOR^a$, $C_{3-8}$ cycloalkyl, heteroaryl, heterocyclyl.

In a further embodiment of the compounds of the present invention, it is preferred that $R^1$ is selected from the group consisting of: hydrogen, $C_{1-12}$ alkyl, $C_{2-12}$ alkenyl, $C_{2-12}$ alkynyl, $C_{1-12}$ haloalkyl, $C_{1-12}$ haloalkoxy, $C_{2-12}$ haloalkenyl,

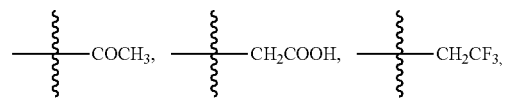

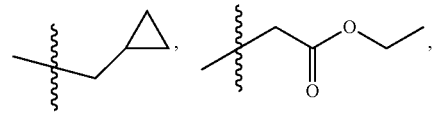

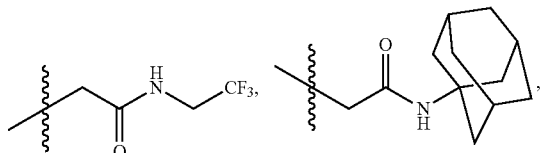

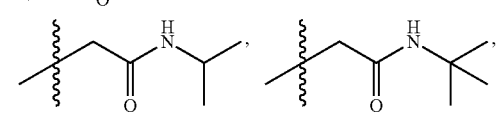

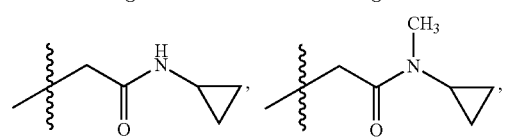

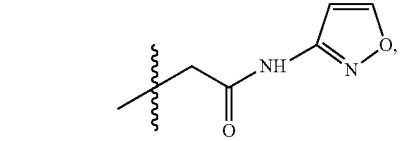

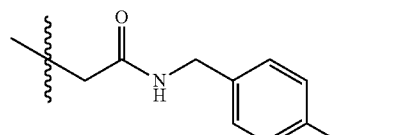

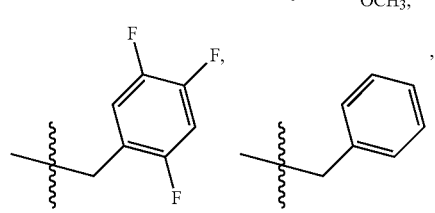

-continued

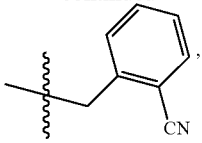

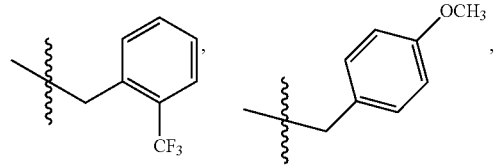

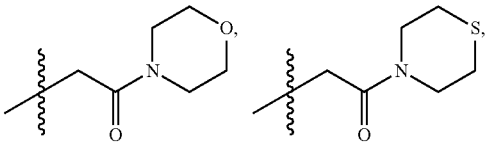

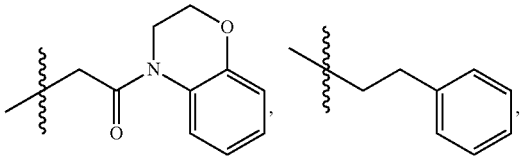

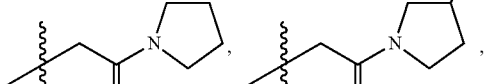

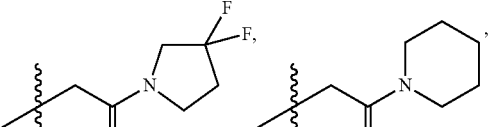

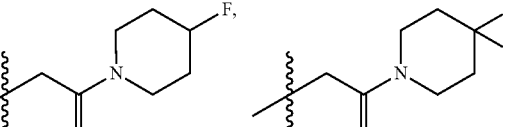

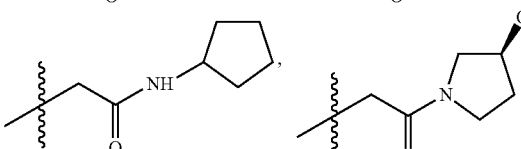

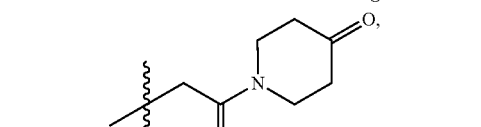

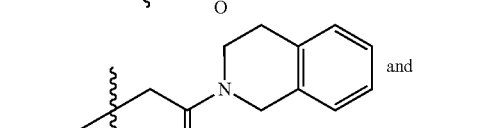

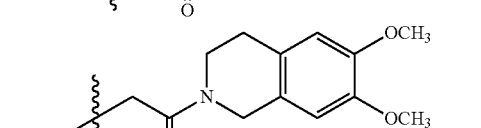

and

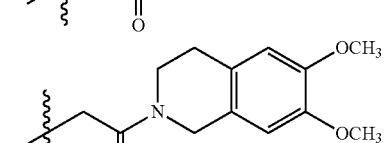

Another embodiment of the present invention provides compounds of the Formula Ic, Formula Id, Formula Ie, Formula If, Formula Ig and Formula Ih wherein the ring A is substituted with one or more $R^c$ and $R^{c'}$ independently selected from the group consisting of halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{1-12}$ alkoxy, $C_{1-12}$ haloalkoxy, $C_{3-8}$ cycloalkyl, heterocyclyl, aryl, heteroaryl, $(CH_2)_n$-cycloalkyl, $(CH_2)_n$-heterocyclyl, $(CH_2)_n$-aryl, $(CH_2)_n$-heteroaryl, $C_{1-12}$ alkylcarbonyl, $C_{1-12}$ alkoxycarbonyl, —CN, —$OR^9$, —$OCF_3$, —$NO_2$, =$NOR^{10}$, —$NR^9R^{10}$, —$N(R^9)(CO)R^{10}$, —$N(R^9)(CO)OR^{10}$, —$N(R^9)(CO)NR^9R^{10}$, —C(=L)$R^9$ (wherein L is O or S), —(CO)$NR^9R^{10}$, —O(CO)$R^9$, —O(CO)$NR^9R^{10}$, —$COOR^9$, —$SR^9$, —$S(O)_mR^9$, —$SO_2NR^9R^{10}$; —$SO_3H$, —$NHSO_2R^9$ and P(O)$R^9R^{10}$, where $R^9$ and $R^{10}$ are as defined herein;

In a further embodiment of the compounds of the Formula Ic, Formula Id, Formula Ie, Formula If, Formula Ig and Formula Ih, it is preferred that ring A is substituted with one or more $R^c$ and $R^{c'}$ independently selected from the group consisting of hydrogen, $C_{1-12}$ alkyl, $C_{2-12}$ alkenyl, $C_{2-12}$ alkynyl, $C_{3-8}$ cycloalkyl, phenyl, —$CH_2F$, —$CHF_2$, —$CF_3$, —COOH, —$CONH_2$, —$CH_2$—$OCH_3$, $COOC_{1-6}$ alkyl,

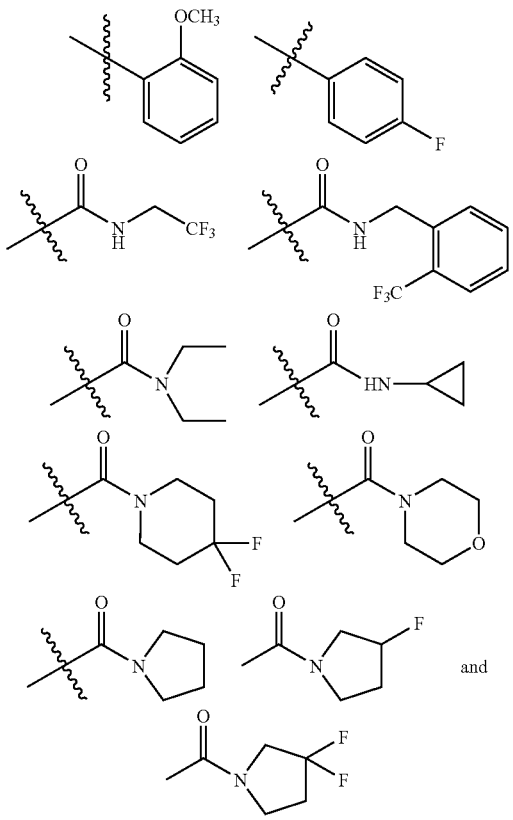

In an embodiment of the compounds of the present invention, $R^4$ and $R^5$ are independently selected from the group consisting of hydrogen, halogen, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, —$NO_2$, cycloalkyl, aryl, heteroaryl or heterocyclyl, each, of which may be unsubstituted or substituted, at any available position, with one or more substituents independently selected from $R^c$ or $R^{c'}$.

In a further embodiment of the compounds of the present invention, it is preferred that $R^4$ and $R^5$ are both hydrogen.

In an embodiment of the compounds of the present invention, $R^6$ and $R^7$ are independently selected from the group consisting of hydrogen, $C_{1-12}$ alkyl and $C_{1-12}$ alkoxy, which are unsubstituted or substituted, at any available position, with one or more substituents, selected from the group consisting of halogen, hydroxyl, $C_{1-12}$ alkoxy and aryl.

In a further embodiment of the compounds of the present invention, it is preferred that $R^6$ and $R^7$ are both hydrogen.

Relative to the above description of the compounds of the present invention, the following definitions apply.

Unless specified otherwise, the terms "alkyl", "alkenyl", and "alkynyl" may be straight or branched with 1 to 12 carbon atoms. These groups may further be substituted with one or more substituents selected from but not limited to, for example, halogen, hydroxyl, oxo, carboxyl, carboxyalkyl, azido, alkenyl, alkynyl, alkoxy, cycloalkyl, cycloalkynyl, acyl acyloxy, aryl, heterocyclyl and heteroaryl.

The term "cycloalkyl" refers to cyclic alkyl groups constituting of 3 to 20 carbon atoms having a single cyclic ring or multiple condensed rings, for example, fused or spiro systems which may optionally contain one or more olefinic bonds, unless otherwise constrained by the definition. Such cycloalkyl groups include, by way of example, single ring structures, for example, cyclopropyl, cyclobutyl, cyclopentenyl, cyclohexyl, cyclooctyl, and the like, or multiple ring structures, for example, adamantyl, and bicyclo[2.2.1]heptane, or cyclic alkyl groups to which is fused an aryl group, for example, indane and the like. Cycloalkyl groups may further be substituted with one or more substituents selected from but not limited to, for example, halogen, hydroxyl, oxo, carboxy, carboxyalkyl, azido, alkenyl, alkynyl, alkoxy, cycloalkyl, cycloalkynyl, acyl acyloxy, aryl, heterocyclyl, heteroaryl.

The term "alkoxy" denotes the group O-alkyl wherein alkyl is the same as defined above.

The term "aralkyl" refers to alkyl-aryl linked through alkyl (wherein alkyl is the same as defined above) portion and the said alkyl portion contains carbon atoms from 1-6 and the aryl is as defined herein, after. The examples of aralkyl groups include benzyl and the like.

The term "aryl" herein refers to a carbocyclic aromatic group, for example phenyl or naphthyl ring and the like optionally substituted with one or more substituents selected from but not limited to, for example, halogen, hydroxyl, alkyl, alkenyl, alkynyl, cycloalkyl, alkoxy, acyl, aryloxy, $CF_3$, $COOR^d$ (wherein $R^d$ can be hydrogen, alkyl, alkenyl, cycloalkyl, aralkyl, heterocyclylalkyl or heteroarylalkyl), cyano, nitro, carboxy, heterocyclyl, heteroaryl, heterocyclylalkyl or heteroarylalkyl. The aryl group may optionally be fused with cycloalkyl group, wherein the said cycloalkyl group may optionally contain heteroatoms selected from O, N and S.

The term "aryloxy" denotes the group O— aryl wherein aryl is as defined above.

The term "heteroaryl" unless and otherwise specified refers to an aromatic ring structure or a bicyclic aromatic group with one or more heteroatom(s) independently selected from N, O and S and optionally substituted at any available position by substituent(s) selected from but not limited to halogen, hydroxyl, alkyl; alkenyl, alkynyl, cycloalkyl, acyl, carboxy, aryl, alkoxy, aralkyl, cyano, nitro, heterocyclyl, or heteroaryl. Examples of heteroaryl groups include oxazolyl, imidazolyl, pyrrolyl, 1,2,3,-triazolyl, 1,2,4-triazolyl tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, and the like.

The term "heterocyclyl" unless and otherwise specified refers to a cyclic, bicyclic or tricyclic cycloalkyl group, fully or partially unsaturated having 5 to 10 carbon atoms; with one or more heteroatom(s) independently selected from N, O and S, and are optionally benzofused or fused with heteroaryl of 5-6 ring members; the rings may be optionally substituted wherein the substituents are selected from but not limited to halogen, hydroxyl, alkyl, alkenyl, alkynyl, cycloalkyl, acyl, carboxy, aryl, alkoxy, aralkyl, cyano, nitro, heterocyclyl, or heteroaryl. Examples of heterocyclyl groups include but are not limited to oxazolidinyl, tetrahydrofuranyl, dihydrofuranyl, dihydropyridinyl, dihydroisooxazolyl, dihydrobenzoyl, azabicyclohexyl, dihydroindonyl, piperidinyl or piperazinyl.

"Heteroarylalkyl" refers to alkyl-heteroaryl group linked through alkyl portion, wherein the alkyl and heteroalkyl are the same as defined previously.

"Heterocyclylalkyl" refers to alkyl-heterocyclyl group linked through alkyl portion, wherein the alkyl and heterocyclyl are the same as defined previously.

Halogen refers to fluoro, chloro, bromo or iodo.

The term "Protecting Group" or "PG" refers to a group which is in a modified form to preclude undesired side reactions at the protected site. The term protecting group, unless otherwise specified, may be used with groups, for example, hydroxyl, amino, carboxyl and examples of such groups are found in T. W. Greene. et al. "*Protecting Groups in Organic Synthesis,*" 3$^{rd}$ Ed, Wiley, New York, which is incorporated herein by reference. The species of the carboxylic protecting groups, amino protecting groups or hydroxyl protecting groups employed are not critical, as long as the derivatised moieties/moiety is/are stable to conditions of subsequent reactions and can be removed without disrupting the remainder of the molecule. Examples of suitable hydroxyl and amino protecting groups include but are not limited to trimethylsilyl, triethylsilyl, o-nitrobenzyloxycarbonyl, p-nitrobenzyloxycarbonyl, t-butyldiphenylsilyl, t-butyldimethylsilyl, acetyl, trifluoroacetyl, benzyloxycarbonyl (CBz), t-butoxycarbonyl (Boc), 9-fluorenylmethylenoxycarbonyl, (Fmoc), 2,2,2-trichloroethyloxycarbonyl, allyloxycarbonyl and the like. Examples of suitable carboxy protecting groups are benzhydryl, o-nitrobenzyl, p-nitrobenzyl, 2-naphthylmethyl, alkyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

The term "therapeutically effective amount" means the amount of a compound that, when administered to a subject for treating a disease, is sufficient to effect such treatment for the disease. The "therapeutically effective amount" will vary depending on the compound, the disease and its severity, weight, physical condition and responsiveness of the subject to be treated, among other factors.

A "pharmaceutically acceptable salt" refers to salts prepared from pharmaceutically acceptable non-toxic bases or acids including inorganic or organic bases and inorganic or organic acids.

Asymmetric centres may exist in the compounds of the present invention. The compounds of Formula I may have one or more stereogenic centres and so can exhibit optical isomerism. All such isomers including enantiomers, diastereomers, and epimers are included within the scope of this invention. Furthermore, the invention includes such compounds as single isomers (R and/or S) and as mixtures, including racemates. If desired, racemic mixtures of the compounds may be separated so that the individual enantiomers are isolated. The separation may be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Starting materials of particular stereochemistry may either be commercially available or may be made by the methods described herein and resolved by techniques well known in the art.

The Formula I shows the structure of compounds without any preferred stereochemistry. Formula Ia shows the preferred stereochemistry at the carbon atom to which is attached the amino group of the β amino acid, from which these compounds are prepared.

The independent syntheses of these diastereomers or their chromatographic separations may be achieved as known in the art by appropriate modifications.

Certain compounds according to Formula I, can also exist as tautomers, which have different points of attachment of hydrogen accompanied by one or more double bond shifts. These tautomers, either separately or as mixtures, are also considered to be within the scope of the invention.

The present invention also encompasses geometrical isomers of compounds of Formula I and the mixtures thereof.

Particularly useful examples of the present invention include but are not limited to the compounds selected from Tables 1 to 5:

One embodiment of the present invention provides compounds of Formula Ib, wherein the compounds are selected from Table 1:

TABLE 1

| Compound No. | Structure |
|---|---|
| 1 | <br> |

TABLE 1-continued

| Compound No. | Structure |
|---|---|
| 2 | (structure: 2,4,5-trifluorophenyl-CH2-CH(NH2)-CH2-C(=O)-N[benzodiazepinone]) |
| 3 | (structure: 2,4,5-trifluorophenyl-CH2-CH(NH2)-CH2-C(=O)-N[benzodiazepinone with F]) |
| 4 | (structure: 2,4,5-trifluorophenyl-CH2-CH(NH2)-CH2-C(=O)-N[benzodiazepinone with F]) |
| 5 | (structure: 2,4,5-trifluorophenyl-CH2-CH(NH2)-CH2-C(=O)-N[benzodiazepinone with Cl]) |

TABLE 1-continued

| Compound No. | Structure |
|---|---|
| 6 | 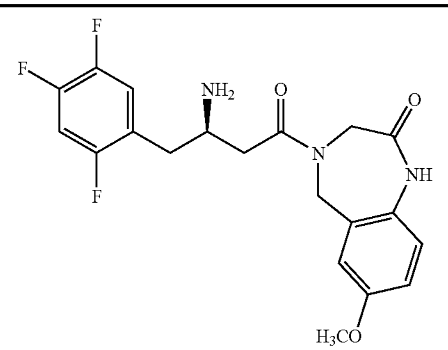 |
| 7 | 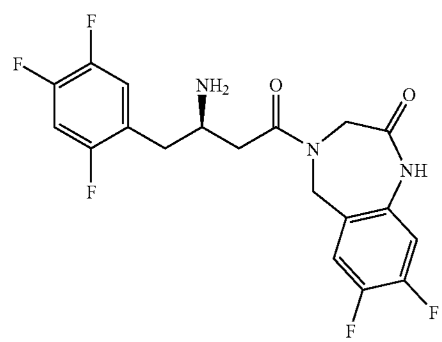 [SMILES: N[C@@H](CC(=O)N1CC(=O)Nc2cc(F)c(F)cc2C1)Cc1cc(F)c(F)cc1F] |
| 8 | 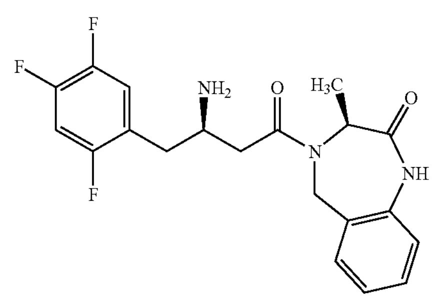 [SMILES: C[C@H]1C(=O)Nc2ccccc2CN1C(=O)C[C@H](N)Cc1cc(F)c(F)cc1F] |
| 9 | 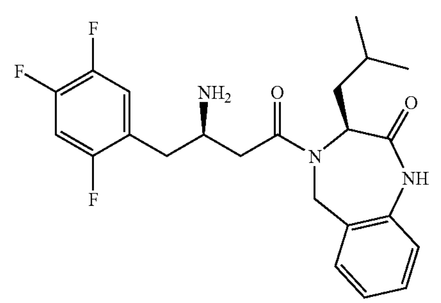 [SMILES: CC(C)C[C@H]1C(=O)Nc2ccccc2CN1C(=O)C[C@H](N)Cc1cc(F)c(F)cc1F] |
| 10 | 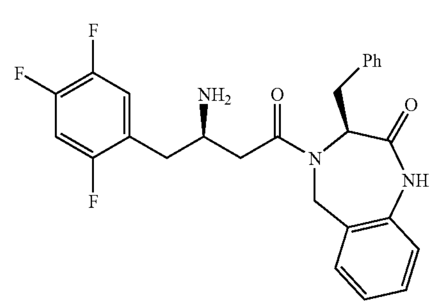 [SMILES: N[C@@H](CC(=O)N1Cc2ccccc2NC(=O)[C@@H]1Cc1ccccc1)Cc1cc(F)c(F)cc1F] |

TABLE 1-continued
| Compound No. | Structure |
|---|---|
| 11 | 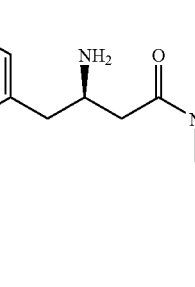 |
| 12 | 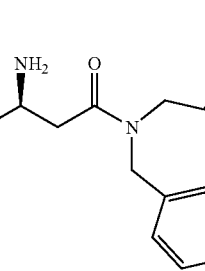 |
| 13 | 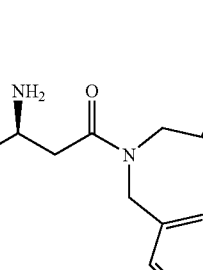 |
| 14 | 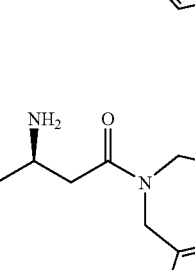 |
| 15 | 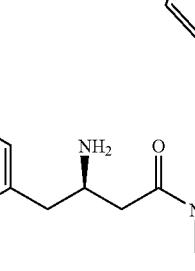 |

TABLE 1-continued
| Compound No. | Structure |
|---|---|
| 16 | 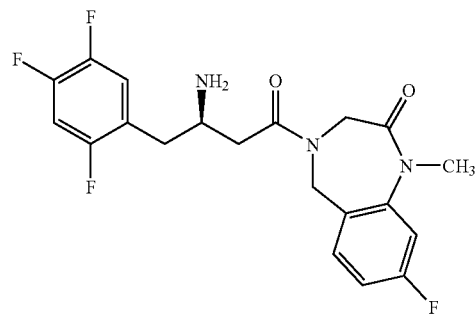 [SMILES: CN1C(=O)CN(C(=O)C[C@H](N)Cc2cc(F)c(F)cc2F)Cc2ccc(F)cc21] |
| 17 | 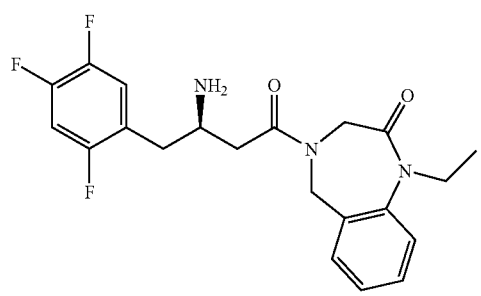 [SMILES: CCN1C(=O)CN(C(=O)C[C@H](N)Cc2cc(F)c(F)cc2F)Cc2ccccc21] |
| 18 | 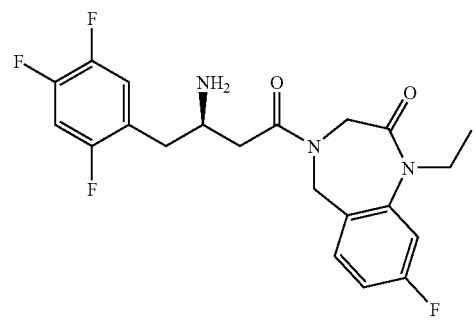 [SMILES: CCN1C(=O)CN(C(=O)C[C@H](N)Cc2cc(F)c(F)cc2F)Cc2ccc(F)cc21] |
| 19 | 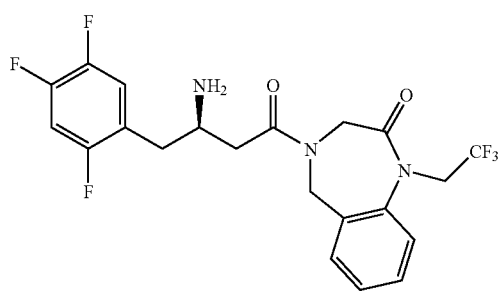 [SMILES: N[C@@H](CC(=O)N1CC(=O)N(CC(F)(F)F)c2ccccc2C1)Cc1cc(F)c(F)cc1F] |
| 20 | 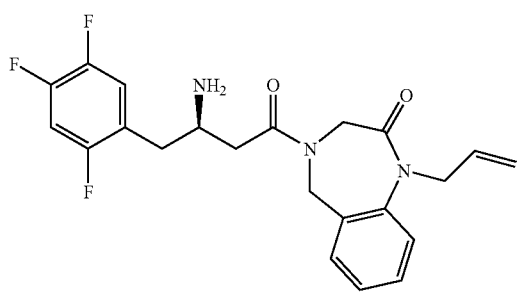 [SMILES: C=CCN1C(=O)CN(C(=O)C[C@H](N)Cc2cc(F)c(F)cc2F)Cc2ccccc21] |

TABLE 1-continued

| Compound No. | Structure |
|---|---|
| 21 | (2,4,5-trifluorophenyl)-CH₂-CH(NH₂)-C(=O)-N[benzodiazepinone with N-CH₂-cyclopropyl] |
| 22 | (2,4,5-trifluorophenyl)-CH₂-CH(NH₂)-C(=O)-N[benzodiazepinone with N-n-butyl] |
| 23 | (2,4,5-trifluorophenyl)-CH₂-CH(NH₂)-C(=O)-N[benzodiazepinone with N-benzyl] |
| 24 | (2,4,5-trifluorophenyl)-CH₂-CH(NH₂)-C(=O)-N[benzodiazepinone with N-CH₂-(2-CF₃-phenyl)] |
| 25 | (2,4,5-trifluorophenyl)-CH₂-CH(NH₂)-C(=O)-N[benzodiazepinone with N-CH₂-(2-CN-phenyl)] |

TABLE 1-continued

| Compound No. | Structure |
|---|---|
| 26 | 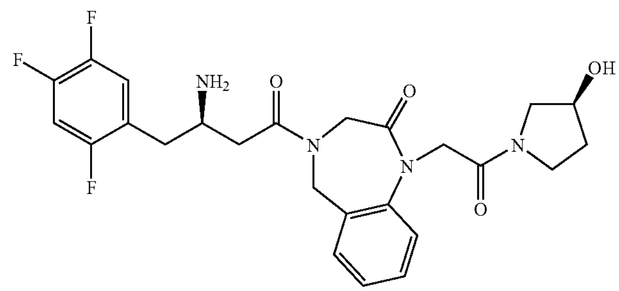 [SMILES: N[C@@H](CC(=O)N1CC(=O)N(CC(=O)N2CC[C@H](O)C2)c2ccccc2C1)Cc1cc(F)c(F)cc1F] |
| 27 | 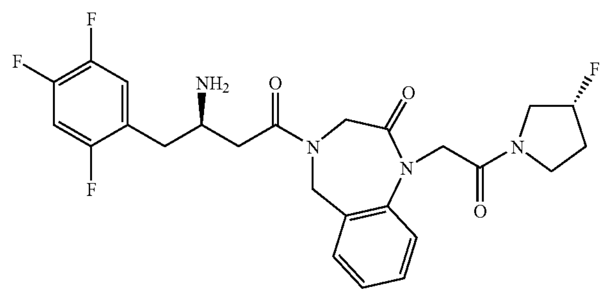 [SMILES: N[C@@H](CC(=O)N1CC(=O)N(CC(=O)N2CC[C@@H](F)C2)c2ccccc2C1)Cc1cc(F)c(F)cc1F] |
| 28 | 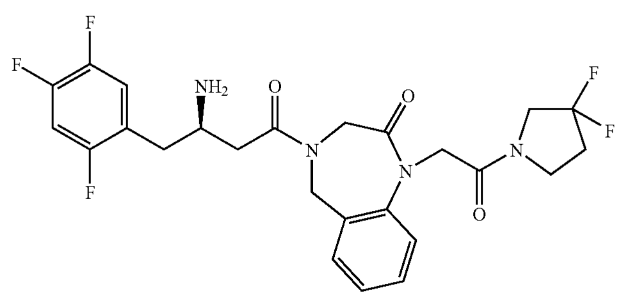 [SMILES: N[C@@H](CC(=O)N1CC(=O)N(CC(=O)N2CCC(F)(F)C2)c2ccccc2C1)Cc1cc(F)c(F)cc1F] |
| 29 | 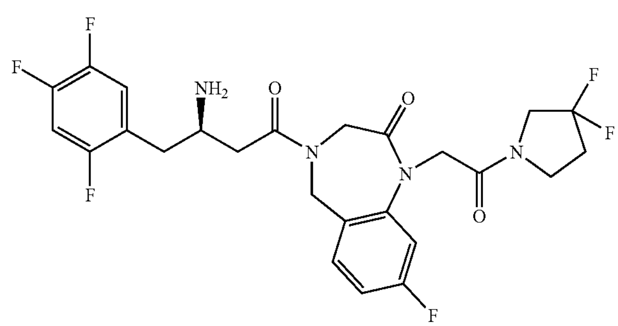 [SMILES: N[C@@H](CC(=O)N1CC(=O)N(CC(=O)N2CCC(F)(F)C2)c2cc(F)ccc2C1)Cc1cc(F)c(F)cc1F] |
| 30 | 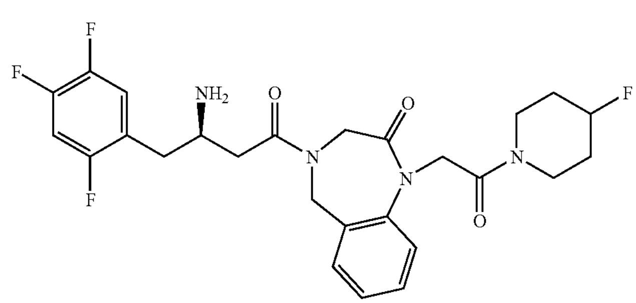 [SMILES: N[C@@H](CC(=O)N1CC(=O)N(CC(=O)N2CCC(F)CC2)c2ccccc2C1)Cc1cc(F)c(F)cc1F] |

TABLE 1-continued

| Compound No. | Structure |
|---|---|
| 31 | *(chemical structure)* |
| 32 | *(chemical structure)* |
| 33 | *(chemical structure)* |
| 34 | *(chemical structure)* |
| 35 | *(chemical structure)* |

TABLE 1-continued

| Compound No. | Structure |
|---|---|
| 36 | (structure) |
| 37 | (structure) |
| 38 | (structure) |
| 39 | (structure) |
| 40 | (structure) |

TABLE 1-continued

| Compound No. | Structure |
|---|---|
| 41 | 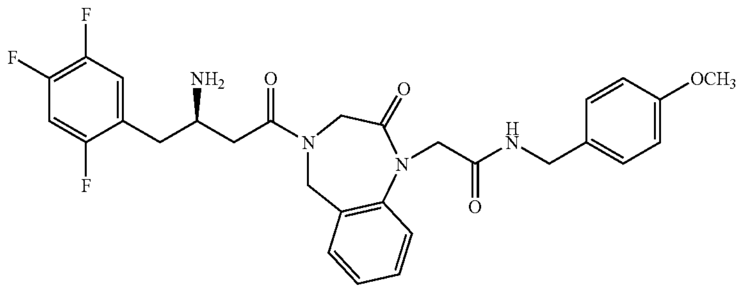 [SMILES: COc1ccc(CNC(=O)CN2C(=O)CN(C(=O)C[C@H](N)Cc3cc(F)c(F)cc3F)Cc3ccccc32)cc1] |
| 42 | 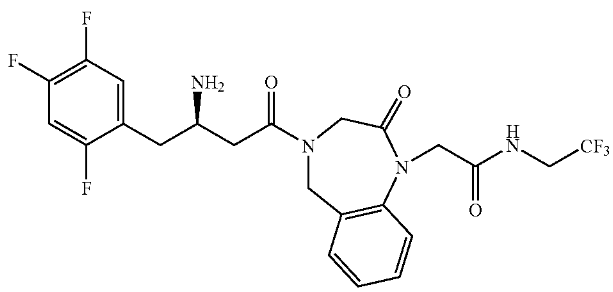 [SMILES: N[C@@H](CC(=O)N1CC(=O)N(CC(=O)NCC(F)(F)F)c2ccccc2C1)Cc1cc(F)c(F)cc1F] |
| 43 | 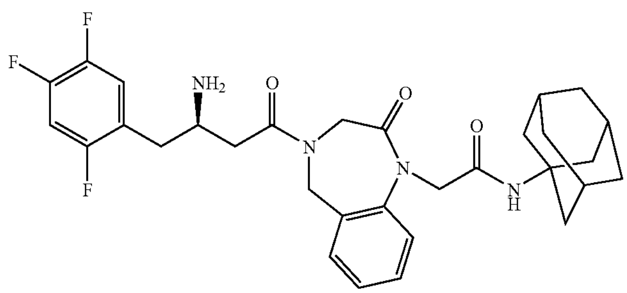 [SMILES: N[C@@H](CC(=O)N1CC(=O)N(CC(=O)NC23CC4CC(CC(C4)C2)C3)c2ccccc2C1)Cc1cc(F)c(F)cc1F] |
| 44 | 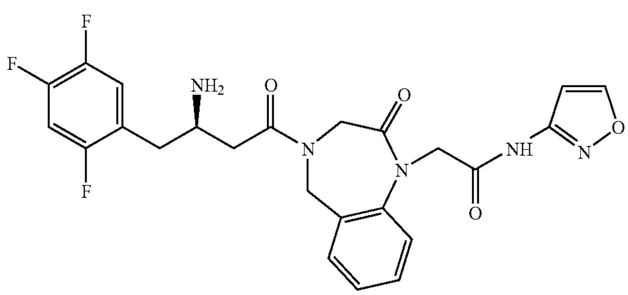 [SMILES: N[C@@H](CC(=O)N1CC(=O)N(CC(=O)Nc2ccon2)c2ccccc2C1)Cc1cc(F)c(F)cc1F] |
| 45 | 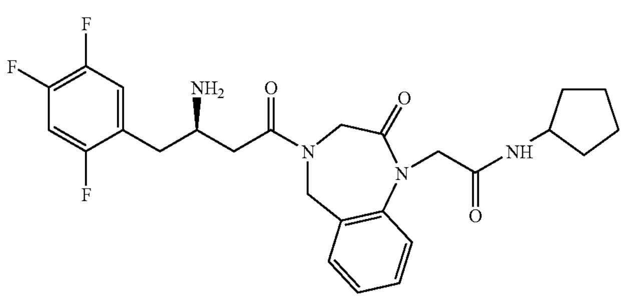 [SMILES: N[C@@H](CC(=O)N1CC(=O)N(CC(=O)NC2CCCC2)c2ccccc2C1)Cc1cc(F)c(F)cc1F] |

TABLE 1-continued
| Compound No. | Structure |
|---|---|
| 46 | 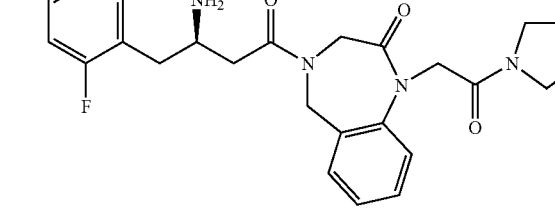 |
| 47 | 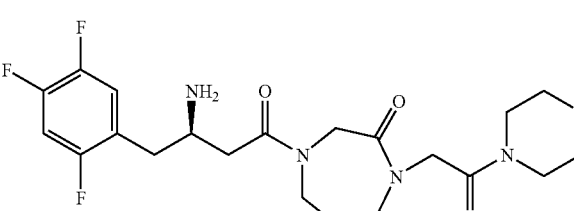 |
| 48 | 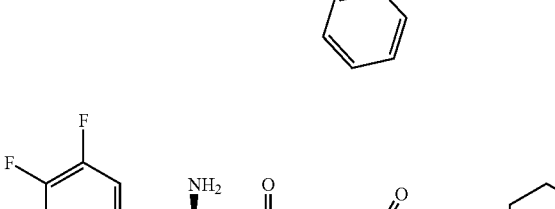 |
| 49 | 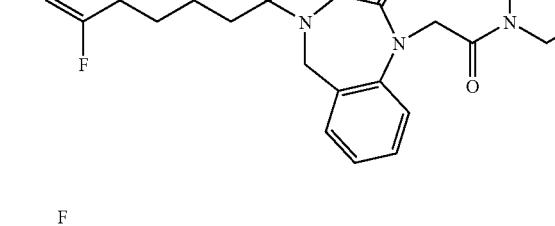 |
| 50 | 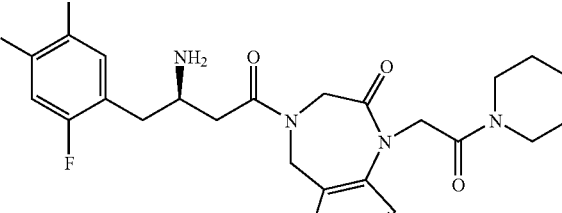 |

TABLE 1-continued

| Compound No. | Structure |
|---|---|
| 51 | (structure: 3-amino-4-(2,4,5-trifluorophenyl)butanoyl attached to a benzodiazepinone, with N-CH2-C(=O)- linker to 6,7-dimethoxy-1,2,3,4-tetrahydroisoquinoline) |

One embodiment of the present invention provides compounds of Formula Ie, wherein the compounds are selected from Table 2:

TABLE 2

| Compound No. | Structure |
|---|---|
| 52 | (structure: 3-amino-4-(2,4,5-trifluorophenyl)butanoyl attached to a [1,2,4]triazolo-benzodiazepine) |
| 53 | (structure: 3-amino-4-(2,4,5-trifluorophenyl)butanoyl attached to a 1-methyl-[1,2,4]triazolo-benzodiazepine) |
| 54 | (structure: 3-amino-4-(2,4,5-trifluorophenyl)butanoyl attached to a 1-methyl-[1,2,4]triazolo-benzodiazepine with F on benzo ring) |

TABLE 2-continued

| Compound No. | Structure |
|---|---|
| 55 | 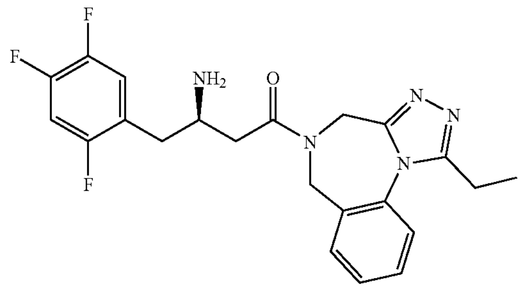 [SMILES: CCc1nnc2n1-c1ccccc1CN(C(=O)C[C@H](N)Cc1cc(F)c(F)cc1F)C2] |
| 56 | 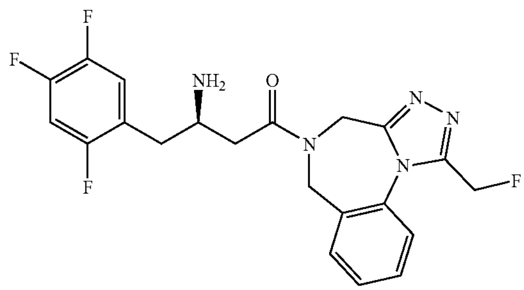 [SMILES: N[C@@H](CC(=O)N1Cc2ccccc2-n2c(CF)nnc2C1)Cc1cc(F)c(F)cc1F] |
| 57 | 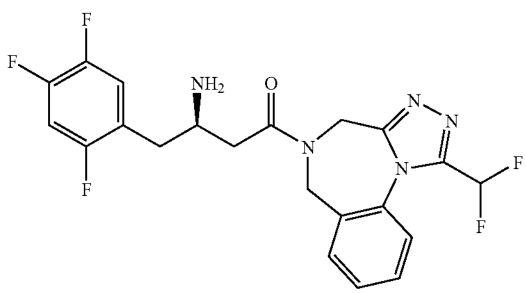 [SMILES: N[C@@H](CC(=O)N1Cc2ccccc2-n2c(nnc2C(F)F)C1)Cc1cc(F)c(F)cc1F] |
| 58 | 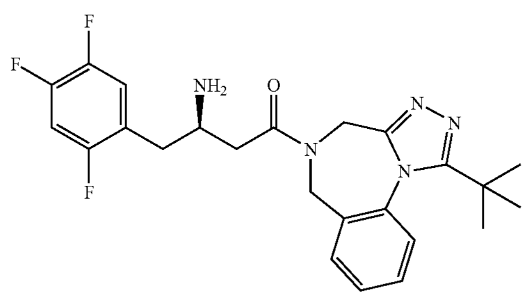 [SMILES: CC(C)(C)c1nnc2n1-c1ccccc1CN(C(=O)C[C@H](N)Cc1cc(F)c(F)cc1F)C2] |
| 59 | 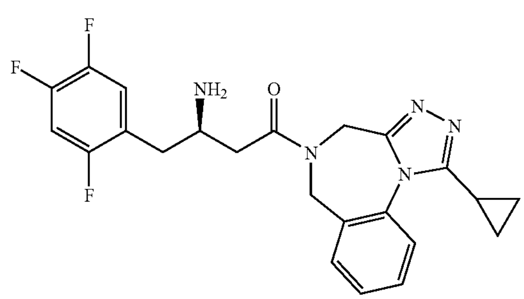 [SMILES: N[C@@H](CC(=O)N1Cc2ccccc2-n2c(nnc2C2CC2)C1)Cc1cc(F)c(F)cc1F] |

TABLE 2-continued

| Compound No. | Structure |
|---|---|
| 60 | 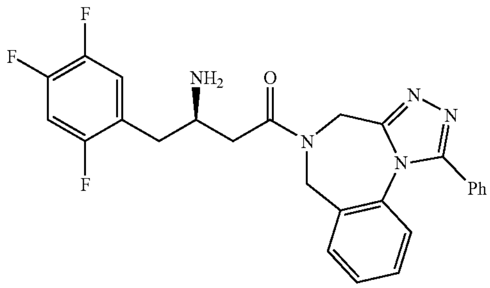 [SMILES: N[C@@H](CC(=O)N1Cc2ccccc2-n2c(nnc2-c2ccccc2)C1)Cc1cc(F)c(F)cc1F] |
| 61 | 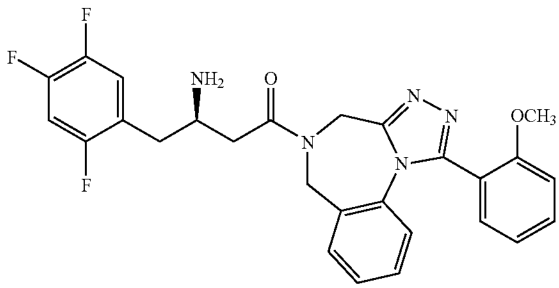 [SMILES: COc1ccccc1-c1nnc2n1-c1ccccc1CN(C(=O)C[C@H](N)Cc1cc(F)c(F)cc1F)C2] |
| 62 | 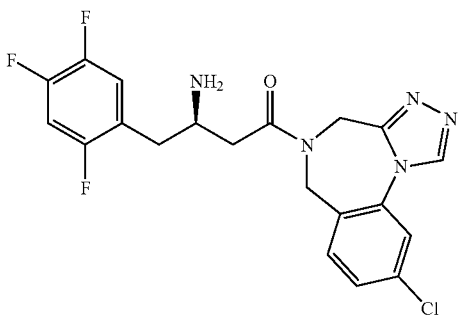 [SMILES: N[C@@H](CC(=O)N1Cc2ccc(Cl)cc2-n2cnnc2C1)Cc1cc(F)c(F)cc1F] |
| 63 | 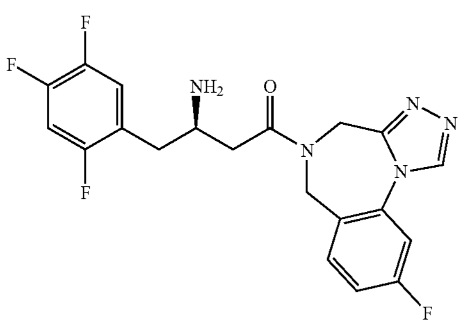 [SMILES: N[C@@H](CC(=O)N1Cc2ccc(F)cc2-n2cnnc2C1)Cc1cc(F)c(F)cc1F] |
| 64 | 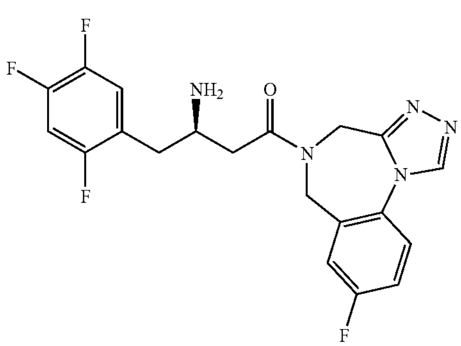 [SMILES: N[C@@H](CC(=O)N1Cc2cc(F)ccc2-n2cnnc2C1)Cc1cc(F)c(F)cc1F] |

TABLE 2-continued

| Compound No. | Structure |
|---|---|
| 65 | (structure) |
| 66 | (structure) |

One embodiment of the present invention provides compounds of Formula If, wherein the compounds are selected from Table 3:

TABLE 3

| Compound No. | Structure |
|---|---|
| 67 | (structure) |
| 68 | (structure) |

TABLE 3-continued

| Compound No. | Structure |
| --- | --- |
| 69 | 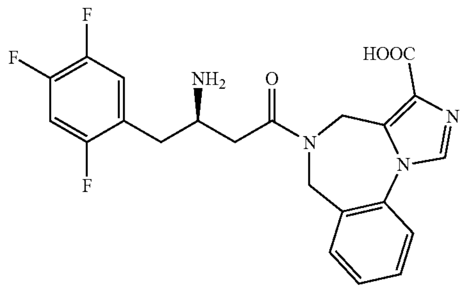 [SMILES: CCOC(=O)c1ncn2c1CN(C(=O)C[C@H](N)Cc1cc(F)c(F)cc1F)Cc1ccccc1-2] |
| 70 | 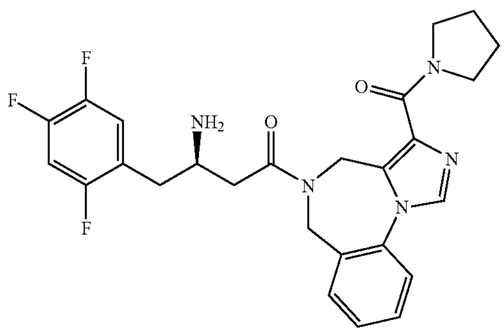 [SMILES: N[C@@H](CC(=O)N1Cc2ccccc2-n2cnc(C(=O)N3CCCC3)c2C1)Cc1cc(F)c(F)cc1F] |
| 71 | 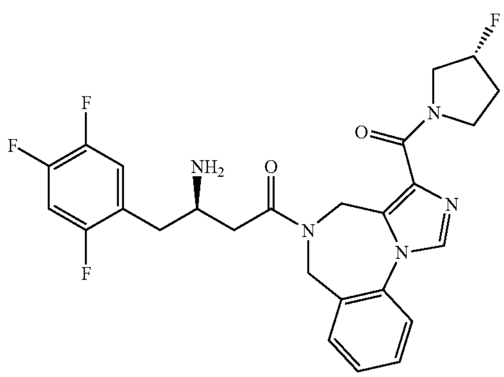 [SMILES: N[C@@H](CC(=O)N1Cc2ccccc2-n2cnc(C(=O)N3CC[C@@H](F)C3)c2C1)Cc1cc(F)c(F)cc1F] |
| 72 | 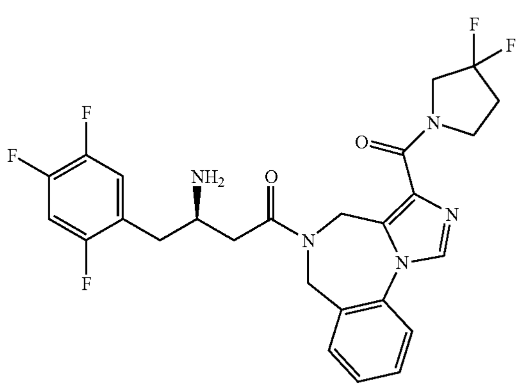 [SMILES: N[C@@H](CC(=O)N1Cc2ccccc2-n2cnc(C(=O)N3CCC(F)(F)C3)c2C1)Cc1cc(F)c(F)cc1F] |

TABLE 3-continued

| Compound No. | Structure |
| --- | --- |
| 73 | 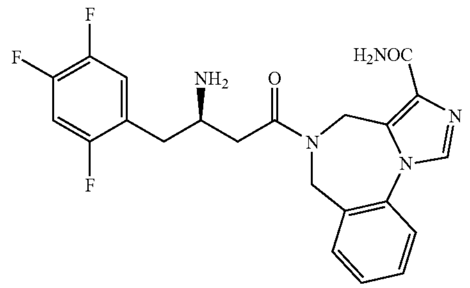 [SMILES: NC(=O)c1ncn2c1CN(C(=O)C[C@H](N)Cc1cc(F)c(F)cc1F)Cc1ccccc1-2] |
| 74 | 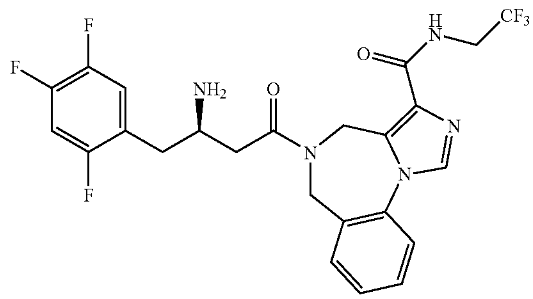 [SMILES: N[C@@H](CC(=O)N1Cc2ccccc2-n2cnc(C(=O)NCC(F)(F)F)c2C1)Cc1cc(F)c(F)cc1F] |
| 75 | 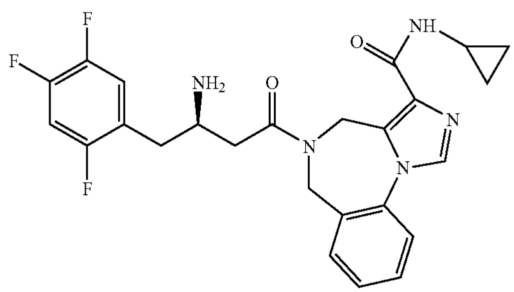 [SMILES: N[C@@H](CC(=O)N1Cc2ccccc2-n2cnc(C(=O)NC3CC3)c2C1)Cc1cc(F)c(F)cc1F] |
| 76 | 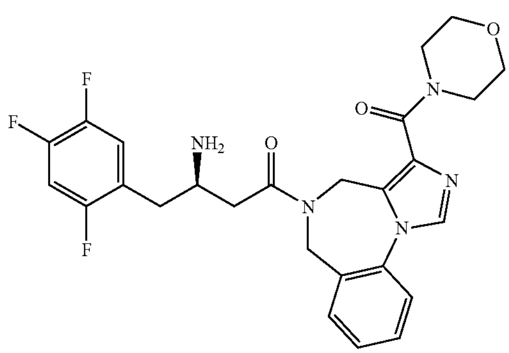 [SMILES: N[C@@H](CC(=O)N1Cc2ccccc2-n2cnc(C(=O)N3CCOCC3)c2C1)Cc1cc(F)c(F)cc1F] |
| 77 | 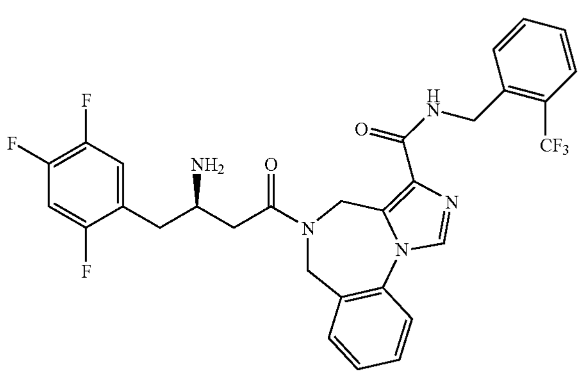 [SMILES: N[C@@H](CC(=O)N1Cc2ccccc2-n2cnc(C(=O)NCc3ccccc3C(F)(F)F)c2C1)Cc1cc(F)c(F)cc1F] |

TABLE 3-continued
| Compound No. | Structure |
|---|---|
| 78 | 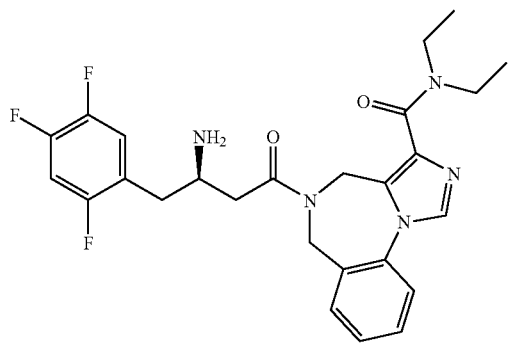 [SMILES: CCN(CC)C(=O)c1ncn2c1CN(C(=O)C[C@H](N)Cc1cc(F)c(F)cc1F)Cc1ccccc1-2] |
| 79 | 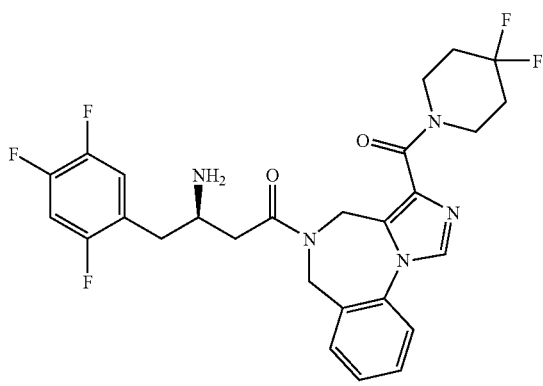 [SMILES: N[C@@H](CC(=O)N1Cc2ccccc2-n2cnc(C(=O)N3CCC(F)(F)CC3)c2C1)Cc1cc(F)c(F)cc1F] |
| 80 | 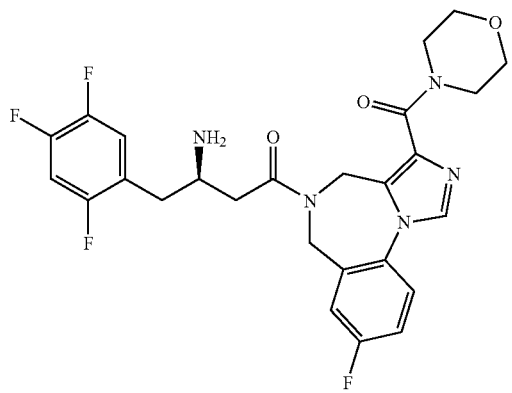 [SMILES: N[C@@H](CC(=O)N1Cc2cc(F)ccc2-n2cnc(C(=O)N3CCOCC3)c2C1)Cc1cc(F)c(F)cc1F] |
| 81 | 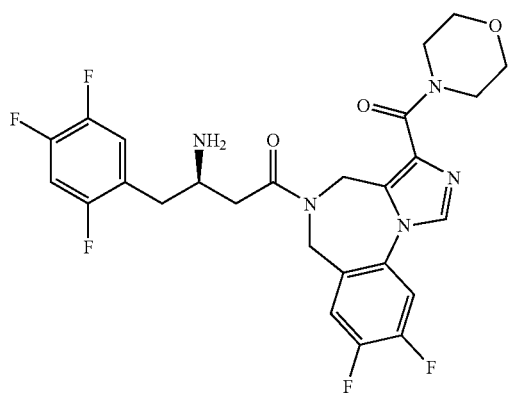 [SMILES: N[C@@H](CC(=O)N1Cc2cc(F)c(F)cc2-n2cnc(C(=O)N3CCOCC3)c2C1)Cc1cc(F)c(F)cc1F] |

TABLE 3-continued

| Compound No. | Structure |
|---|---|
| 82 | 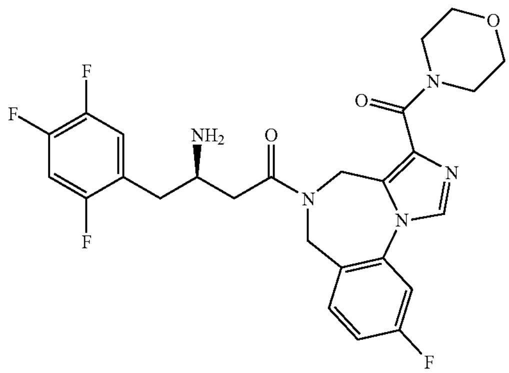 [SMILES: N[C@@H](CC(=O)N1Cc2ccc(F)cc2-n2cnc(C(=O)N3CCOCC3)c2C1)Cc1cc(F)c(F)cc1F] |
| 83 | 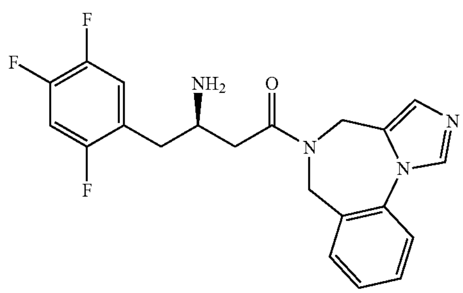 |
| 84 | 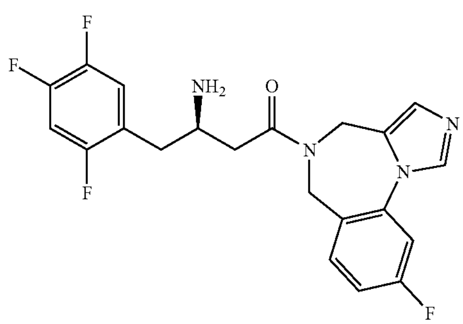 |
| 85 | 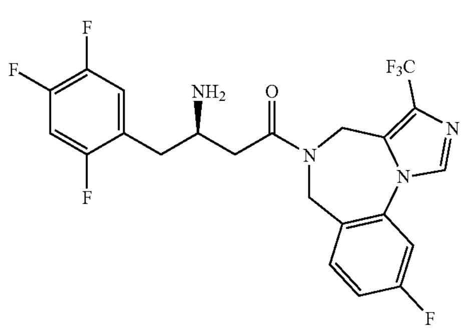 [SMILES: N[C@@H](CC(=O)N1Cc2ccc(F)cc2-n2cnc(C(F)(F)F)c2C1)Cc1cc(F)c(F)cc1F] |

One embodiment of the present invention provides compound of Formula Ig wherein the compounds are selected from Table 4:
TABLE 4
| Compound No. | Structure |
| --- | --- |
| 86 | 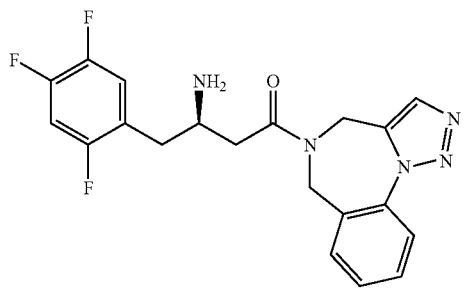 [SMILES: N[C@@H](CC(=O)N1Cc2ccccc2-n2nncc2C1)Cc1cc(F)c(F)cc1F] |
| 87 | 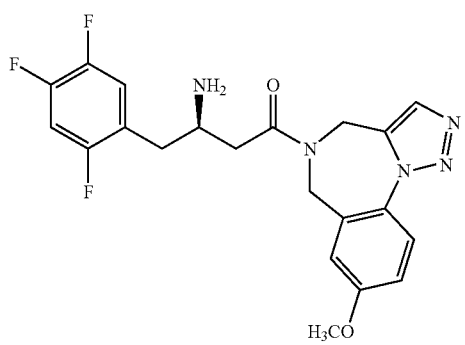 [SMILES: COc1ccc2c(c1)CN(C(=O)C[C@H](N)Cc1cc(F)c(F)cc1F)Cc1cnnn1-2] |
| 88 | 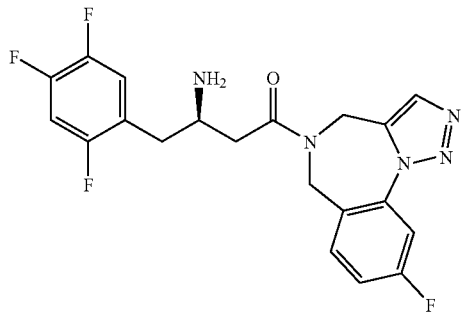 [SMILES: N[C@@H](CC(=O)N1Cc2ccc(F)cc2-n2nncc2C1)Cc1cc(F)c(F)cc1F] |
| 89 | 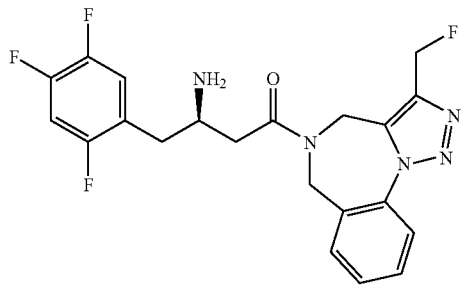 [SMILES: N[C@@H](CC(=O)N1Cc2ccccc2-n2nnc(CF)c2C1)Cc1cc(F)c(F)cc1F] |

TABLE 4-continued
| Compound No. | Structure |
|---|---|
| 90 | 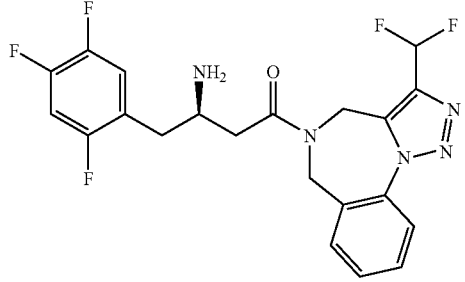 [SMILES: N[C@@H](CC(=O)N1Cc2ccccc2-n2nnc(C(F)F)c2C1)Cc1cc(F)c(F)cc1F] |
| 91 | 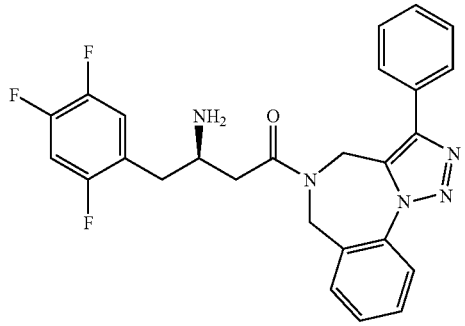 [SMILES: N[C@@H](CC(=O)N1Cc2ccccc2-n2nnc(-c3ccccc3)c2C1)Cc1cc(F)c(F)cc1F] |
| 92 | 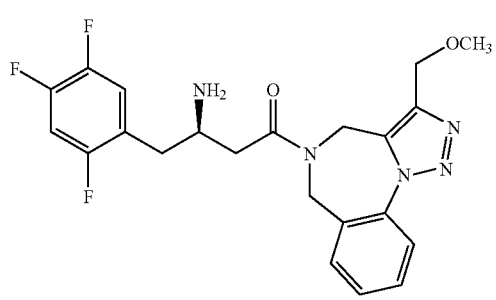 [SMILES: COCc1nnn2c1CN(C(=O)C[C@H](N)Cc1cc(F)c(F)cc1F)Cc1ccccc1-2] |
| 93 | 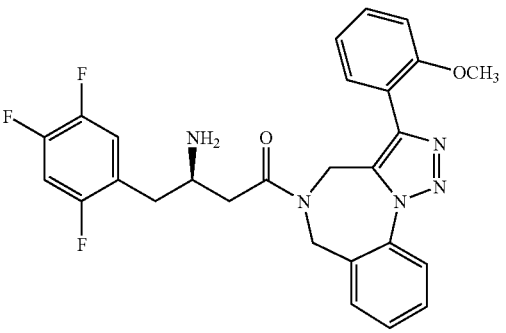 [SMILES: COc1ccccc1-c1nnn2c1CN(C(=O)C[C@H](N)Cc1cc(F)c(F)cc1F)Cc1ccccc1-2] |
| 94 | 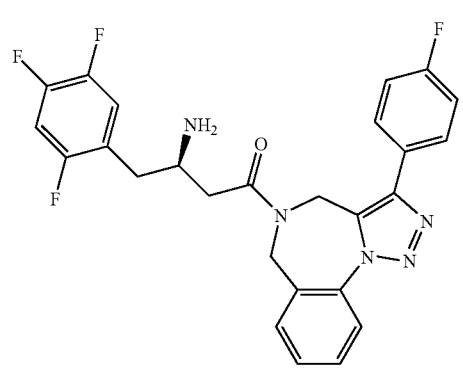 [SMILES: N[C@@H](CC(=O)N1Cc2ccccc2-n2nnc(-c3ccc(F)cc3)c2C1)Cc1cc(F)c(F)cc1F] |

One embodiment of the present invention provides compound of Formula Ih, wherein the compound is in Table 5

TABLE 5

| Compound No. | Structure |
|---|---|
| 95 | 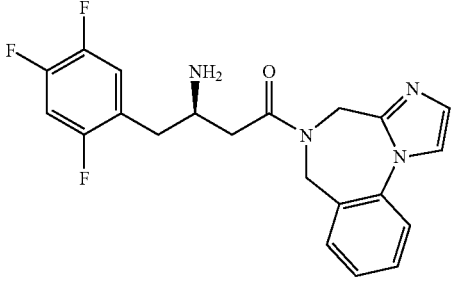 [SMILES: N[C@@H](CC(=O)N1Cc2ccccc2-n2ccnc2C1)Cc1cc(F)c(F)cc1F] |

The compounds of the present invention can be prepared from β-amino acid intermediates such as those of Formula II, wherein Ar is as defined herein and heterocyclic intermediates such as those of Formula III, wherein r, $R^1$, $R^2$, $R^3$, $R^4$, $R^5$, $R^6$, $R^7$ and $R^8$ are as defined herein, using standard coupling conditions followed by deprotection of the amine protecting functionality. Examples of standard coupling conditions include EDC [1-ethyl-3-(3-dimethylaminopropyl) carbodiimide]/HOBT (1-hydroxybenzotriazole); DCC (dicyclohexyl carbodiimide), DMAP (4-dimethylaminopyridine); HATU [O-(7-azabenzotriazole-yl)-N,N,N',N'-tetramethyluronium hexafluorophosphate; HOAT (1-hydroxy-7-azabenzotriazole); BOP [(benzotriazolyl-1-yloxy)-tris(dimethylamine) phosphonium hexafluorophosphate]; mixed anhydride method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like. Examples of reagents used for deprotecting the amine protecting moiety will depend upon the nature of protecting group used. Examples of suitable amino protecting groups include but are not limited to acetyl, trifluoroacetyl, benzyloxycarbonyl (CBz), t-butoxycarbonyl (Boc), 9-fluorenylmethylenoxycarbonyl (Fmoc), 2,2,2-trichloroethyloxycarbonyl, allyloxycarbonyl and the like. The appropriate conditions for the removal of the amine protecting groups can be readily selected by those having well known skill in the art. Examples of reagents used for deprotecting the amine protecting moiety include but are not limited to use of acidic conditions (trifluoroacetic acid, hydrochloric acid, phosphoric acid, p-toluenesulphonic acid and the like), basic conditions (piperidine and the like) or hydrogenation conditions (palladium on charcoal or platinum and the like). The resulting compounds may be in the form of free amine or salt depending upon the nature of the protecting group and the corresponding deprotecting reagent used. In case the deprotection results in the formation of salt, the corresponding amine can easily be obtained by treating the salt with an appropriate base such as triethylamine, diethylisopropylamine, sodium bicarbonate, sodium hydroxide or the like.

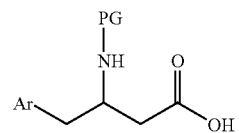

Formula II

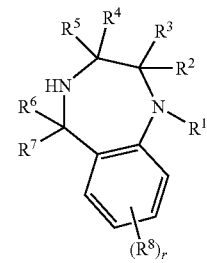

Formula III

Enantiomerically pure β-amino acids having the Formula II may be conveniently synthesized using methods described in *Tetrahedron*, 1994, 32, 9517; *Enantioselective Synthesis of β-Amino Acids*, Ed., Wiley-VCH, New York: 1997; *Aldrichimica Acta*, 1994, 27:3 and *Angew Chem Int Ed Engl.* 1981, 20, 798.

In particular, 3-amino-4-(2,4,5-trifluoro-phenyl)-butyric acid may be synthesized as reported in the patent application WO 2004069162 and in *J. Med. Chem.*, 2005, 48, 141.

Compounds of Formula III can easily be prepared from compounds of Formula IV, wherein r, $R^1$, $R^2$, $R^3$, $R^4$, $R^5$, $R^6$, $R^7$ and $R^8$ are as defined herein, by deprotecting the amine protecting group, using standard deprotecting reagents. The resulting compounds may be in the form of free amine or salt depending upon the nature of the protecting group and the corresponding deprotecting reagent used. Examples of reagents used for deprotecting the amine protecting moiety include but are not limited to use of acidic conditions (trifluoroacetic acid, hydrochloric, acid, phosphoric acid, p-toluenesulphonic acid and the like), basic conditions (piperidine and the like) or hydrogenation conditions (palladium on charcoal or platinum and the like). The resulting compounds may be in the form of free amine or salt depending upon the nature of the protecting group and the corresponding deprotecting reagent used. In case the deprotection results in the formation of salt, the corresponding amine can easily be obtained by treating the salt with an appropriate base such as triethylamine, diethylisopropylamine, sodium bicarbonate, sodium hydroxide or the like.

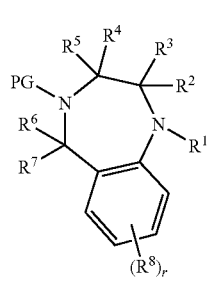

Formula IV

Compounds of Formula IV can be easily prepared by a variety of methods familiar to those skilled in the art. Some common routes for the preparation of such compounds are illustrated in Schemes 1 to 11.

Compounds of Formula IV, can generally be synthesised from compounds of Formula V, wherein r, $R^4$, $R^5$, $R^6$, $R^7$ and $R^8$ are as defined herein [Ref: *Synthesis*, 2005, 1881]. One convenient route for the synthesis of compounds of Formula V is outlined in Scheme 1.

Formula V

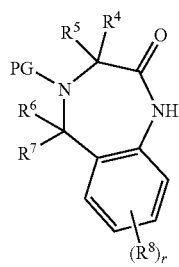

The compounds of Formula V can be prepared starting from the appropriate 2-nitrobenzyl bromide which is coupled with the required ester of an amino acid in the presence of a base such as DIPEA, NMM, potassium carbonate and the like and a solvent such as DMF, THF, acetonitrile and the like, resulting in the formation of compounds of Formula VI, wherein r, $R^4$, $R^5$ and $R^8$ are as defined herein. The compounds of Formula VI are then protected at the amine functionality using the appropriate protecting group resulting in compounds of Formula VII. Compounds of Formula VII, wherein r, $R^4$, $R^5$ and $R^8$ are as defined herein, are then converted to compounds of Formula VIII, wherein r, $R^4$, $R^5$ and $R^8$ are as defined herein, by hydrolyzing the ester moiety under basic conditions. Examples of basic hydrolyzing reagents include sodium hydroxide, lithium hydroxide, potassium hydroxide and the like, which can be used in appropriate solvents like THF/water, dioxane/water or THF/MeOH/water. The nitro group of Formula VIII, can then be reduced to the corresponding amino compounds of Formula IX, wherein r, $R^4$, $R^5$ and $R^8$ are as defined herein, by a variety of reducing agents such as hydrogenation over an appropriate catalyst such as palladium, platinum, or ruthenium on activated charcoal or chemical methods such as reaction with $FeCl_3$ or $SnCl_2/HCl$ or $Fe/NH_4Cl$ or $NiCl_2/NaBH_4$ or Fe/HCl familiar to those skilled in the art. Compounds of Formula IX containing an amine and carboxylic acid functionality are then cyclized under standard coupling conditions, for example, using EDC [1-ethyl-3-(3-dimethylaminopropyl) carbodiimide]/HOBT (1-hydroxybenzotriazole) or DCC (dicyclohexyl carbodiimide), DMAP (4-dimethylaminopyridine) or HATU [O-(7-azabenzotriazole-yl)-N,N,N',N'-tetramethyluronium hexafluorophosphate or HOAT (1-hydroxy-7-azabenzotriazole) or BOP [(benzotriazolyl-1-yloxy)-tris(dimethylamine) phosphonium hexafluorophosphate] or by mixed anhydride method using ethyl chloroformate or methyl chloroformate in a suitable solvent such as DMF, DCM, acetonitrile, toluene or THF and the like or mixtures thereof and in the presence of a suitable base such as NMM (N-methylmorpholine), DIPEA (N,N-diisopropylethylamine) or triethylamine, to afford compounds of Formula V.

Scheme 1

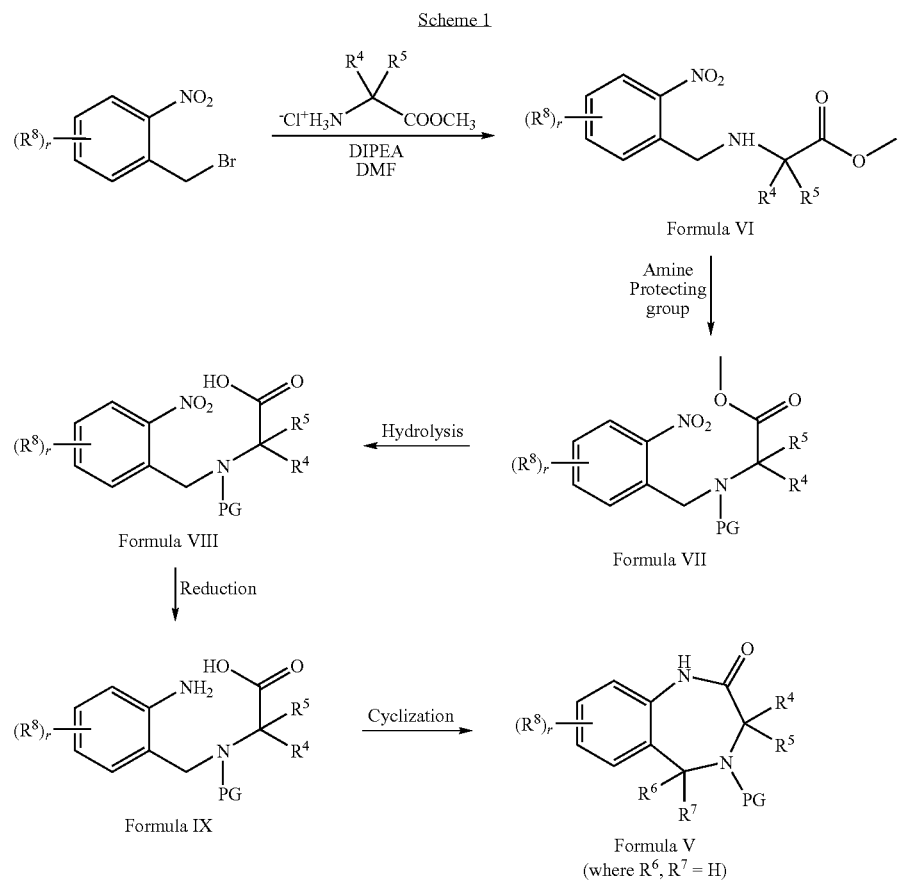

A convenient route to prepare compounds of Formula XVII, wherein $R^4$ and $R^5$ are as defined herein, is as described in Scheme 2.

The compounds of Formula XVII can be prepared starting from 2-amino-4,5-difluorobenzoic acid, which is reduced using appropriate reducing agents such as lithium aluminium hydride or borane dimethylsulphide or mixed anhydride/sodium borohydride in a suitable solvent such as diethyl ether or THF or DCM or mixtures thereof, to obtain compounds of Formula X. The compounds of Formula X are then protected using amine protecting reagents such as benzylchloroformate or di-tert-butyl dicarbonate or Fluorenylmethyloxycarbonyl chloride (Fmoc-Cl) in a suitable solvent such as DCM or dioxane or THF, resulting in compounds of Formula XI. The compounds of Formula, XI are then chlorinated under standard chlorinating conditions using thionyl chloride or $POCl_3$ or $PCl_5$, resulting in the compounds of Formula XII, which are further coupled with the suitably protected amino acid using an appropriate base such as DIPEA or triethylamine or potassium carbonate or cesium carbonate or sodium carbonate and the like in an appropriate solvent to afford compounds of Formula XIII, wherein $R^4$ and $R^5$ are as defined herein. The compounds of Formula XIII are then again, protected at the amine moiety using a different protecting group than the earlier used to protect compounds of Formula X, to form compounds of Formula XIV, wherein $R^4$ and $R^5$ are as defined herein, which are then hydrolysed under basic conditions resulting in compounds of Formula XV, wherein $R^4$ and $R^5$ are as defined herein. Examples of basic hydrolyzing reagents include sodium hydroxide, lithium hydroxide, potassium hydroxide and the like, which can be used in appropriate solvents like THF/water, dioxane/water or THF/MeOH/water. Compounds of Formula XV are selectively deprotected at one of the amine moieties to afford compounds of Formula XVI, wherein $R^4$ and $R^5$ are as defined herein, which are then subjected to internal cyclization to form compounds of Formula XVII. The appropriate conditions for the selective removal of one of the amine protecting groups can be readily selected by those having well known skill in the art. Example of standard cyclization conditions include EDC [1-ethyl-3-(3-dimethylaminopropyl)carbodiimide]/HOBT (1-hydroxybenzotriazole); DCC (dicyclohexyl carbodiimide), DMAP (4-dimethylaminopyridine); HATU [O-(7-azabenzotriazole-yl)-N,N,N',N'-tetramethyluronium hexafluorophosphate; HOAT (1-hydroxy-7-azabenzotriazole); BOP [(benzotriazolyl-1-yloxy)-tris(dimethylamine) phosphonium hexafluorophosphate]; mixed anhydride, method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like.

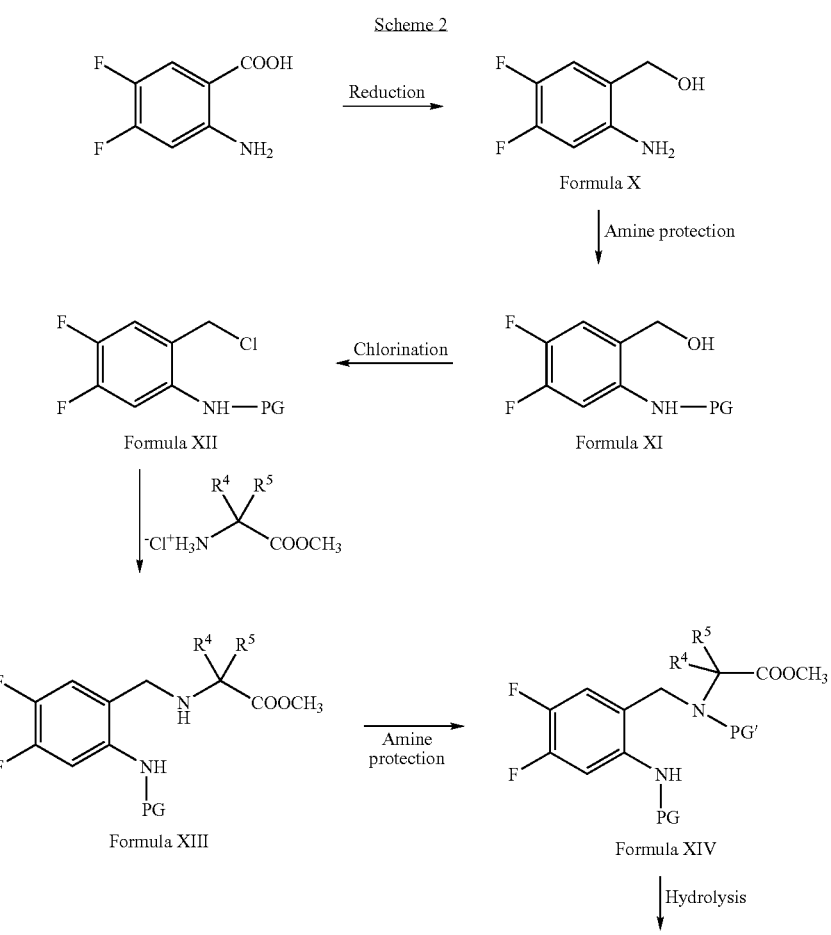

Scheme 2

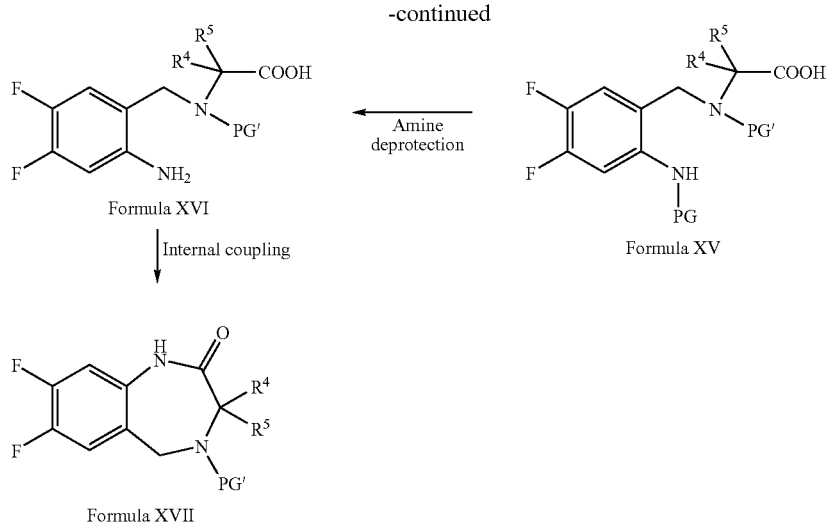

The compounds of the Formula XX, wherein r, $R^4$, $R^5$, $R^8$ and $R^c$ are as defined herein, can be prepared from compounds of Formula V, as described in Scheme 3. The compounds of Formula V are converted to compounds of Formula XVIII, wherein r, $R^4$; $R^5$ and $R^8$ are as defined herein, by reacting with Lawesson's reagent or phosphorus pentasulphide in the presence of a suitable solvent such as toluene, benzene, xylene, dioxane and the like or mixtures thereof under suitable heating conditions [Ref: *J. Org. Chem.*, 1964, 29, 231]. The compounds of Formula XVIII are then reacted with compounds of Formula XIX, wherein $R^c$ is as defined herein, under heating conditions in an appropriate solvent such as benzene or toluene or DMSO or mixtures thereof to give compounds of Formula XX [Ref: reported in patent application no. WO 9620941].

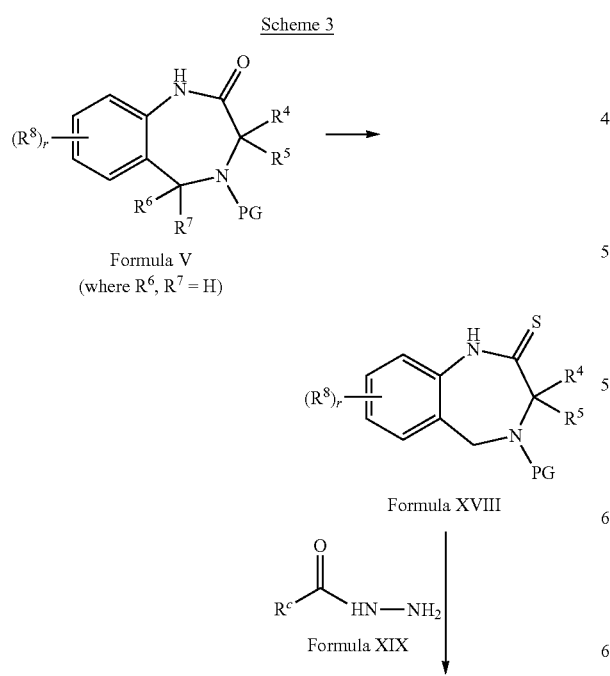

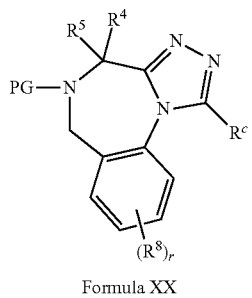

The compounds of Formula XIX are either commercially available or can be prepared by those skilled in the art. One convenient route for the preparation of such compounds is described in Scheme 4. Starting with the commercially available tert-butyl carbazate and reacting it with the appropriately substituted acid or acid chloride, under standard coupling conditions, compounds of Formula XXI, wherein $R^c$ is as defined herein, can be prepared, which can then be deprotected under acidic conditions such as using trifluoroacetic acid or by passing hydrochloride gas or p-toluenesulphonic acid and the like, resulting in compounds of formula XIX or their respective salts. Examples of standard coupling conditions include EDC [1-ethyl-3-(3-dimethylaminopropyl)carbodiimide]/HOBT (1-hydroxybenzotriazole); DCC (dicyclohexyl carbodiimide), DMAP (4-dimethylaminopyridine); HATU [O-(7-azabenzotriazole-yl) N,N,N'N'-tetramethyluronium hexafluorophosphate; HOAT (1-hydroxy-7-azabenzotriazole); BOP [(benzotriazolyl-1-yloxy)-tris(dimethylamine) phosphonium hexafluorophosphate]; mixed anhydride method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like.

Scheme 4

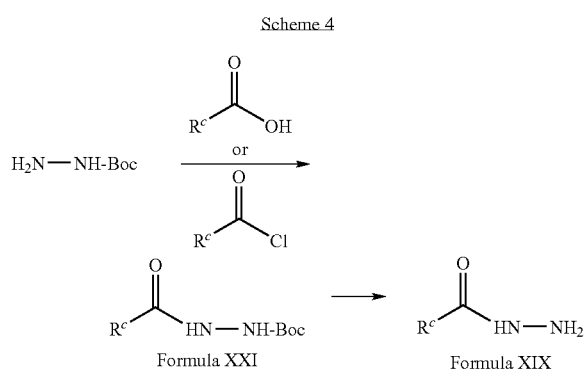

The compounds of Formula XXIX, wherein r, $R^c$ and $R^8$ are as defined herein, can be prepared following the procedure described in Scheme 5, starting from the appropriately substituted 2-nitro benzyl bromide, which can be converted to the corresponding azides using sodium azide in a suitable solvent like DMF or THF or toluene under heating conditions to form compounds of Formula XXII, wherein r and $R^8$ are as defined herein, which are then reduced under neutral reducing conditions using triphenyl phosphine in THF/water, resulting in the formation of corresponding amines of Formula XXIII, wherein r and $R^8$ are as defined herein. The amine functionality of compounds of Formula XXIII was protected with a suitable protecting group such as benzylchloroformate or di-tert-butyl dicarbonate or Fluorenylmethyloxycarbonyl chloride (Fmoc-Cl) in a suitable solvent such as DCM or dioxane or THF, to afford compounds of Formula XXIV, wherein r and $R^8$ are as defined herein. The nitro group of compounds of Formula XXIV can then be reduced to the corresponding amino groups of Formula XXV, wherein r and $R^8$ are as defined herein, by a variety of reducing agents such as hydrogenation over an appropriate catalyst such as palladium, platinum, or ruthenium on activated charcoal or chemical methods such as reaction with $FeCl_3$ or $SnCl_2/HCl$ or $Fe/NH_4Cl$ or $NiCl_2/NaBH_4$ familiar to those skilled in the art. The amino compounds of Formula XXV are further subjected to diazotization reaction using sodium nitrite in the presence of acetic acid/water, followed by reaction with sodium azide, to afford compounds of Formula XXVI, wherein r and $R^8$ are as defined herein. The compounds of Formula XXVI are then reacted with propargyl bromides of the Formula XXVII wherein $R^c$ is as defined herein, resulting in the formation of compounds of Formula XXVIII, wherein r, $R^8$ and $R^c$ are as defined herein, which upon heating in a suitable solvent like benzene, toluene, xylene and the like or mixtures thereof, resulted in the formation of compounds of Formula XXIX. [Ref: Org. Lett., 2008, 10, 1617]. The substituted propargyl bromides of the Formula XXVII, which are not commercially available can be prepared by those skilled in the art by following procedures well documented in literature. Examples of such procedures include but are not limited to using Sonogoshira reaction of propargyl alcohol with the appropriate halides, followed by conversion of alcohol to bromide [Ref: Tet. Lett 1975, 50, 4467; J. Org. Chem., 1993, 58, 4716; WO 95/24400].

Scheme 5

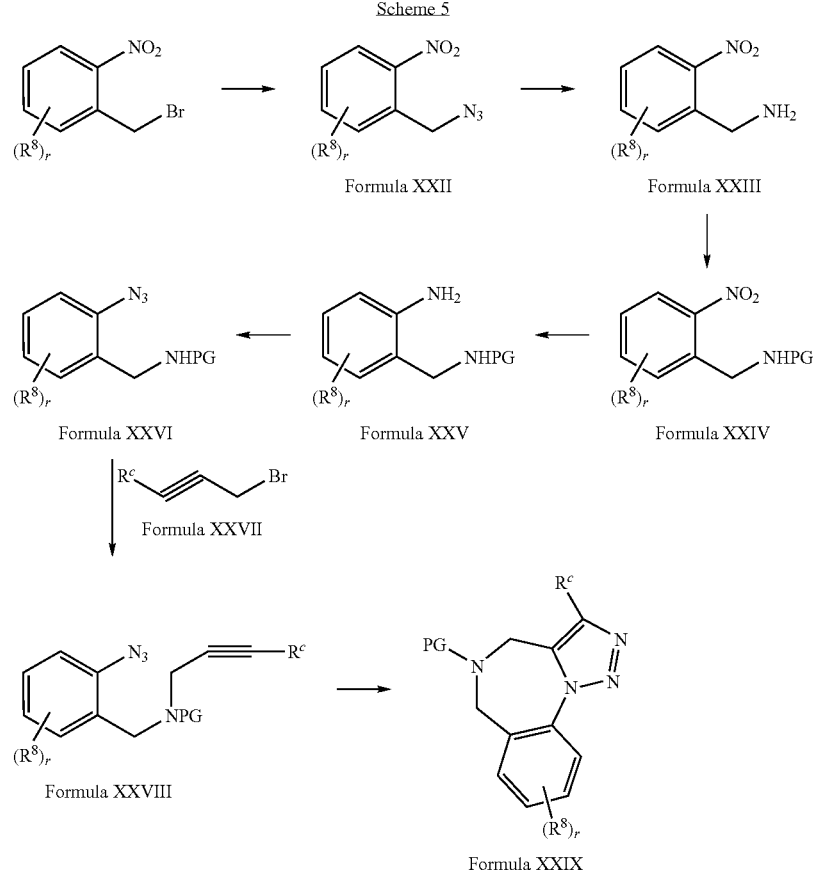

The compounds of Formula XXXI, wherein r, $R^4$, $R^5$ and $R^8$ are as defined herein, can be prepared following the procedure described in Scheme 6, starting from compounds of Formula XVIII which upon reaction with 2-aminoethanol result in the formation of compounds of Formula XXX, wherein r, $R^4$, $R^5$ and $R^8$ are as defined herein. The compounds of Formula XXX are then subjected to Swern Oxidation followed by internal cyclization to give the compounds of Formula XXXI, wherein r, $R^4$, $R^8$ and are as defined herein. [Ref: WO 96/20941, WO 96/23790, EP1183243].

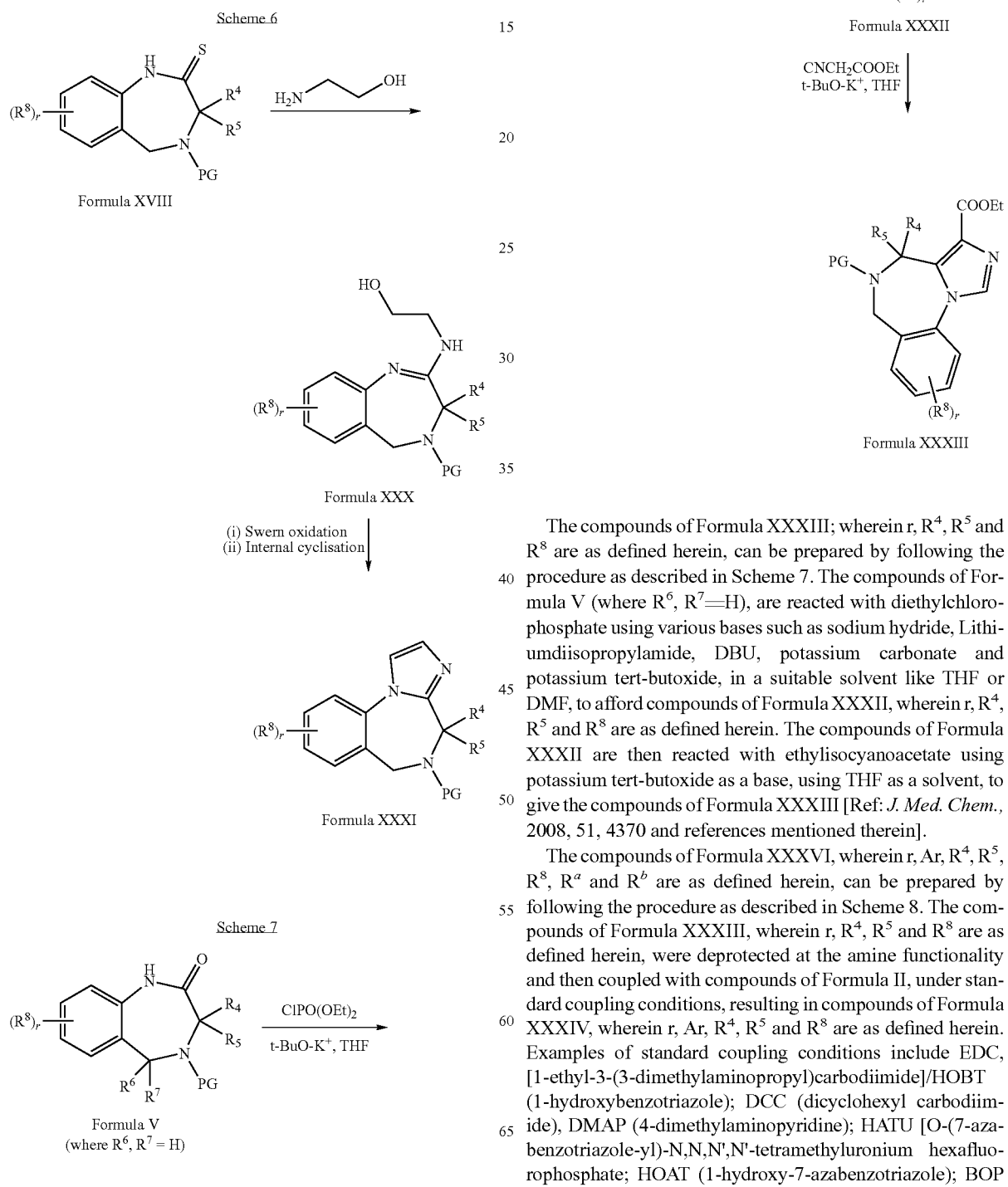
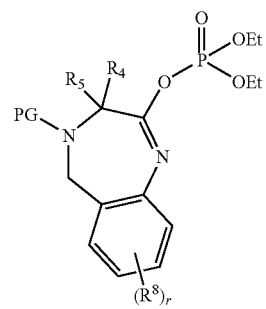
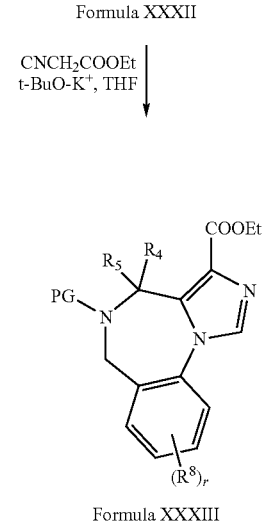

The compounds of Formula XXXIII; wherein r, $R^4$, $R^5$ and $R^8$ are as defined herein, can be prepared by following the procedure as described in Scheme 7. The compounds of Formula V (where $R^6$, $R^7$=H), are reacted with diethylchlorophosphate using various bases such as sodium hydride, Lithiumdiisopropylamide, DBU, potassium carbonate and potassium tert-butoxide, in a suitable solvent like THF or DMF, to afford compounds of Formula XXXII, wherein r, $R^4$, $R^5$ and $R^8$ are as defined herein. The compounds of Formula XXXII are then reacted with ethylisocyanoacetate using potassium tert-butoxide as a base, using THF as a solvent, to give the compounds of Formula XXXIII [Ref: *J. Med. Chem.*, 2008, 51, 4370 and references mentioned therein].

The compounds of Formula XXXVI, wherein r, Ar, $R^4$, $R^5$, $R^8$, $R^a$ and $R^b$ are as defined herein, can be prepared by following the procedure as described in Scheme 8. The compounds of Formula XXXIII, wherein r, $R^4$, $R^5$ and $R^8$ are as defined herein, were deprotected at the amine functionality and then coupled with compounds of Formula II, under standard coupling conditions, resulting in compounds of Formula XXXIV, wherein r, Ar, $R^4$, $R^5$ and $R^8$ are as defined herein. Examples of standard coupling conditions include EDC, [1-ethyl-3-(3-dimethylaminopropyl)carbodiimide]/HOBT (1-hydroxybenzotriazole); DCC (dicyclohexyl carbodiimide), DMAP (4-dimethylaminopyridine); HATU [O-(7-azabenzotriazole-yl)-N,N,N',N'-tetramethyluronium hexafluorophosphate; HOAT (1-hydroxy-7-azabenzotriazole); BOP

[(benzotriazolyl-1-yloxy)-tris(dimethylamine) phosphonium hexafluorophosphate]; mixed anhydride method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like. The compounds of Formula XXXIV were then hydrolysed under basic conditions using appropriate base to give the compounds of Formula XXXV, wherein r, Ar, $R^4$; $R^5$ and $R^8$ are as defined herein, which were further coupled with appropriate amines under standard coupling conditions, resulting in the formation of compounds of Formula XXXVII. Examples of basic hydrolyzing reagents include sodium hydroxide, lithium hydroxide, sodium methoxide and the like, which can be used in appropriate solvents like THF/water, dioxane/water or THF/MeOH/water.

The compounds of Formula XXXIX, wherein r, $R^4$, $R^5$, $R^6$, $R^7$, $R^8$, $R^a$ and $R^b$ are as defined herein, can be prepared by following the procedure as described in Scheme 10. The compounds of Formula XXXVII, wherein $R^1$ is $CH_2COOEt$

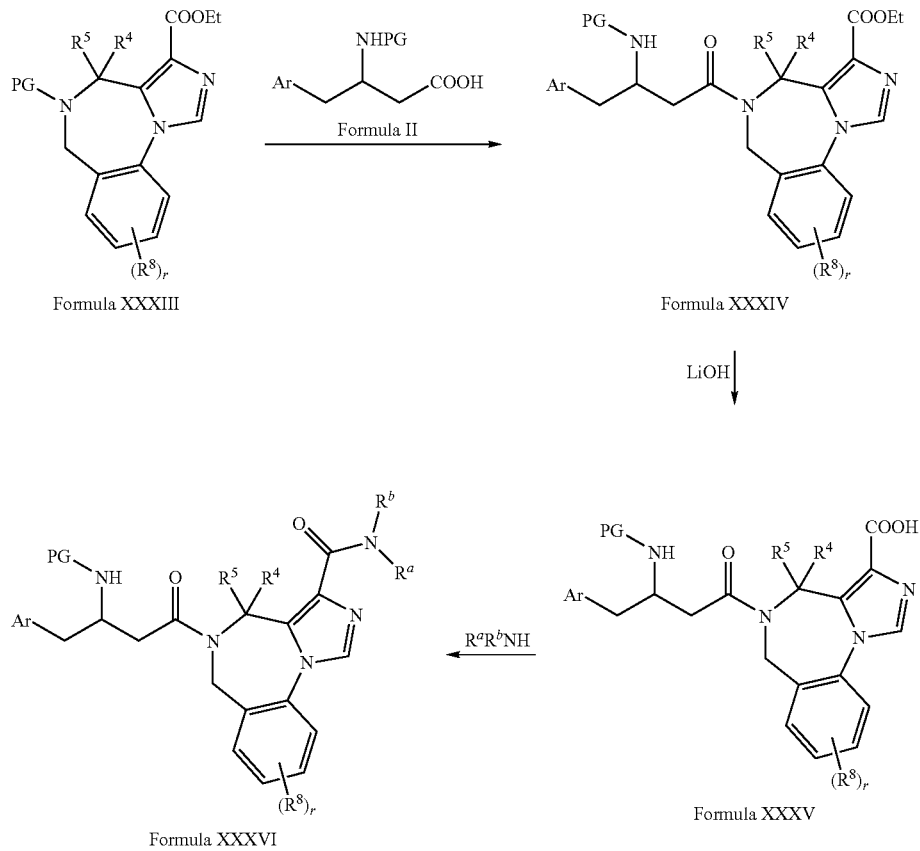

The compounds of Formula XXXVII, wherein r, $R^1$, $R^4$, $R^5$, $R^6$, $R^7$ and $R^8$ are as defined herein, can be prepared from the compounds of Formula V by following the procedure as described in Scheme 9. The compounds of Formula V were N-alkylated at the amide position using appropriate halide in the presence of suitable bases like sodium hydride, potassium carbonate or cesium carbonate, in a suitable polar solvent such as DMF, THF and the like or the mixtures [Ref: US 20060148790 and J. Med. Chem., 2007, 50, 5564].

and r, $R^4$, $R^5$, $R^6$, $R^7$ and $R^8$ are as defined herein, can be hydrolysed under basic conditions to afford the compounds of Formula XXVIII, wherein r, $R^4$, $R^5$, $R^6$, $R^7$ and $R^8$ are as defined herein, which are further coupled to various amines, under standard coupling conditions to provide the compounds of Formula XXXIX. Examples of basic hydrolyzing reagents include sodium hydroxide, lithium hydroxide, sodium methoxide and the like, which can be used in appropriate solvents like THF/water, dioxane/water or THF/

MeOH/water. Examples of standard coupling conditions include EDC [1-ethyl-3-(3-dimethylaminopropyl)carbodiimide]/HOBT (1-hydroxybenzotriazole); DCC (dicyclohexyl carbodiimide), DMAP (4-dimethylaminopyridine); HATU [O-(7-azabenzotriazole-yl)-N,N,N',N'-tetramethyluronium hexafluorophosphate; HOAT (1-hydroxy-7-azabenzotriazole); BOP [(benzotriazolyl-1-yloxy)-tris(dimethylamine) phosphonium hexafluorophosphate]; mixed anhydride method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like.

the like, which can be used in appropriate solvents like THF/water, dioxane/water or THF/MeOH/water. Examples of standard coupling conditions include EDC [1-ethyl-3-(3-dimethylaminopropyl)carbodiimide]/HOBT (1-hydroxybenzotriazole); DCC (dicyclohexyl carbodiimide), DMAP (4-dimethylaminopyridine); HATU [O-(7-azabenzotriazole-yl)-N,N,N',N'-tetramethyluronium hexafluorophosphate; HOAT (1-hydroxy-7-azabenzotriazole); BOP [(benzotriazolyl-1-yloxy)-tris(dimethylamine) phosphonium hexafluorophosphate]; mixed anhydride method using ethyl chloroformate or methyl chloroformate in a suitable solvent such as DMF, DCM, acetonitrile, toluene, THF and the like or mixtures thereof and in the presence of a suitable base such as NMM (N-methylmorpholine), DIPEA (N,N-diisopropylethylamine), triethylamine and the like.

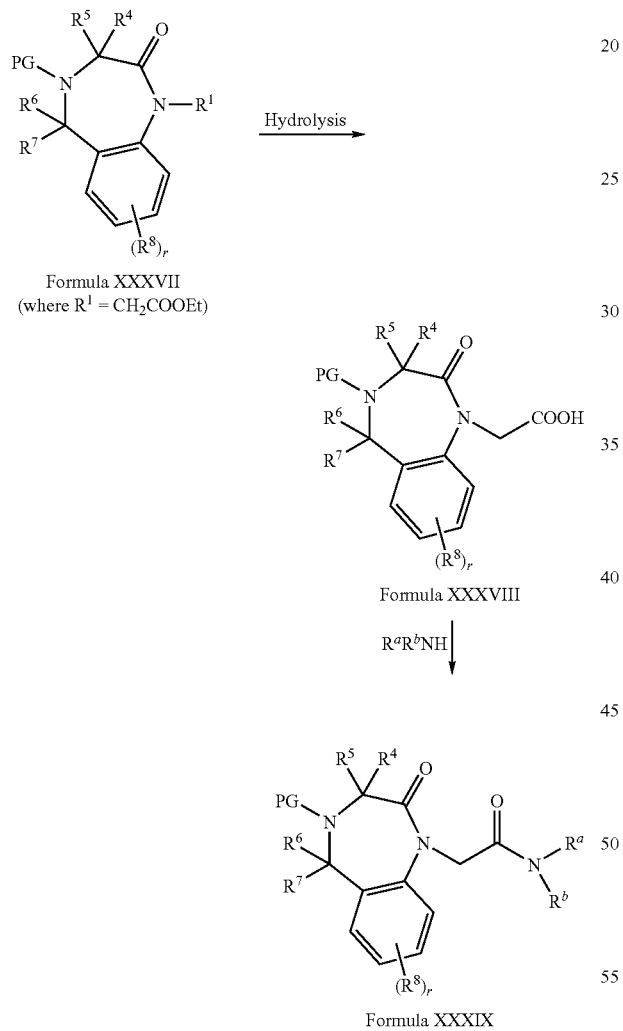

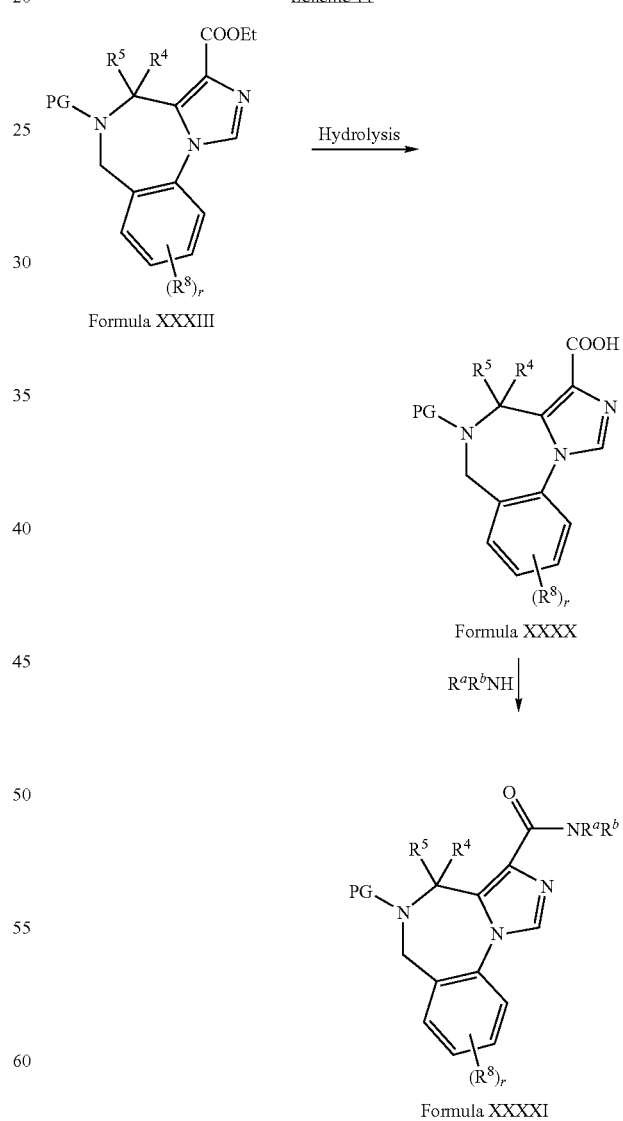

As shown in Scheme 11, the compounds of Formula XXXIII can alternatively be converted to compounds of Formula XXXX, wherein r, $R^4$, $R^5$, and $R^8$ are as defined herein, via basic hydrolysis followed by coupling with the appropriate amine resulting in the formation of compounds of Formula XXXXI, wherein r, $R^4$, $R^5$, $R^8$, $R^a$ and $R^b$ are as defined herein. Examples of basic hydrolyzing reagents include sodium hydroxide, lithium hydroxide, sodium methoxide and Some representative examples of the novel heterocyclic intermediates synthesized using the procedures described in Schemes 1-11, include but are not limited to:

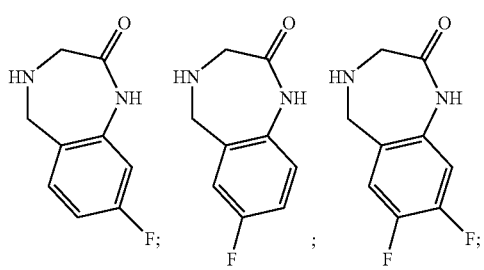
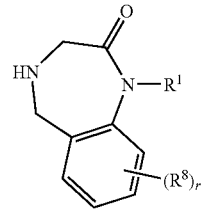
wherein r is 1, 2, 3 or 4
wherein $R^8$ is selected from a group consisting of H, F, Cl and $OCH_3$
wherein $R^1$ is selected from a group consisting of —$CH_3$,
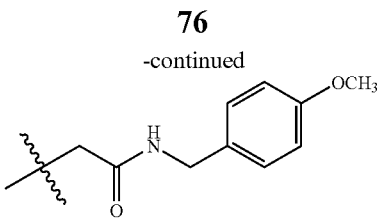
-continued
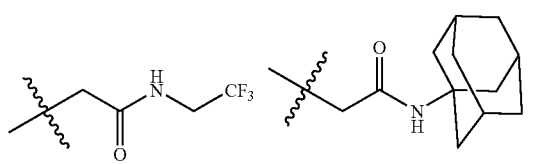
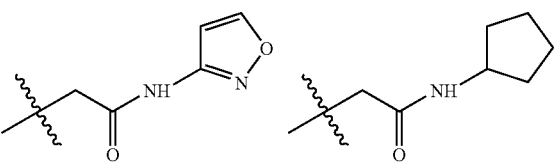
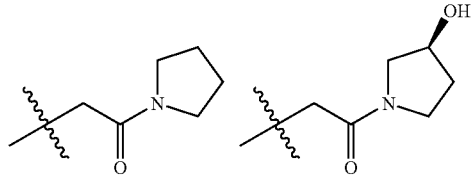
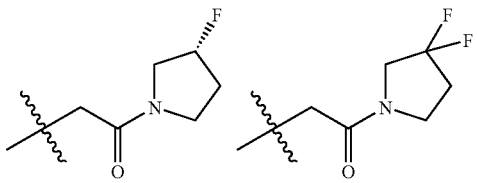
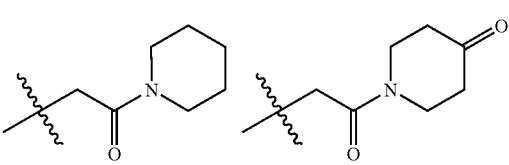
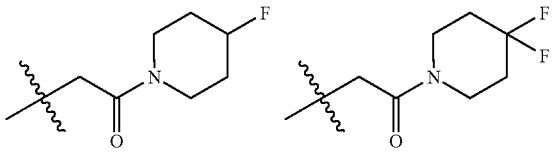
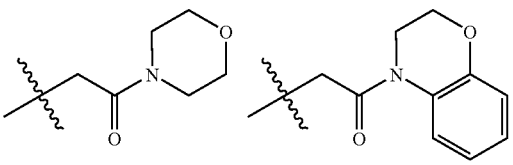
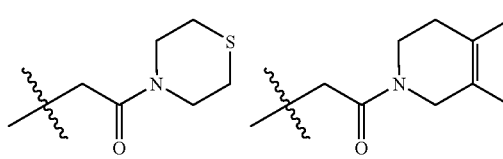
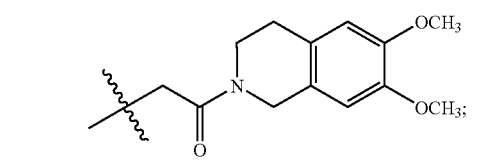

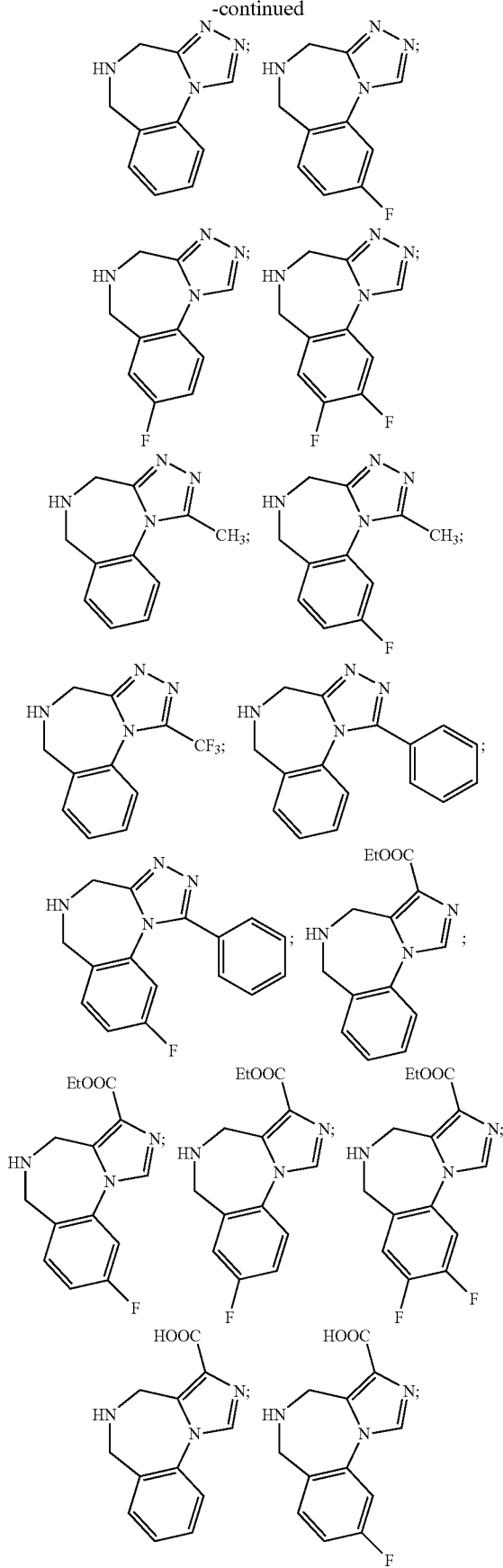
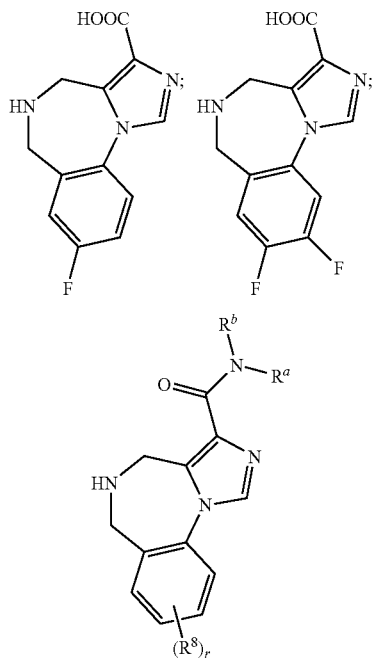
wherein r is 1, 2, 3 or 4
where the moiety
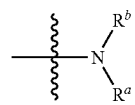
is selected from the group consisting of
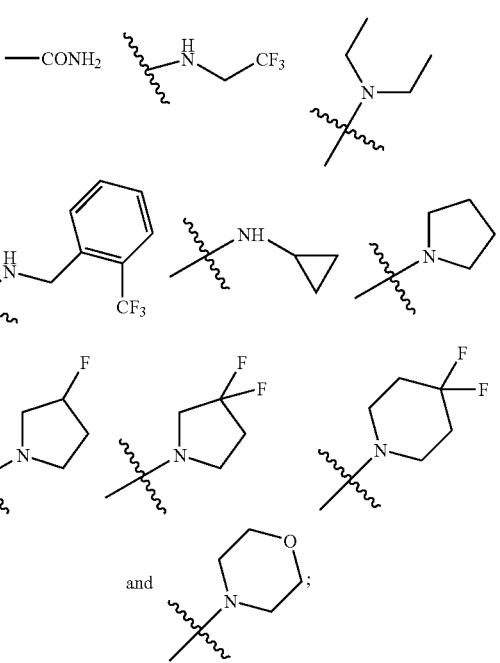

-continued
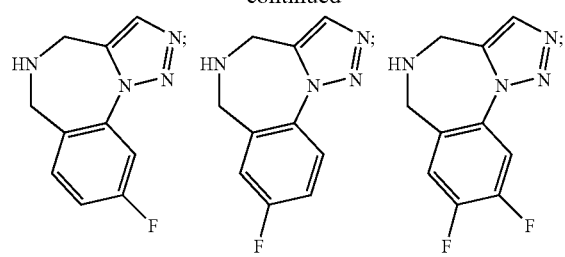
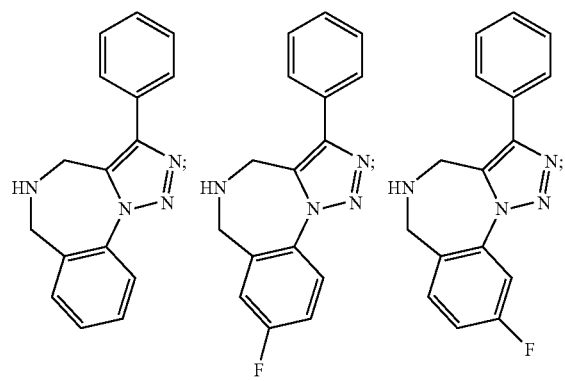
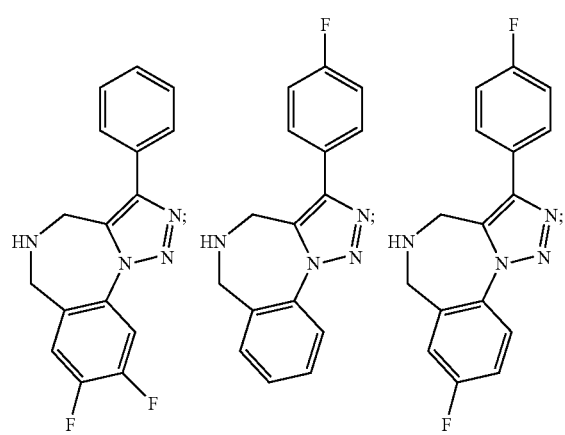
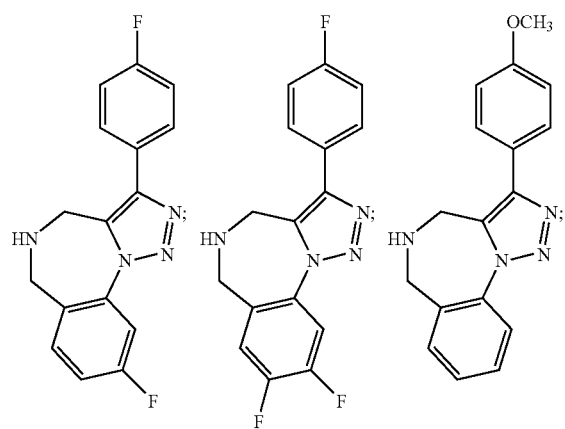
-continued
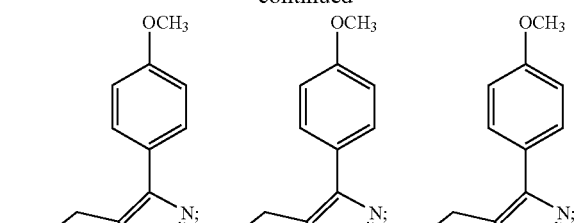
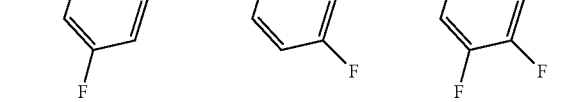
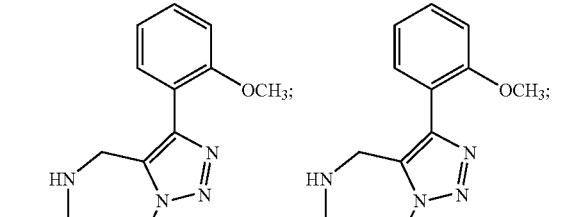
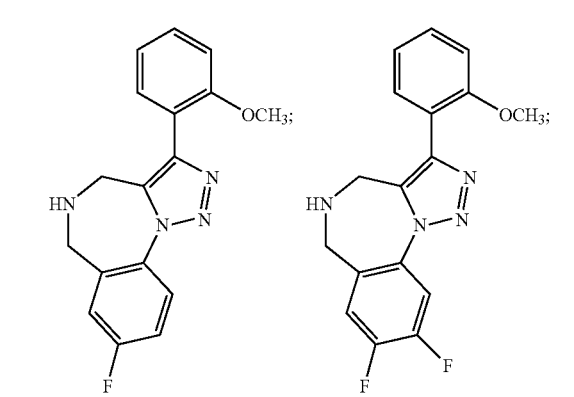
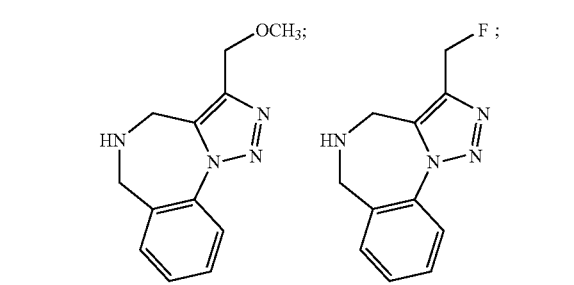

-continued

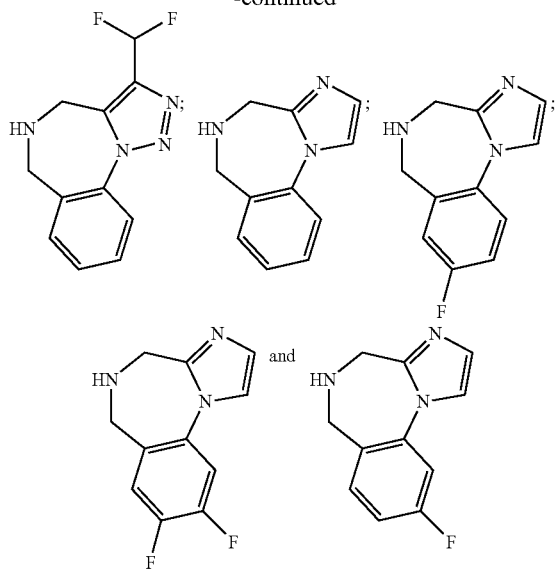

It is understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. The salts may be prepared during the final isolation and purification of the compounds or separately by making basic or acidic addition salts. Representative salts of basic compounds of the present invention can be prepared by reacting free base form of the compound with a suitable acid, including, but not limited to acetate, trifluoroacetate, adipate, citrate, aspartate, benzoate, benzenesulphonate, bisulfate, besylate butyrate, camphorsulphonate, difluconae, hemisulfate, heptanoate, formate, fumarate, lactate, maleate, methanesulfonate, naphthylsulfonate, nicotinate, oxalate, picrate, pivalate, succinate, tartrate, tirchloracetat, glutamate, p-toluenesulphonate, hydrochloric, hydrobromic, sulphuric, phosphoric and the like. Representative salts of acidic compounds of the present invention can be prepared by reacting free acid form of the compound with a suitable base, including, but not limited to ammonium, calcium, magnesium, potassium, sodium salts, salts of primary, secondary and tertiary amines, substituted amines including naturally occurring ones e.g., arginine, betaine, caffeine, choline; glucamine, glucosamine, histidine, lysine, morpholine, piperazine, piperidine, purine, triethylamine and the like. Compounds of the present invention that contain a carboxylic acid (—COOH) or alcohol group, their pharmaceutically acceptable esters of carboxylic acids such as methyl, ethyl and the like, or acyl derivatives of alcohols such as acetate and the like, can be employed. Compounds of the present invention that comprise basic nitrogen atom may be quaternized with alkyl halides, alkyl sulfates and the like. Such salts permit the preparation of both water soluble and oil soluble compounds of the present invention. It should be recognized that the free base or free acid forms will typically differ from their respective salt forms somewhat in physical properties such as solubility in polar solvents, but otherwise the salts are equivalent to their respective free forms for the purpose of the invention.

The "pharmaceutically acceptable solvates" refer to solvates with water hydrates) or pharmaceutically acceptable solvents, for example, ethanol and the like.

The invention also encompasses "prodrugs" of the compounds of the present invention which upon in-vivo administration undergo chemical conversion by metabolic processes before becoming active pharmacological substances. In general such prodrugs will be functional derivatives of a compound of the invention which are readily convertible in vivo into the compound of the invention. Conventional procedures for the selection and preparation of suitable prodrug derivatives are described, for example, in "Targeted prodrug design to optimize drug delivery", *AAPS PharmaSci* (2000), 2(1), E6.

The invention also encompasses active "metabolites" of the compound of the present invention. An active metabolite is an active derivative of a DPP-IV inhibitor produced when the DPP-IV inhibitor is metabolized.

Various "polymorphs" of a compound of general Formula I forming part of this invention may be prepared by crystallization of a compound of Formula I under different conditions. For example, by using different solvents commonly used or their mixtures for recrystallization; crystallizations at different temperatures; various modes of cooling, ranging from very fast to very slow cooling during crystallizations, heating or melting the compound followed by gradual or fast cooling may also obtain polymorphs. The presence of polymorphs may be determined by solid probe NMR spectroscopy, IR spectroscopy, differential scanning calorimetry, powder X-ray diffraction or such other techniques.

The present invention also provides pharmaceutical compositions, comprising compounds of the present invention or their pharmaceutically acceptable derivatives, tautomeric forms, stereoisomers, polymorphs, prodrugs, metabolites, salts or solvates thereof optionally in combination with one or more pharmaceutically acceptable carriers comprising excipients and auxiliaries. The pharmaceutical compositions may be in any form known in the art, such as tablets, capsules, powders, syrups, solutions, suspensions and the like, may contain flavourants, sweeteners etc in suitable solid or liquid carriers or diluents, or in suitable sterile media to form injectable solutions or suspensions. Such compositions typically contain active compound optionally in combination, with pharmaceutically acceptable carriers, diluents or solvents.

The pharmaceutical compositions of the present invention can be manufactured by the processes well known in the art, for example, by means of conventional mixing, dissolving, dry granulation, wet granulation, dragee-making, levigating, emulsifying encapsulating, entrapping, lyophilizing processes or spray drying. The compounds or the pharmaceutical compositions comprising such compounds of the present invention may be administered in the form of any pharmaceutical formulation. The pharmaceutical formulation will depend upon the nature of the active compound and its route of administration. Any route of administration may be used, for example oral, buccal; pulmonary, topical, parenteral (including subcutaneous, intramuscular and intravenous), transdermal, ocular (ophthalmic), by inhalation, intranasal, transmucosal, implant or rectal administration. Preferably the compounds of the present invention are administered orally, parenterally or topically.

In an embodiment, the amount of the novel compounds having the Formula I according to the present invention to be incorporated into the pharmaceutical compositions of the present invention can vary over a wide range depending on known factors such as, for example, the disorder to be treated, the severity of the disorder, the patient's body weight, the dosage form, the chosen route of administration and the number of administration per day. Typically, the amount of the compound of Formula I in the pharmaceutical compositions of the present invention will range from approximately 0.01 mg to about 5000 mg. In an embodiment, the daily dose of composition comprising the novel compounds having the Formula I is in the range of about 0.01 mg/kg to about 100 mg/kg based on the body weight of the subject in need thereof which may be administered as a single or multiple doses.

In an embodiment, the novel compounds having the Formula I according to the present invention are particularly useful for the treatment of disease(s) or disorder(s) which are particularly acute in nature and which require a short term but mild to moderate treatment, or even some chronic conditions which favorably respond to or are alleviated by the novel compounds having the Formula or compositions comprising them. The compositions comprising the novel compounds having the Formula I are useful prophylactically or therapeutically depending upon the pathological condition intended to be prevented or treated respectively.

The DPP-IV inhibitors of the present invention are useful for the prophylaxis, amelioration and/or treatment of Type 2 diabetes and in the prophylaxis, amelioration and/or treatment of the numerous conditions that often accompany Type 2 diabetes. The diseases, disorders and conditions that are related to Type 2 Diabetes and therefore may be treated, controlled in some cases prevented, by treatment with DPP-IV inhibitors include, but not limited to, for example, hyperglycemia and Metabolic Syndrome or 'Syndrome X', including impaired glucose tolerance, insulin resistance, metabolic acidosis or ketosis, disorders of food intake, satiety disorders, obesity, dyslipidemia (including hyperlipidemia, hypertriglyceridemia, hypercholesterolemia, low HDL levels, high LDL levels), atherosclerosis and its 30 sequele, hypertension associated with metabolic disorders.

Other inflammatory conditions, include but are not limited to, for example, irritable bowel disease(IBS), inflammatory bowel disease including Crohn's disease and ulcerative colitis, pancreatitis, neurodegenerative disease, retinopathy, nephropathy, neuropathy, ovarian hyperandrogenism (polycystic ovarian syndrome) and other disorders where insulin resistance is a component.

Furthermore, the compounds of the present invention may also be useful for the prophylaxis, amelioration and/or treatment of wound healing, tissue ischemia, cataracts, glaucoma, increased cardiovascular risk, growth hormone deficiency, neutropia, neuronal disorders, tumor invasion and metastasis, benign prostatic hypertrophy (BPH), gingivitis, osteoporosis, sperm motility/male contraception, pain, neuropathic pain, rheumatoid pain, osteoarthritis pain, acne, skin disorders (e.g. pigmentation disorders or psoriasis), anxiety, anorexia, epilepsy, male and female sexual dysfunction, major depression disorder, Parkinson's disease, migraine, osteoarthritis, immunosuppression, HIV infection, hematopoiesis, anemia and other conditions manifested by a variety of metabolic, neurological, anti-inflammatory, and autoimmune disorders including, for example, rheumatoid arthritis, viral, cancer and gastrointestinal disorders that may be prevented or treated by inhibition of DPP-IV.

A further embodiment of the present invention is the use of a compound of Formula I for the manufacture of a medicament for the prophylaxis, amelioration and/or treatment of one or more one or more condition(s)/disease(s)/disorder(s) mediated by DPP-IV in a subject in need thereof.

Another embodiment of the present invention provides methods for the prophylaxis, amelioration and/or treatment of one or more one or more condition(s)/disease(s)/disorder(s) mediated by DPP-IV in a subject in need thereof that comprises administering a therapeutically effective amount of compound of Formula I.

In still another embodiment of the present invention is provided use of the dosage form compositions comprising the novel compounds of Formula I for the treatment of one or more condition(s)/disease(s)/disorder(s) mediated by DPP-IV which comprises administrating to a subject in need thereof a pharmaceutically effective amount of the composition.

In yet another embodiment, the compounds of the present invention are useful in the treatment of the aforementioned diseases, disorders and conditions in combination with another disease modifying drug. The compounds of the present invention may be used in combination with one or more other drugs in the treatment, prevention, suppression or amelioration of diseases or conditions for which compounds of Formula I or other drugs may have utility, where the combination of the drugs together are safer or more effective than either drug alone.

Other therapeutic agents suitable for combination with the compounds of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents, anti-TNF agent or c-AMP raising agents and appetite suppressants.

Examples of suitable anti-diabetic agents for use in combination with the compounds of the present invention include but are not limited to (a) other DPP-IV inhibitors such as Sitagliptin(Merck), Vildagliptin (Novartis); (b) insulin sensitizers including (i) PPAR γ agonists such as the glitazones (e.g. pioglitazone, rosiglitazone and the like) and other PPAR ligands, including PPAR α/γ dual agonists and PPAR α agonists such as fenofibric acid derivatives (gemfibrozil, clofibrate, fenofibrate and bezafibrate, (ii) biguanides such as metformin and phenformin, and (iii) protein tyrosine phosphatase-1B (PTP-1B) inhibitors; (c) insulin or insulin mimetics; (d) sulfonylureas and other insulin secretagogues, such as tolbutamide, glyburide, glipizide, glimepiride, and meglitinides, such as repaglinide; (e) alpha.-glucosidase inhibitors (such as acarbose and miglitol); (f) glucagon receptor antagonists; (g) GLP-1, GLP-1 mimetics such as exendin-4 or amylin and GLP-1 receptor agonists (h) GIP and GIP mimetics (i) PACAP, PACAP mimetics, and PACAP receptor agonists; (j) AMPK activators; (k) 11β-HSD inhibitors; (l) SGLT-2 inhibitors; (m) inhibitors of glucose-6-phosphate, fructose-1,6-biphosphate, glycogen phosphorylase, aminopeptidase-N or pyruvate dehydrokinase; (n) glucokinase activators (GKAs).

It is believed that the use of the compounds of Formula I in combination with at least one or more other anti-diabetic agent(s) provides anti-hyperglycemic results greater than that possible from each of these medicaments alone or greater than the combined additive anti-hyperglycemic effects produced by these medicaments.

Examples of suitable hypolipidemic/lipid lowering agents for use in combination with the compounds of the present invention include but are not limited to (a) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol; nicotinic acid or a salt thereof, (iv) PPAR agonists as described herein, (vi) inhibitors of cholesterol absorption, such as beta-sitosterol and ezetimibe, (vii) acyl CoA cholesterol acyltransferase inhibitors, such as avasimibe, and (viii) anti-oxidants, such as probucol; (b) ileal bile acid transporter inhibitors; (c) HDL raising compounds such as CETP inhibitors (d) lipoxygenase inhibitors; (e) ACAT inhibitors such as avasimibe; (f) fibric acid derivatives; (g) MTP inhibitors.

Examples of suitable anti-obesity compounds for use in combination with the compounds of the present invention include but are not limited to (a) fenfluramine, dexfenfluramine, phenteimine; sibutramine, orlistat and the like; (b) neuropeptide $Y_1$ or $Y_5$ antagonists; (c) CB-1 receptor inverse agonists and antagonists; (d) $\beta_3$ adrenergic receptor agonists; (e) melanocortin receptor agonists, in particular melanocortin-4 receptor agonists; (f) ghrelin antagonists; (g) melanin-concentrating hormone (MCH) receptor antagonists;

Examples of suitable anti-hypertensive agents for use in combination with the compounds of the present invention include but are not limited to (a) vasopeptidase inhibitors like Neutral endopeptidase (neprilysin) inhibitors and/or ACE inhibitors or dual NEP/ACE inhibitors (enalapril, lisinopril; captopril, quinapril, tandolapril); (b) beta blockers and calcium channel blockers; (c) A-II receptor blockers (losaitan, candesartan, irbesartan, valsartan, telmisartan, eprosartan); (d) Renin inhibitors e.g., aliskiren.

Examples of suitable anti-inflammatory agents for use in combination with the compounds of the present invention include but are not limited to aspirin, non-steroidal anti-inflammatory drugs, glucocorticoids, azulfidine, and selective cyclooxygenase-2 inhibitors.

EXAMPLES

The invention is explained in detail in the following examples which are given solely for the purpose of illustration only and therefore should not be construed to limit the scope of the invention. All of the starting materials are either commercially available or can be prepared by procedures that would be well known to one of ordinary skill in organic chemistry. Solvents were dried prior to use wherever necessary by standard methods (Perrin, D. D.; Armarego, W. L. F. Purification of Laboratory Chemicals, Pergamon Press: Oxford, 1988). Mass spectra (MS) were obtained by electron spray ionization (ESI) eV using Applied biosystem 4000 Q TRAP. $^1$H NMR were recorded on Bruker 400 MHz Avance II NMR spectrometer. Chemical shifts are reported as δ values in parts per million (ppm), relative to TMS as internal standard. All coupling constants (J) values are given in Hz.

ABBREVIATIONS

The following abbreviations are employed in the examples and elsewhere herein:

| | |
|---|---|
| $^1$H NMR | Proton nuclear magnetic resonance |
| Bn | benzyl |
| BOP | (benzotriazolyl-1-yloxy)-tris(dimethylamine) phosphonium hexafluorophosphate |
| (Boc)$_2$O | di-tert-butyl dicarbonate |
| bs | Broad singlet |
| C | centigrade |
| CDCl$_3$ | deuterated chloroform |
| CHCl$_3$ | chloroform |
| cm | centimeter |
| DCM | dichloromethane |
| dd | doublet of doublet |
| DIPEA | diisopropylethylamine |
| DMF | dimethylformamide |
| DMSO | dimethylsulfoxide |
| EDC | N-(3-dimethylaminopropyl)-N-ethylcarbodiiimide hydrochloride |
| ESIMS | electron spray ionization mass Spectroscopy |
| EtOAc | ethylacetate |
| EtOH | ethanol |
| g | gram(s) |
| h | hour(s) |
| HOBT | 1-hydroxybenzotriazole |
| HPLC | High performance liquid chromatography |
| Hz | Hertz |
| J | moupling constant |
| m | multiplet |
| MeOH | methanol |
| mg | milligram |
| min | minutes |
| mL | milliliter |
| mmol | millimoles |
| mp | melting point |
| Na$_2$SO$_4$ | sodium sulphate |
| NaHCO$_3$ | sodium bicarbonate |
| n-BuLi | n-Butyl lithium |
| NMR | Nuclear magnetic resonance |
| Pd/C | Palladium on carbon |
| Pet. ether | Petroleum ether |
| PG | Protecting Group |
| Piv | pivaloyl |
| ppm | parts per million |
| Py | pyridine |
| q | quartet |
| r.t. | room temperature |
| s | singlet |
| t | triplet |
| TFA | trifluoroacetic acid |
| THF | tetrahydrofuran |
| TLC | Thin layer chromatography |
| µg | microgram |

Example 1

Preparation of trifluoroacetic acid salt of 4-[(R)-3-amino-4-(2,4,5-trifluorophenyl)-butyryl]-1,3,4,5-tetrahydro-benzo[e][1,4]diazepin-2-one

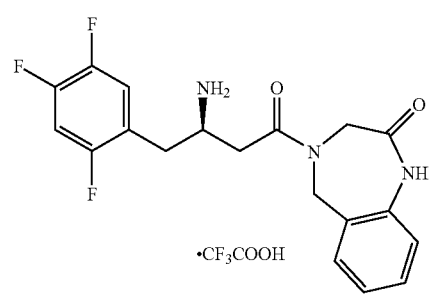 [SMILES: N[C@@H](CC(=O)N1CC(=O)Nc2ccccc2C1)Cc1cc(F)c(F)cc1F ; "·CF3COOH"]

Step 1: Preparation of (2-nitro-benzylamino)-acetic acid methyl ester

To a solution of 2-nitrobenzyl bromide (1.0 g, 4.63 mmol) and glycine methyl ester hydrochloride (868 mg, 6.94 mmol) in dry DMF (10 mL), was added DIPEA (2.42 mL, 13.89 mmol) under nitrogen atmosphere. The reaction mixture was stirred at. r.t. overnight. After completion of the reaction as confirmed by TLC, water (50 mL) was added to the reaction mixture. The crude product was extracted with ethyl acetate (20 mL). The aqueous layer was washed with ethyl acetate (2×10 mL), The combined organic extract was dried over $Na_2SO_4$ and the solvents were removed in vacuo to afford the crude compound, which was purified by column chromatography (silica gel, 1:9 EtOAc:Pet Ether) to afford pure (2-nitro-benzylamino)-acetic acid methyl ester (765 mg 73%) as a viscous oil.

ESIMS (m/z): 224.7 (M+1)

Step 2: Preparation of [tert-Butoxycarbonyl-(2-nitro-benzyl)-amino]-acetic acid methyl-ester To a solution of (2-nitro-benzylamino)-acetic acid methyl ester (760 mg, 3.39 mmol) in dry DCM (20 mL), was added di-tert-butyl dicarbonate (1.11 g, 5.08 mmol) and the reaction was stirred at r.t. overnight. After completion of the reaction as confirmed by TLC, solvent was removed in vacuo to afford the crude compound, which was purified by column chromatography (silica gel, 2:8 EtOAC:Pet Ether) to afford pure [tert-butoxycarbonyl-(2-nitro-benzyl)-amino]-acetic acid methyl ester (850 mg, 77%) as a viscous oil.

ESIMS (m/z): 346.8 (M+Na), 325.1 (M+1)

Step 3: Preparation of [(2-amino-benzyl)-tert-butoxycarbonyl-amino]-acetic acid methyl ester To a solution of tert-butoxycarbonyl-(2-nitro benzyl)-amino]-acetic acid methyl ester (845 mg, 2.61 mmol) in MeOH (15 mL), was added 10% Pd/C (84.5 mg, 10% by weight) under nitrogen atmosphere. The reaction mixture was evacuated and then charged with hydrogen gas and hydrogenated using hydrogen balloon for 3 h. After completion of the reaction as confirmed by TLC, the reaction mixture was evacuated and brought under nitrogen atmosphere and then filtered through celite bed, washed with MeOH (10 mL). The filtrate was concentrated in vacuo to afford [(2-amino-benzyl)-tert-butoxycarbonyl-amino]-acetic acid methyl ester (660 mg, 86%) as a yellow oil which was used as such without any further purification for the next step.

ESIMS (m/z): 295.4 (M+1)

Step 4: Preparation of 2-oxo-1,2,3,5-tetrahydro-benzo[e][1,4]diazepine-4-carboxylic acid tert-butyl ester To a solution of [(2-amino-benzyl)-tert-butoxycarbonyl-amino]acetic acid methyl ester (640 mg, 2.18 mmol) in toluene (30 mL), was added HOBT (177 mg, 1.31 mmol). The reaction mixture was heated at 100° C. for 24 h. After the completion of reaction, as confirmed by TLC, the solvent was removed in vacuo to afford the crude compound, which was purified by column chromatography (silica gel, 7:13 EtOAc: Pet. Ether) to afford pure 2-oxo-1,2,3,5-tetrahydro-benzo[e][1,4]diazepine-4-carboxylic acid tert-butyl ester: (350 mg, 61%) as a solid.

ESIMS (m/z): 263.3 (M+1)

Step 5: Preparation of trifluoroacetic acid salt of 1,3,4,5-tetrahydro-benzo[e][1,4]diazepin-2-one To a solution of 2-oxo-1,2,3,5-tetrahydro-benzo[e][1,4]diazepine-4-carboxylic acid tert-butyl ester (300 mg, 1.14 mmol) in dry DCM (10 mL) was added trifluoroacetic acid (3.42 mL, 3 mL/mmol). The reaction mixture was stirred at r.t. for 2 h. After completion of the reaction as confirmed by TLC, excess of trifluoroacetic acid and DCM were removed under vacuo to afford trifluoroacetic acid salt of 1,3,4,5-tetrahydro-benzo[e][1,4]diazepin-2-one (295 mg, 93%) as a gummy solid. The crude compound was used as such without further purification for the next step.

ESIMS (m/z): 185.3 (M+Na), 163.3 (M+1)

Step 6: Preparation of [(R)-3-oxo-3-(2-oxo-4,2,3,5-tetrahydro-benzo[e][1,4]diazepin-4-yl)-1-(2,4,5-trifluoro-benzyl)-propyl]-carbamic acid tert-butyl ester To a solution of (R)-3-[(tert-butoxycarbonyl)amino]-4-(2, 4,5-trifluorophenyl)butanoic acid (90 mg, 0.26 mmol) in dry DCM (10 mL), was added HOBT (47 mg, 0.34 mmol), EDC (67 mg, 0.34 mmol) and DIPEA (0.24 mL, 1.35 mmol). The reaction mixture was stirred at r.t. for 10 min. A solution of 1,3,4,5-Tetrahydro-benzo[e][1,4]diazepin-2-one trifluoroacetate (74 mg, 0.26 mmol) in dry DCM (5 mL) was added and the reaction mixture was stirred at r.t. overnight under nitrogen atmosphere. After the completion of the reaction, as confirmed by TLC, the crude product was extracted with DCM (10 mL) and washed sequentially with 10% HCl solution (10 mL) and saturated sodium bicarbonate solution (10 mL). The organic layer was separated, washed with water, dried over $Na_2SO_4$ and concentrated in vacuo to afford the crude compound, which was purified by column chromatography (silica gel, 2:3 EtOAc:Pet.Ether) to afford [(R)-3-Oxo-3-(2-oxo-1,2,3,5-tetrahydro-benzo[e][1,4]diazepin-4-yl)-1-(2,4,5-trifluoro-benzyl)-propyl]-carbamic acid tert-butyl ester (80 mg, 62%) as a white solid.

ESIMS (m/z): 500.2 (M+Na); 478.2 (M+1)

Step 7: Preparation of trifluoroacetic acid salt of (R)-4-[3-Amino-4-(2,4,5-trifluorophenyl)-butyryl]-1,3,4,5-tetrahydro-benzo[e][1,4]diazepin-2-one To a solution of [(R)-3-oxo-3-(2-oxo-1,2,3,5-tetrahydro-benzo[e][1,4]diazepin-4-yl)-1-(2,4,5-trifluoro-benzyl)-propyl]-carbamic acid tert-butyl ester (40 mg, 0.08 mmol) in DCM (5 mL), was added trifluoroacetic acid (0.24 mL, 3 mL/mmol). The reaction mixture was stirred at r.t. for 1 h. After completion of the reaction, as confirmed by TLC, excess of trifluoroacetic acid and DCM were evaporated in vacuo to afford a gummy solid which was solidified from hexane to afford trifluoroacetic acid salt of 4-[(R)-3-amino-4-(2,4,5-trifluorophenyl)-butyryl]-1,3,4,5-tetrahydro-benzo[e][1,4]diazepin-2-one (30 Mg, 73%) as a solid.

$^1$H NMR (400 MHz, MeOD): δ2.62-2.70 (m, 1H), 2.75-2.87 (m, 1H), 2.97-3.03 (m, 2H), 3.76-3.86 (two m, 1H), 4.17 (s, 1H), 4.50 (s, 1H), 4.62 (s, 1H), 4.66 (s; 1H), 7.05-7.15 (m, 2H), 7.14-7.25 (m, 2H), 7.27-7.30 (m, 2H)

ESIMS (m/z): 400.3 (M+Na), 378.2 (M+1)

Example 2

Preparation of trifluoroacetic acid salt of (R)-4-(3-amino-4-(2,4,5-trifluorophenyl)butanoyl)-7,8-difluoro-4,5-dihydro-1H-benzo[e][1,4]diazepin-2(3H)-one

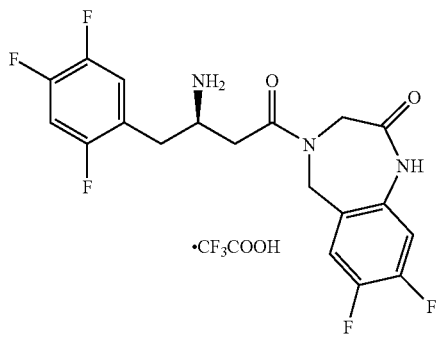 [SMILES: N[C@@H](CC(=O)N1CC(=O)Nc2cc(F)c(F)cc2C1)Cc1cc(F)c(F)cc1F ; "·CF3COOH"]

Step 1: Preparation of 2-amino-4,5-difluoro-phenyl-methanol

To a solution of lithium aluminium hydride (2.13 g, 57.76 mmol) in dry THF (35 mL) at 0° C., was slowly added a solution of 2-amino-4,5-difluoro benzoic acid (5 g, 28.88 mmol) dissolved in dry THF (35 mL). The reaction was stirred at r.t. for 2 h. After completion of the reaction as confirmed by TLC, water (2.1 mL), 10% NaOH (2.1 mL) and water (3×2.1 mL) were added sequentially to the reaction mixture at 0° C. The resultant slurry was stirred at r.t. for 20 min. The slurry was filtered from celite bed and washed with EtOAc (2×20 mL). The filtrate was dried over $Na_2SO_4$ and the solvents were removed in vacuo to afford the crude compound as a solid. The crude compound, (2-amino-4,5-difluoro-phenyl)-methanol (4.50 g, 98%) was used as such without any further purification for the next step.

ESIMS (m/z): 158.1 (M−1)

Step 2: Preparation of tert-butyl 4,5-difluoro-2-hydroxymethyl)phenylcarbamate To a solution of (2-amino-4,5-difluoro-phenyl)-methanol (4.50 g, 28.30 mmol) in 1,4-dioxane and Water (1:1, 50 mL) was added $NaHCO_3$ (4.7 g, 56.60 mmol) at 0° C. To the resulting solution, was added di-tert-butyl dicarbonate (9.7 mL, 42.45 mmol). The reaction was stirred at r.t. for 10 h. After completion of the reaction, as confirmed by TLC, 1,4-dioxane was removed in vacuo and crude compound was extracted with EtOAc (3×50 mL). The combined organic layers were dried over $Na_2SO_4$ and the solvents were removed in vacuo to afford the crude compound, which was purified by column chromatography (silica gel, 1:9 EtOAc:Pet. Ether) to afford pure (4,5-difluoro-2-hydroxymethyl-phenyl)-carbamic-acid tert-butyl ester (5.86 g, 80%) as a thick gel.

ESIMS (m/z): 258.3 (M−1)

Step 3: Preparation of tert-butyl 2-(chloromethyl)-4,5-difluorophenylcarbamate To a solution of (4,5-difluoro-2-hydroxymethyl-phenyl)-carbamic acid tent-butyl ester (5.86 g, 22.62 mmol) in dry DCM (50 mL) was added thionyl chloride (3.28 mL, 45.64 mmol) at 0° C. The reaction was stirred at r.t. for 2 h under argon. After completion of the reaction as confirmed by TLC, water (30 mL) was added to the reaction mixture and crude compound was extracted with DCM (3×30 mL). The combined organic layers were dried over $Na_2SO_4$, and the solvents were removed in vacuo to afford the crude (2-chloromethyl-4,5-difluoro-phenyl)carbamic acid tert-butyl ester (5.65 g, 90%) which was used as such without any further purification for the next step.

ESIMS (m/z): 279.3 (M+1)

Step 4: Preparation of (2-tert-butoxycarbonylamino-4,5 difluoro-benzylamino)-acetic acid methyl ester To a solution of (2-chloromethyl-4,5-difluoro-phenyl)-carbamic acid tert-butyl ester) (5.65 g, 20.3 mmol) in DMF (50 mL) was added DIPEA (10.6 mL, 60.9 mmol). The resulting solution was stirred for 5 min, followed by dropwise addition of solution of glycine methyl ester hydrochloride in DMF at 0° C. The reaction mixture was stirred overnight at 50° C. After completion of the reaction as confirmed by TLC, water (60 mL) was added to the reaction mixture and crude compound was extracted with EtOAc (3×50 mL). The combined organic layers were dried over $Na_2SO_4$. The solvents were removed in vacuo to afford the crude compound which was purified by column chromatography (silica gel: 1.5:8.5 EtOAc:Pet. ether) to obtain pure (2-tert-butoxycarbonylamino-4,5 difluoro-benzylamino)-acetic acid methyl ester (5.37 g, 80%) as thick gel.

ESIMS (m/z): 331.4 (M+1)

Step 5: Preparation of benzyloxy carbonyl-(2-tert-butoxycarbonylamino 4,5-difluoro-benzyl)-amino]-acetic acid methyl ester To a solution of (2-tert-butoxycarbonylamino-4,5 difluoro-benzylamino)-acetic acid methyl ester (5.37 g, 16.28 mmol) in 1,4-dioxane: water (1:1, 50 mL) was added $NaHCO_3$ (2.73 g, 32.56 mmol) at 0° C., followed by the addition of benzyl chloroformate (4.09 mL, 24.42 mmol). The reaction was stirred at r.t. for 10 h. After completion of the reaction as confirmed by TLC, 1,4-dioxane was removed in vacuo and crude compound was extracted with EtOAC (3×50 mL). The combined organic layers were dried over $Na_2SO_4$ and the solvents were removed in vacuo to afford the crude compound, which was purified by column chromatography (silica gel, 1.5:8.5 EtOAc:Pet. ether) to afford pure [benzyloxy carbonyl-(2-tert-butoxycarbonylamino-4,5-defluoro-benzyl)-amino]-acetic acid methyl ester (5.28 g, 70%) as thick gel.

ESIMS (m/z): 463.4 (M−1)

Step 6: Preparation of benzyloxy carbonyl-(2-tert-butoxycarbonylamino-4,5-difluoro-benzyl)-amino]-acetic acid To a solution of benzyloxy carbonyl-(2-tert-butoxycarbonylamino-4,5-difluoro-benzyl)-amino]-acetic acid methyl ester (5.28 g, 11.39 mmol) in THF (30 mL) was added a solution of lithium hydroxide (2.87 g, 68.34 mmol) in water (10 mL). The reaction was stirred at r.t. for 10 h. After completion of the reaction as confirmed by TLC, the reaction mixture was acidified to pH 4 by adding 10% HCl and crude compound was extracted with EtOAc (3×50 mL). The combined organic layers were dried over $Na_2SO_4$ and the solvents were removed in vacuo to afford the crude compound [benzyloxy carbonyl-(2-tert-butoxycarbonylamino-4,5-difluoro-benzyl)-amino]acetic acid (4.76 g, 93%) as a solid, which was used as such without any further purification for the next step.
ESIMS (m/z): 448.8 (M−1)

Step 7: Preparation of 2-[(benzyloxycarbonyl-carboxymethyl-amino)-methyl]-4,5-difluoro-phenyl-ammonium trifluoroacetate To a solution of {benzyloxy carbonyl-(2-tert-butoxycarbonylamino-4,5-difluoro-benzyl)-amino]-acetic acid} (4.76 g, 10.56 mmol) in dry DCM (40 mL) was added trifluoroacetic acid (14.35 mL, 3 mL/mmol) at 0° C. The reaction mixture was stirred at r.t. for 2 h under argon. After completion of the reaction as confirmed by TLC, the reaction mixture was evaporated in vacuo to remove excess of solvent and trifluoroacetic acid. The remaining were removed under vacuo and 2-[(benzyloxycarbonyl-carboxymethyl-amino)-methyl]-4,5-difluoro, phenyl-ammonium trifluoroacetate (4.75 g, 97%) was obtained as thick brown jelly which was used as such without any further purification for the next step.
ESIMS (m/z): 351.2 (M+1)

Step 8: Preparation of benzyl 7,8-difluoro-2-oxo-2,3-dihydro-1H-benzo[e][1,4]diazepine-4(5H)-carboxylate To a solution of 2-[(benzyloxycarbonyl-carboxymethyl-amino)-methyl]-4,5-difluoro-phenyl-ammonium trifluoroacetate (4.75 g, 10.25 mmol) in DCM (40 mL) was added EDC (2.55 g, 13.32 mmol) and HOBT (1.7.9 g, 13.32 mmol) at 0° C. The resulting solution was stirred for 5 min and DIPEA (5.35 mL, 30.75 mmol) was added to it. The reaction mixture was stirred overnight at r.t. under argon. After completion of the reaction as confirmed by TLC, water (60 mL) was added to the reaction mixture and crude compound was extracted with DCM (3×50 mL). The combined organic layers were dried over $Na_2SO_4$ and the solvents were removed in vacuo to afford the crude compound which was purified by column chromatography (silica gel: 2:8 EtOAc:Pet. ether) to afford pure benzyl 7,8-difluoro-2-oxo-2,3-dihydro-1H-benzo[e][1,4]diazepine-4(5H)-carboxylate (2.04 g, 60%) as thick gel.
ESIMS (m/z): 331.2 (M−1)

Step 9: Preparation of 7,8-difluoro-1,3,4,5-tetrahydro-benzo[e][1,4]diazepin-2-one To a solution of (7,8-difluoro-2-oxo-1,2,3,5-tetrahydro-benzo[e][1,4]diazepine-4-carboxylic acid phenyl ester) (2.64 g, 6.15 mmol) in MeOH (30 mL), was added 10% Pd/C (200 mg, 20% w/w) under argon; The reaction was stirred at r.t. for 5 h under hydrogen atmosphere. After completion of the reaction as confirmed by TLC, the reaction mixture was filtered through celite bed and washings were given with EtOAc and MeOH. The solvents were removed in vacuo to afford the crude compound which was purified by column chromatography (silica gel: 1:9 MeOH:$CHCl_3$) to afford pure 7,8-difluoro-1,3,4,5-tetrahydro-benzo[e][1,4]diazepin-2-one as off white solid (0.98 g, 80%).
ESIMS (m/z): 199.7 (M+1)

Step 10: Preparation of (R)-tert-butyl 4-(7,8-difluoro-2-oxo-2,3-dihydro-1H-benzo[e][1,4]diazepin-4(5H)-yl)-4-oxo-1-(2,4,5-trifluorophenyl)butan-2-ylcarbamate To a solution of (R)-3-[(tert-butoxycarbonyl)amino]-4-(2,4,5-trifluorophenyl)butanoic acid (1.64 g, 4.92 mmol) in dry DCM (15 mL) was added EDC (1.037 g, 5.412 mmol) and HOBT (0.731 g, 5.412 mmol) at 0° C. The resulting solution was stirred for 5 min and DIPEA (0.94 mL, 5.412 mmol) was added to it, followed by the addition of 7,8-difluoro-1,3,4,5-tetrahydro-benzo[e][1,4]diazepin-2-one (0.97 g, 4.92 mmol). The reaction mixture was stirred for 5 h at r.t. under argon. After completion of the reaction as confirmed by TLC, water (30 mL) was added to the reaction mixture and crude compound was extracted with DCM (3×30 mL). The combined organic layers were dried over $Na_2SO_4$ and the solvents were removed in vacuo to afford the crude compound which was purified by column chromatography (silica gel: 0.7:99.3 MeOH: $CHCl_3$) to afford pure [3-(7,8-difluoro-2-oxo-1,2,3,5-tetrahydro-benzo[e][1,4]diazepine-4-yl)-3-oxo-1-(2,4,5-trifluorzyl)-propyl]-carbamic acid tert-butylester (0.682 g, 27%).
$^1$H NMR (400 MHz, $CDCl_3$): δ 1.35 and 1.38 (two rotameric singlets, 9H), 2.54-2.65 (m, 2H), 2.89-2.92 (m, 2H), 4.12 (m, 1H), 4.17-4.20 (m, 1H), 4.44-4.62 (m, 3H), 5.38-5.43 (m, 1H), 6.84-6.90 (m, 2H), 6.98-7.21 (m, 2H), 8.11 and 8.31 (two bs, 1H)
ESIMS (m/z): 514.4 (M+1)

Step 11: Preparation of trifluoroacetic acid salt of (R)-4-(3-amino-4-(2,4,5-trifluorophenyl)butanoyl)-7,8-difluoro-4,5-dihydro-1H-benzo[e][1,4]diazepin-2 (3H)-one To a solution of [3-(7,8-difluoro-2-oxo-1,2,3,5-tetrahydro-benzo[e][1,4]diazepine-4-yl)-3-oxo-1-(2,4,5-trifluorzyl)-propyl]-carbamic acid tert-butylester, (0.682 g, 1.32 mmol) in dry DCM (5 mL) was added trifluoroacetic acid mL, 3 mL/mmol) at 0° C. The reaction mixture was stirred at r.t. for 2 h under argon. After completion of the reaction as confirmed by TLC, the reaction mixture was evaporated under vacuo to remove excess of solvent and trifluoroacetic acid. The remaining solvents were removed under vacuo and the crude compound was triturated with diethylether (5 mL) resulting in trifluoroacetic acid salt of (R)-4-(3-amino-4-(2,4,5-trifluorophenyl)butanoyl)-7,8-difluoro-4,5-dihydro-1H-benzo[e][1,4]diazepin-2(3H)-one (0.63 g, 90%) as a white solid.
$^1$H NMR (400 MHz, $CDCl_3$): δ 2.65-2.88 (m, 2H), 2.97-3.08 (m, 2H), 3.81-3.92 (m, 1H), 4.22 (s, 1H), 4.45-4.64 (m, 3H), 7.01-7.33 (m, 4H)
ESIMS (m/z): 415.6 (M+1)

Example 3

Preparation of trifluoroacetic acid salt of 4-[(R)-3-amino-4-(2,4,5-trifluorophenyl)-butyryl]-1-methyl-1,3,4,5-tetrahydro-benzo[e][1,4]diazepin-2-one

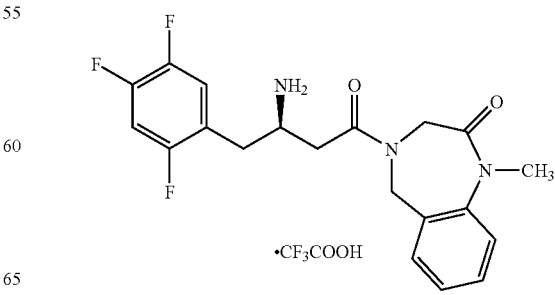

Step 1: Preparation of 1-methyl-2-oxo-1,2,3,5-tetrahydro-benzo[e][1,4]diazepine-4-carboxylic acid tert-butyl ester Sodium hydride (18 mg, 0.45 mmol, 60% suspension in mineral oil) was washed with hexane (2×2 mL) in, a flame dried round bottomed flask under nitrogen atmosphere. To the resulting free floating powder, was added a solution of 2-oxo-1,2,3,5-tetrahydro-benzo[e][1,4]diazepine-4-carboxylic acid tert-butyl ester (80 mg, 0.30 mmol) in dry DMF (3 mL) at 0° C. The reaction mixture was stirred at this temperature for 1 h. Iodomethane (0.0.19 mL, 0.30 mmol) was added at 0° C. and the reaction mixture was allowed to come to r.t. and stirred overnight. After the completion of the reaction as confirmed by TLC, reaction mixture was cooled to 0° C. and saturated solution of ammonium chloride (2 mL) was added dropwise to the reaction mixture. The crude product was extracted with ethyl acetate (2×10 mL). The combined organic layers were dried over $Na_2SO_4$ and the solvents were removed in vacuo to afford 1-methyl-2-oxo-1,2,3,5-tetrahydro-benzo[e][1,4]diazepine-4-carboxylic acid tert-butyl ester (75 mg, 89%) as a viscous oil which was used as such without any further purification for the next step.

ESIMS (m/z): 278.3 (M+2), 277.3 (M+1)

Step 2: Preparation of trifluoroacetic acid salt of 1-methyl-1,3,4,5-tetrahydrobenzo[e][1,4]diazepin-2-one To a solution of 1-methyl-2-oxo-1,2,3,5-tetrahydro-benzo[e][1,4]diazepine-4-carboxylic acid tert-butyl ester (70 mg, 0.25 mmol) in dry DCM (10 mL), was added trifluoroacetic acid (0.75 mL, 3 mL/mmol). The mixture was stirred at r.t. for 1 h. After the completion of the reaction as confirmed by TLC, excess of TFA and DCM were evaporated in vacuo to afford trifluoroacetic acid salt of 1-methyl-1,3,4,5-tetrahydrobenzo[e][1,4]diazepin-2-one (70 mg, 95%) as a gummy solid which was used as such for next coupling.

Step 3: Preparation of 2 [3-(1-methyl-2-oxo-1,2,3,5-tetrahydro-benzo[e][1,4]diazepin-4-yl)-3-oxo-(R)-1-(2,4,5-trifluoro-benzyl)-propyl]-carbamic acid tert-butyl ester To a solution of (R)-3-[(tert-butoxycarbonyl)amino]-4-(2,4,5-trifluorophenyl)butanoic acid (80 mg, 0.24 mmol) in dry DCM (10 mL), was added HOBT (42 mg, 0.31 mmol), EDC (59 mg, 0.31 mmol) and DIPEA (0.20 mL, 1.2 mmol). The reaction mixture was stirred at r.t. for 10 min. A solution of 1-methyl-1,3,4,5-tetrahydrobenzo (e) [1,4]diazepin-2-one trifluoroacete (70 mg, 0.24 mmol) in dry DCM (5 mL) was added and the reaction mixture was stirred at r.t. overnight. After the completion of the reaction, as confirmed by TLC, the crude product was extracted with DCM (10 mL) and washed sequentially with 10%. HCl solution (10 mL) and saturated solution of sodium bicarbonate (10 mL). The organic layer was separated and washed with brine and dried over $Na_2SO_4$. The solvents were removed in vacuo to afford the crude compound, which was purified by column chromatography (silica gel, 3:7 EtOAc:Pet.Ether) to afford 2 [3-(1-methyl-2-oxo-1,2,3,5-tetrahydro-benzo[e][1,4]diazepin-4-yl)-3-oxo-(R)-1-(2,4,5-trifluoro-benzyl)-propyl]-carbamic acid tert-butyl ester (95 mg, 78%) as viscous oil.

ESIMS (m/z): 492.3 (M+1)

Step 4: Preparation of trifluoroacetic acid salt of 4-[(R)-3-amino-4-(2,4,5-trifluorophenyl)-butyryl]-1-methyl-1,3,4,5-tetrahydro-benzo[e][1,4]diazepin-2-one To a solution of 2 [3-(1-methyl-2-oxo-1,2,3,5-tetrahydro-benzo[e][1,4]diazepin-4-yl)-3-oxo-(R)-1-(2,4,5-trifluoro-benzyl)-propyl]-carbamic acid tart-butyl ester (90 mg 0.18 mmol) in dry DCM (5 mL), was added trifluoroacetic acid (0.55 mL, 3 mL/mmol). The reaction mixture was stirred at r.t. for 1 h. After completion of the reaction, as confirmed by TLC, excess of TFA and DCM were evaporated in vacuo to afford a gummy solid which was crystallised from hexane to afford trifluoroacetic acid salt of 4-[(R)-3-amino-4-(2,4,5-trifluorophenyl)-butyryl]-1-methyl-1,3,4,5-tetrahydro-benzo[e][1,4]diazepin-2-one (70 mg, 76%) as a white solid $^1$H NMR (400 MHz, MeOD): δ 2.72-2.89 (m, 2H), 2.99-3.09 (m, 2H), 3.40 (s 3H), 3.88-3.92 (m, 2H), 4.05-4.15 (m, 1H), 4.50-4.58 (m, 21H), 7.20-7.25 (m, 1H), 7.28-7.53 (m, 5H)

ESIMS (m/z): 415.4 (M+Na), 391.1 (M+1)

Example 4

Preparation of trifluoroacetic acid salt of {4-[(R)-3-amino-4-(2,4,5-trifluoro-phenyl)-butyryl]-2-oxo-2,3,4,5-tetrahydro-benzo[e][1,4]diazepin-1-yl}-acetic acid

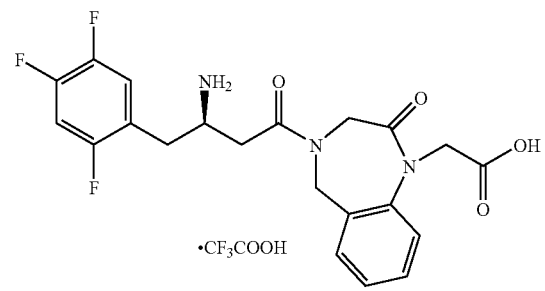 [SMILES: N[C@@H](CC(=O)N1CC(=O)N(CC(=O)O)c2ccccc2C1)Cc1cc(F)c(F)cc1F ; "·CF3COOH"]

Step 1: Preparation of 1-ethoxycarbonylmethyl-2-oxo-1,2,3,5-tetrahydro benzo[e][1,4]diazepine-4-carboxylic acid tert-butyl ester Sodium hydride (152.6 mg, 3.81 mmol, 60% suspension in mineral oil) was washed with hexane (2×2 mL) in a flame dried round bottomed flask under nitrogen atmosphere. To the resulting free floating powder, was added a solution of 2-oxo-1,2,3,5-tetrahydro-benzo[e][1,4]diazepine-4-carboxylic acid tert-butyl ester (500 mg, 1.90 mmol) in dry DMF (10 mL) at 0° C. The reaction mixture was stirred at this temperature for 1 h. Ethyl bromoacetate (0.21 mL, 1.9 mmol) was added at 0° C. and the reaction mixture was allowed to come to r.t. and stirred overnight. After the completion of the reaction as confirmed by TLC, reaction mixture was cooled to 0° C. and saturated solution of ammonium chloride (3 mL) was added dropwise to the reaction mixture. The crude product was extracted with ethylacetate (3×10 mL). The combined organic layers were dried over $Na_2SO_4$ and solvents were removed in vacuo to afford 1-ethoxycarbonylmethyl-2-oxo-1,2,3,5-tetrahydro-benzo[e][1,4]diazepine-4-carboxylic acid tert-butyl ester (480 mg, 72%) as a viscous oil which was used as such without any further purification for the next step.
ESIMS (m/z): 349.1 (M+1)

Step 2: Preparation of trifluoroacetic acid salt of (2-oxo-2,3,4,5-tetrahydro-benzo[e][1,4]diazepin-1-yl)-acetic acid ethyl ester To a solution of 1-ethoxycarbonylmethyl-2-oxo-1,2,3,5-tetrahydro-benzo[e][1,4]diazepine-4-carboxylic acid tert-butyl ester (125 mg, 0.36 mmol) in dry DCM (5 mL) was added trifluoroacetic acid (1.08 mL, 3 mL/mmol). The reaction mixture was stirred at r.t. for one hour. After completion of the reaction, as confirmed by TLC, excess of trifluoroacetic acid and DCM were evaporated in vacuo to afford trifluoroacetic acid salt of (2-oxo-2,3,4,5-tetrahydro-benzo[e][1,4]diazepin-1-yl)-acetic acid ethyl ester (119 mg, 92%) as a gummy solid which was used as such without any further purification for the next step.

Step 3: Preparation of {4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic ACID methyl ester To a solution of (R)-3-[tert-butoxycarbonyl)amino]-4-(2,4,5-trifluorophenyl)butanoic acid (100 mg, 0.30 mmol) was dissolved in dry DCM (10 mL), was added HOBT (53 mg, 0.39 mmol), EDC (75 mg, 0.39 mmol) and DIPEA (0.26 mL, 1.49 mmol). The reaction mixture was stirred at r.t. for 10 min. A solution of (2-oxo-2,3,4,5-tetrahydro-benzo[e][1,4]diazepin-1-yl)-acetic acid ethyl ester trifluoroacetate (119 mg, 0.33 mmol) in DCM (5 mL) was added and the reaction mixture was stirred r.t. overnight under nitrogen atmosphere. After the completion of the reaction, as confirmed by TLC, the crude product was extracted with DCM (10 mL) and washed sequentially with 10% HCl (10 mL) and saturated solution of sodium bicarbonate (10 mL). The organic layer was separated, washed with water, dried over $Na_2SO_4$ and concentrated in vacuo to afford the crude compound, which was purified by column chromatography (silica gel, 1:1 EtOAc:Pet Ether) to afford {4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid methyl ester (103 mg, 61%) as a viscous oil.
ESIMS (m/z): 586.1 (M+Na); 564.0 (M+1)

Step 4: Preparation of {-4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid To a stirred solution of {4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid methyl ester (90 mg, 0.16 mmol) in THF (2 mL) and water (2 mL), was added lithium hydroxide (40 mg, 0.95 mmol). The reaction mixture was stirred at r.t. overnight. After the completion of the reaction as confirmed by TLC, the reaction mixture was cooled to 0° C. and neutralized with 10% HCl solution and the pH was adjusted to 1. The crude compound was extracted with ethylacetate (10 mL). The organic layer was washed with water, dried over $Na_2SO_4$. The solvents were removed in vacuo to afford {4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid (70 mg, 82%) as a viscous oil.
ESIMS (m/z): 558.3 (M+Na), 536.4 (M+1), 534.3 (M−1)

Step 5: Preparation of trifluoroacetic acid salt of {4-[(R)-3-amino-4-(2,4,5-trifluoro-phenyl)-butyryl]-2-oxo-2,3,4,5-tetrahydro-benzo[e][1,4]diazepin-1-yl}-acetic acid To a solution of {-4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid (60 mg, 0.11 mmol) in DCM (3 mL), was added trifluoroacetic acid (0.33 mL, 3 mL/mmol). The reaction mixture was stirred at r.t. for 1 h. After completion of the reaction, as confirmed by TLC, excess of trifluoroacetic acid and DCM were evaporated in vacuo to afford a gummy solid which was crystallized from hexane to afford trifluoroacetic acid salt of {4-[(R)-3-amino-4-(2,4,5-trifluoro-phenyl-butyryl]-2-oxo-2,3,4,5-tetrahydro-benzo[e][1,4]diazepin-1-yl}-acetic acid (50 mg, 82%) as a solid.
$^1$H NMR (400 MHz, MeOD): δ 2.64-2.90 (m, 2H), 2.98-3.12 (m, 2H), 3.80-3.88 (m, 1H), 3.95 (s, 1H), 4.05-4.17 (m, 1H), 4.61-4.64 (m, 2H), 4.73-4.81 (m, 2H), 7.20-7.40 (m, 6H)
ESIMS (m/z): 458.4 (M+Na), 436.3 (M+1)

Example 5

Preparation of trifluoroacetic acid salt of 2-{4-[(R)-3-amino-4-(2,4,5-trifluoro-phenyl)-butyryl]-2-oxo-2,3,4,5-tetrahydro-benzo[e][1,4]diazepin-1-yl}-N-cyclopropyl-acetamide

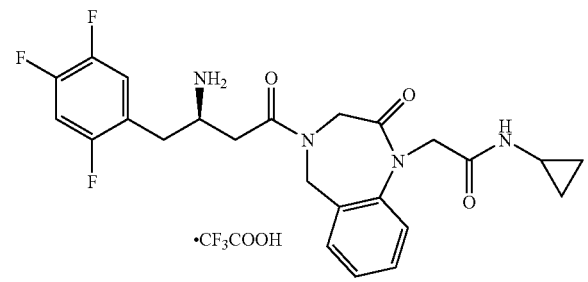 [SMILES: N[C@@H](CC(=O)N1CC(=O)N(CC(=O)NC2CC2)c2ccccc2C1)Cc1cc(F)c(F)cc1F ; "·CF3COOH"]

Step 1: Preparation of [3-(1-cyclopropylcarbamoylmethyl-2-oxo-1,2,3,5-tetrahydro-benzo[e][1,4]diazepin-4-yl)-3-oxo-1-(2,4,5-trifluoro-benzyl)-propyl]-carbamic acid tert-butyl ester This compound was obtained by coupling of {4-[3-tert-butoxycarbonylamino-4-(2,4,5-trifluoro-phenyl)-butyryl]-2-oxo-2,3,4,5-tetrahydro-benzo[e][1,4]diazepin-1-yl}-acetic acid and cyclopropylamine using HOBT, EDC, DIPEA following the above mentioned procedures.
ESIMS (m/z): 597.5 (M+Na), 575.4 (M+1)

Step 2: Preparation of trifluoroacetic acid salt of 2-{4-[(R)-3-amino-4-(2,4,5-trifluoro-phenyl)-butyryl]2-oxo-2,3,4,5-tetrahydro-benzo[e][1,4]diazepin-1-yl}-N-cyclopropyl acetamide To a solution of [3-(1-cyclopropylcarbamoylmethyl-2-oxo-1,2,3,5-tetrahydro-benzo[e][1,4]diazepin-4-yl)-3-oxo-1-(2,4,5-trifluoro-benzyl)-propyl]-carbamic acid tert-butyl ester (40 mg, 0.07 mmol) in DCM (2 mL), was added trifluoroacetic acid (0.2 mL, 3 mL/mmol). The reaction mixture was stirred at r.t. for 1 h. After the completion of the reaction as confirmed by TLC, excess of trifluoroacetic acid and DCM were removed in vacuo to afford a gummy solid which was crystallised from hexane to afford trifluoroacetic acid salt of 2-{4-[(R)-3-amino-4-(2,4,5-trifluoro-phenyl)-butyryl]-2-oxo-2,3,4,5-tetrahydro-benzo[e][1,4]diazepin-1-yl}-N-cyclopropyl-acetamide (32 mg, 78%).

¹H NMR (400 MHz, MeOD): δ 0.46-0.47 (m, 2H), 0.68-0.70 (m, 2H), 2.55-2.65 (m, 1H) 2.65-3.07 (m, 2H), 3.01-3.09 (m, 2H), 3.72-3.88 (m, 1H), 3.95 (s, 1H); 4.09-4.21 (m, 1H), 4.45-4.54 (m, 2H), 4.70-4.79 (m, 2H), 7.20-7.50 (m, 6H)

ESIMS (m/z): 497.3 (M+Na), 475.1 (M+1)

Example 6

Preparation of trifluoroacetic acid salt of (R)-3-amino-1-(9-fluoro-4H-benzo[f][1,2,4]triazolo[4,3-a][1,4]diazepin-5(6H)-yl)-4-(2,4,5-trifluorophenyl)butan-1-one

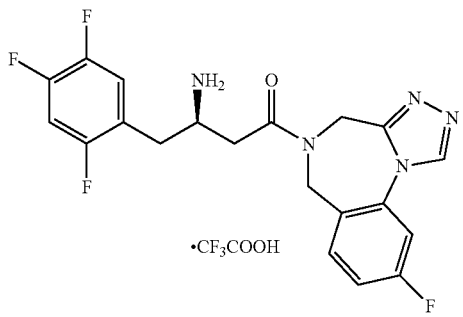 [SMILES: N[C@@H](CC(=O)N1Cc2ccc(F)cc2-n2cnnc2C1)Cc1cc(F)c(F)cc1F ; "·CF3COOH"]

Step 1: Preparation of (4-fluoro-2-nitro-benzylamino)-acetic acid methyl ester

To a solution of 1-bromoethyl-4-fluoro-2-nitrobenzene (5.00 g, 21.36 mmol) in DMF (50 mL) under argon atmosphere, was added DIPEA (11.16 mL, 64.10 mmol) dropwise at 0° C. The resulting solution was stirred for 5 min, followed by dropwise addition of solution of glycine methyl ester hydrochloride (3.48 g, 27.77 mmol) in DMF (5 mL) at 0° C. The reaction mixture was stirred at r.t. for 8 h. After completion of the reaction as confirmed by TLC, water (100 mL) was added and the crude compound was extracted with EtOAc (3×200 mL). The combined organic layers were washed with brine and dried over Na₂SO₄. The solvents were removed in vacuo to afford crude compound which was purified by column chromatography [silica gel, 2:8 EtOAc:Pet. ether] to afford 4-fluoro-2-nitro-benzylamino-acetic acid methyl-ester as a dark yellow viscous liquid (4.65 g, 90%).

ESIMS (m/z): 242.8 (M+1)

Step 2: Preparation of [tert-butoxycarbonyl-(4-fluoro-2-nitro-benzyl)-amino]-acetic acid methyl ester To a solution of 4-fluoro-2-nitro-benzylamino-acetic acid methyl ester (4.65 g, 19.21 mmol) in DCM (30 mL) under argon atmosphere, was added di-tert-butyl dicarbonate (4.41 mL, 19.21 mmol) dropwise at r.t. The reaction mixture was stirred at r.t., overnight. After completion of the reaction as confirmed by TLC, water (30 mL) was added and the mixture was extracted with DCM (3×100 mL). The combined organic layers were dried over Na₂SO₄ extracted and concentrated in vacuo. The crude compound was purified by column chromatography [silica gel, 2:8 EtOAc:Pet. ether] to afford pure tert-butoxycarbonyl-(4-fluoro-2-nitro benzyl)-amino-acetic acid methyl ester as a dark yellow liquid (5.91 g, 90%).

ESIMS (m/z): 366.1 (M+Na), 343.2 (M+1)

Step 3: Preparation of 2-(tert-butoxycarbonyl(4-fluoro-2-nitro-benzyl)amino)-acetic acid To a solution of crude [tert-butoxycarbonyl-(4-fluoro-2-nitro-benzyl)-amino]-acetic acid methyl ester (5.91 g, 17.2 mmol) in THF (50 mL) was added lithium hydroxide (4.35 g, 103.6 mmol,) dissolved in water (17 mL). The reaction was stirred at r.t. overnight. After completion of the reaction, as confirmed by TLC, the reaction mixture was acidified to pH 4 using 10% HCl and crude compound was extracted with MeOH and CHCl₃ (1:9, 3×50 mL). The combined organic layers were dried over Na₂SO₄. The solvents were removed in vacuo to afford 2-(tert-butoxycarbonyl(4-fluoro-2-nitrobenzyl)amino)-acetic acid (5.11 g, 90%) as brown thick gel, which was used as such without any further purification for the next step.

ESIMS (m/z): 328.0 (M−1)

Step 4: Preparation of 2-(2-amino-4-fluorobenzyl)(tert-butoxycarbonyl)amino) acetic acid To a solution of [tert-butoxycarbonyl-(4-fluoro-2-nitro-benzyl)-amino]-acetic acid (5.11 g, 15.50 mmol) in absolute EtOH (30 mL), was added 10% Pd/C (1.02 g, 20% w/w). The reaction was stirred at r.t. for 5 h under hydrogen atmosphere. After completion of the reaction, as confirmed by TLC, the reaction mixture was filtered through celite bed and was washed with EtOAc (10 mL) and MeOH (10 mL). The solvents were removed in vacuo to afford 2-((2-amino-4-fluorobenzyl) (tert-butoxycarbonyl)amino) acetic acid (4.64 g, 99.9%), which was used as such far the next step without any further purification.

Step 5: Preparation of tert-butyl 8-fluoro-2-oxo-1,3-dihydro-1H benzo[e][1,4]diazepine-4(5H)-carboxylate To a solution of [(2-amino-4-fluoro-benzyl) tert-butoxycarbonyl)-amino]-acetic acid (4.64 g, 15.51 mmol) in DCM (60 mL), were added EDC (3.83 g, 20.17 mmol) and HOBT (2.72 g, 20.17 mmol) at 0° C. The resulting solution was stirred for 5 min and DIPEA (8:10 mL, 46.55 mmol) was added. The reaction mixture was stirred overnight at r.t. under argon. After completion, of the reaction as confirmed by TLC, distilled water (60 mL) was added to the reaction mixture and crude compound was extracted with DCM (3×50 mL). The combined organic layers were dried over Na₂SO₄. The solvents were removed in vacuo to afford the crude compound which was purified by washings with EtOAc to give pure tert-butyl 8-fluoro-2-oxo-2,3-dihydro-1H benzo[e][1,4]diazepine-4(5H)-carboxylate (2.91 g, 67%) as a white solid.

ESIMS (m/z): 279.5 (M−1)

Step 6: Preparation of 8-fluoro-2-thioxo-1,2,3,5-tetrahydrobenzo[e][1,4]diazepine-4-carboxylic acid tert-butyl ester To a solution of 8-fluoro-2-oxo-1,2,3,5-tetrahydro-benzo[e][1,4]diazepine-4-carboxylic acid tert-butyl ester (3.24 g, 11.57 mmol) in toluene (50 mL), was added Lawesson's reagent (2.33 g, 5.78 mmol) at r.t. The reaction mixture was heated at 90° C. for 30-40 min. After completion of reaction, as confirmed by TLC, distilled water (50 mL) was added and the crude compound was extracted with EtOAc (3×50 mL). The combined organic layers were dried over $Na_2SO_4$. The solvents were removed in vacuo to afford the crude compound, which was purified by column chromatography (silica gel, 2:8 EtOAc:Pet. ether) to afford pure 8-fluoro-2-thioxo-1,2,3,5-tetrahydro-benzo[e][1,4]diazepine-4-carboxylic acid tert butyl ester (2.36 g, 69%) as light Yellow solid.

ESIMS (m/z): 297.3 (M+1)

Step 7: Preparation of 9-fluoro-4H,6H-2,3,5,10b-tetraaza-benzo[e]azulene-5-carboxylic acid tert-butyl ester To a solution of 8-fluoro-2-thioxo-1,2,3,5-tetrahydro-benzo[e][1,4]diazepine-4-carboxylic acid tert-butyl ester (2.36 g, 7.97 mmol) in dry benzene (25 mL), was added formic acid hydrazide dissolved in 5 mL of dry DMSO (1.43 g, 23.91 mmol) at room temperature. The reaction mixture was heated at 80° C., using Dean-Stark apparatus for 18 h. After the completion of the reaction, as confirmed by TLC, distilled water (40 mL) was added and the crude compound was extracted with diethyl ether (3×40 mL). The combined organic layers were dried over $Na_2SO_4$ and concentrated in vacuo to afford the crude compound which, was purified by column chromatography [silica gel, 1.5:8.5 Acetone:Pet. ether] to afford 9-fluoro-4H,6H-2,3,5,10b-tetraaza-benzo[e]azulene-5-carboxylic acid tert-butyl ester, (1.455 g, 60%) as a white solid.

ESIMS (m/z): 305.5 (M+1)

Step 8: Preparation of 9-fluoro-5,6-dihydro-4H-2,3,5,10b-tetraaza-benzo[e]azulene trifluoroacetate To a solution of 9-fluoro-4H,6H-2,3,5,10b-tetraaza-benzo[e]azulene-5-carboxylic acid tert-butyl ester, (1.45 g, 4.76 mmol) in dry DCM (15 mL) was added trifluoroacetic acid (14.30 mL, 3 mL/mmol) at 0° C. The reaction mixture was stirred at r.t. for 2 h under argon. After completion of the reaction as confirmed by TLC, MeOH (2×10 mL) was added and the reaction mixture was evaporated under vacuo to remove excess of solvent and trifluoroacetic acid. The remaining solvents were removed under vacuo and 9-fluoro-5,6-dihydro-4H-2,3,5,10b-tetraaza-benzo[e]azulene trifluoroacetate (1.50 g, 4.71 mmol, 99%) was obtained as thick brown jelly. The crude compound was used as such without any further purification for the next step.

ESIMS (m/z): 205.2 (M+1), for free amine.

Step 9: Preparation of [3-(9-fluoro-4H,6H-2,3,5,10b tetraaza-benzo[e]azulen-5-yl)-3-oxo-1-(2,4,5-trifluoro-benzyl)-propyl]-carbamic acid-tert-butyl ester To a solution of (R)-3-[(tert-butoxycarbonyl)amino]-4-(2,4,5-trifluorophenyl)butanoic acid (1.56 g, 4.68 mmol) in dry acetonitrile (15 mL), was added DIPEA (2.03 mL, 11.71 mmol), followed by the addition of (benzotriazolyl-1-yloxy)-tris(dimethylamine) phosphonium hexafluorophosphate (2.27 g, 5.15 mmol) at r.t. 9-fluoro-5,6-dihydro-4H-2,3,5,10b-tetraaza-benzo[e]azulene trifluoroacetate (1.56 g, 4.91 mmol), dissolved in dry acetonitrile (10 mL) and DIPEA (0.98 mL, 5.63 mmol), was added to the reaction mixture at r.t. The reaction was stirred at 40° C. for 48 h. After completion of the reaction, as confirmed by TLC, solvent was removed in vacuo and distilled water (40 mL) was added to the residue. The crude compound was extracted with EtOAc (3×50 mL) and the combined organic layers were dried over $Na_2SO_4$. The solvents were removed in vacuo to afford the crude compound, which was purified by column chromatography (silica gel, 1.2:8.8 MeOH:$CHCl_3$) to afford 3-(9-fluoro-4H,6H-2,3,5,10b tetraaza-benzo[e]-azulen-5-yl)-3-oxo-1-(2,4,5-trifluoro-benzyl)-propyl]-carbamic acid-tert-butyl ester, (2.04 g, 83.9%), as a white solid solid.

$^1$H NMR (400 MHz, $CDCl_3$): δ 1.35 and 1.37 (two rotameric singlets, 1H), 2.62-2.93 (m, 2H), 2.95-2.99 (m, 2H), 4.14-4.17 (m, 1H), 4.41 (s, 1H), 4.57-4.60 (m, 1H), 4.76 (s, 1H), 4.93 (s, 1H), 5.44-5.46 (m, 1H), 6.86-6.89 (m, 1H), 7.03-7.07 (m, 1H), 7.18-7.23 (m, 2H), 7.57-7.60 (m, 1H), 8.49 and 8.50 (two rotameric singlets, 1H)

ESIMS (m/z): 520.5 (M+1)

Step 10: Preparation of trifluoroacetic acid salt of(R)-3-amino, 1-(9-fluoro-4H,6H-2,3,5,10b-tetraaza-benzo[e]azulen-5-yl)-4-(2,4,5-trifluoro-phenyl)-butan-1-one To a solution of [3-(9-fluoro-4H,6H-2,3,5,10b tetraaza-benzo[e]-azulen-5-yl)-3-oxo-1-(2,4,5-trifluoro-benzyl)-propyl]-carbamic acid-tert-butyl ester, (2.04 g, 3.93 mmol); in dry DCM (12 mL) was added trifluoroacetic acid (11.79 mL, 3 mL/mmol) at 0° C. The reaction mixture was stirred at r.t. for 2 h under argon. After completion of the reaction as confirmed by TLC, methanol (2×5 mL) was added and the reaction mixture was evaporated under vacuo to remove excess of solvent and trifluoroacetic acid. The remaining solvents were removed under vacuo to obtain trifluoroacetic acid salt of (R)-3-amino-1-(9-fluoro-4H,6H-2,3,5,10b-tetraaza-benzo[e]azulen-5-yl)-4-(2,4,5-trifluoro-phenyl)-butan-1-one as a white solid (1.82 g, 3.42 mmol, 87%).

$^1$H NMR (400 MHz, $CD_3OD$): δ 2.62-3.15 (m, 4H), 3.87 (bs, 1H), 4.50-4.52 (m, 1H), 4.52-4.70 (m, 1H), 4.82-4.90 (m, 2H), 7.20-7.34 (m, 3H), 7.58-7.64 (m, 2H), 9.02-9.03 (two rotameric singlets, 1H)

ESIMS (m/z): 420.5 (M+1), Mass of free amine

Example 7

Preparation of trifluoroacetic acid salt of (R)-3-amino-1-(4H, 6H-3,5,10b-triaza-benzo[e]azulen-5-yl)-4-(2,4,5-trifluoro-phenyl)-butan-1-one

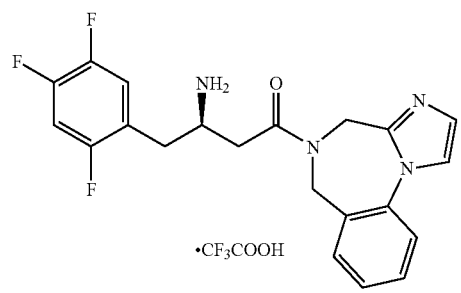 [SMILES: N[C@@H](CC(=O)N1Cc2ccccc2-n2ccnc2C1)Cc1cc(F)c(F)cc1F ; "·CF3COOH"]

Step 1: Preparation of 2-(2-hydroxy-ethylamino)-3,5-dihydro-benzo[e][1,4]diazepine-4-carboxylic acid tert-butyl ester 2-aminoethanol (3.5 mL, 10 mL/mmol) was added to a solution of tert-butyl 2-thioxo-2,3-dihydro-1H-benzo[e][1,4]

diazepine-4(5H)-carboxylate (100 mg, 0.35 mmol), [prepared as described in Example 6, Step 6] and the reaction mixture was heated to reflux for 24 h under nitrogen atmosphere. The reaction mixture was cooled to room temperature, diluted with ethylacetate (50 mL) and washed with water (20 mL). The organic layer was separated, dried over anhydrous sodium sulphate and concentrated to give the desired compound as viscous oil (100.0 mg, 90%) which was used as such for the next step.

ESIMS (m/z): 328.3 (M+Na), 305.9 (M+1).

Step 2: Preparation of 4H-6H-3,5,10b-triaza-benzo[e]azulene-5-carboxylic acid tert-butyl ester To a solution of DMSO (0.05 mL, 0.82 mmol) in DCM (5.0 mL) at −78° C., was added oxalyl chloride (0.04 mL, 0.43 mmol) dropwise. The reaction mixture was stirred at this temperature for 0.5 h, followed by dropwise addition of a solution of 2-(2-hydroxy-ethylamino)-3,5-dihydro-benzo[e][1,4]diazepine-4-carboxylic acid test-butyl ester (100 mg, 0.32 mmol) in DCM (1 mL). The reaction mixture was stirred at −78° C. for 2 h. triethylamine (1.0 mL) was added to the reaction mixture and warmed to room temperature. The crude product was extracted with DCM (20 mL). The organic layer was washed with water (2×15 mL), dried over anhydrous $Na_2SO_4$ and concentrated in vacuo to afford the crude compound which was purified by column chromatography (silica gel, 8:2 EtOAc:Pet.Ether) to afford 4H,6H-3,5,10b-triaza-benzo[e]azulene-5-carboxylic acid tert-butyl ester (25 mg, 27%) as a viscous oil.

ESIMS (m/z): 301.3 (M+1).

Step 3: Preparation of [3-oxo-3-(4H,6H-3,5,10b-triaza-benzo[c]azulen-5-yl)-1-(2,4,5-trifluoro-benzyl)-propyl]-carbamic acid tert-butyl ester 4H,6H-3,5,10b-Triaza-benzo[e]azulene-5-carboxylic acid tert-butyl ester was deprotected using trifluoroacetic acid and the resulting salt was coupled with (R)-3-[(tert-butoxycarbonyl)amino]-4-(2,4,5-trifluorophenyl)butanoic acid using HOBT, EDC and DIPEA to afford [3-oxo-3-(4H,6H-3,5,10b-triaza-benzo[e]azulen-5-yl)-1-(2,4,5-trifluoro-benzyl)-propyl]-carbamic acid tert-butyl ester as a viscous oil.

ESIMS (m/z): 424.1 (M+Na), 401.4 (M+1).

Step 4: Preparation of trifluoroacetic acid salt of 3-amino-1-(4H,6H-3,5,10b-triaza-benzo[e]azulen-5-yl)-4-(2,4,5-trifluoro-phenyl)-butan-1-one To a solution of [3-oxo-3-(4H,6H-3,5,10b-triaza-benzo[e]azulen-5-yl)-1-(2,4,5-trifluoro-benzyl)-propyl]-carbamic acid tert-butyl ester (30 mg, 0.06 mmol) in DCM (3 mL), was added trifluoroacetic acid (0.18 nit, 3 mL/mmol)). The reaction mixture was stirred at r.t. for 1 h. After the completion of the reaction as confirmed by TLC, excess of trifluoroacetic acid and DCM were removed in vacuo to afford a gummy solid which was crystallised from hexane to afford trifluoroacetic acid salt of 3-amino-1-(4H,6H-3,5,10b-triaza-benzo[e]azulen-5-yl)-4-(2,4,5-trifluoro-phenyl)-butan-1-one (30 mg, 98%).

$^1$H NMR (400 MHz, MeOD): δ 2.72-2.99 (m, 2H), 3.00-3.17 (m, 2H), 3.80-3.98 (m, 1H), 4.51-4.70 (m, 2H), 4.72-5.08 (m, 2H), 7.12-7.27 (m, 1H), 7.28-7.42 (m, 1H), 7.45-7.81 (m, 5H), 7.82-8.12 (m, 1H)

ESIMS (m/z): 424.1 (M+Na), 401.4 (M+1)

Example 8

Preparation of trifluoroacetic acid salt of (R)-3-amino-1-(4H,6H-1,2,5,10b-tetraaza-benzo[e]azulen-5-yl)-4-(2,4,5-trifluoro-phenyl)-butan-1-one

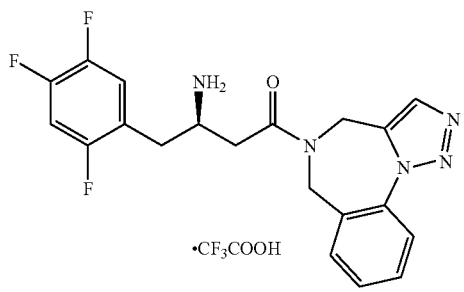 [SMILES: N[C@@H](CC(=O)N1Cc2ccccc2-n2nncc2C1)Cc1cc(F)c(F)cc1F ; "·CF3COOH"]

Step 1: Preparation of (2-Azido-benzyl)-carbamic acid tert-butyl ester

To a solution of (2-amino-benzyl)-carbamic acid tert-butyl ester [prepared from 2-aminobenzylamine and di-tert-butyl dicarbonate], (100 mg, 0.45 mmol) in acetic acid (2.46 mL), was added water (26 mL). Reaction mixture was cooled to 0° C. and a solution of sodium nitrite (62 mg, 0.9 mmol) in water (4.3 ml) was added. The reaction mixture was stirred for 30 min at the same temperature followed by addition of sodium azide (64 mg, 0.99 mmol). The reaction mixture was stirred at 0° C. for 30 min. When the reaction was complete as confirmed by TLC, reaction mixture was quenched by dropwise addition of 10 N NaOH (5.0 mL). The crude compound was extracted with ethylacetate (2×10 mL). Organic layer was separated, washed with brine, dried over $Na_2SO_4$ and the solvents were removed in vacuo to afford (2-azido-benzyl)-carbamic acid tert-butyl ester (105 mg, 96%) which was used as such without any further purification for the next step.

ESIMS (m/z): 271.3 (M+Na), 249.1 (M+1).

Step 2: Preparation of (2-azido-benzyl)-prop-2-ynyl-carbamic acid tert-butyl ester Sodium hydride (5.0 mg, 0.120 mmol, 60% suspension in mineral oil) was washed with hexane (2 mL) in a flame dried round bottomed flask under nitrogen atmosphere. To the resulting free floating powder, was added a solution of (2-azido-benzyl)-carbamic acid tert-butyl ester (20 mg, 0.08 mmol) in dry DMF (1 mL) at 0° C. The reaction mixture was stirred at this temperature for 30 min. Propargyl bromide (0.021 mL, 0.24 mmol) was added and the reaction mixture was stirred at r.t. for 2 h. After the completion of reaction as confirmed by TLC, crude product was extracted with ethylacetate (10 mL). The organic layer was washed with water (2×5 mL). Organic layer was dried over $Na_2SO_4$ and concentrated in vacuo to afford the crude compound which was purified by column chromatography (silica gel; 1:9 EtOAc:Pet.Ether) to afford (2-azido-benzyl)-prop-2-ynyl-carbamic acid ten-butyl ester (20 mg, 87%) as a viscous oil.

ESIMS (m/z): 309.2 (M+Na), 287.4 (M+1).

Step 3: Preparation of 4H,6H-1,2,5,10b-tetraaza-benzo[e]azulene-5-carboxylic acid tert-butyl ester Toluene (3 mL) was added to (2-azido-benzyl)-prop-2-ynyl-carbamic acid tert-butyl ester (100 mg, 0.34 mmol) and the resulting mixture was heated at 100° C. overnight. When the reaction was complete as confirmed by TLC, solvent was removed in vacuo to afford 4H,6H-1,2,5,10b-tetraaza-benzo[e]azulene-5-carboxylic acid tert-butyl ester (92 mg, 92%) which was used as such without any further purification for the next step. ESIMS (m/z): 309.4 (M+Na), 287.1 (M+1).

Step 4: Preparation of [3-oxo-3-(4H,6H-1,2,5,10b-tetraaza-benzo[e]azulen-5-yl)-1-(2,4,5-trifluoro-benzyl)-propyl]-carbamic acid tert-butyl ester 4H,6H-1,2,5,10b-Tetraaza-benzo[e]azulene-5-carboxylic acid tert-butyl ester was deprotected using trifluoroacetic acid and the resulting salt was coupled with (R)-3-[(tert-butoxycarbonyl)amino]-4-(2,4,5-trifluorophenyl)butanoic acid using HOBt, EDC and DIPEA. The desired compound was obtained as viscous oil.
ESIMS (m/z): 524.9 (M+Na), 502.5 (M+1).

Step 5: Preparation of trifluoroacetic acid salt of (R)-3-amino-1-(4H,6H-3,5,10b-triaza-benzo[e]azulen-5-yl)-4-(2,4,5-trifluoro-phenyl)-butan-1-one To a solution of [3-oxo-3-(4H,6H-1,2,5,10b-tetraaza-benzo[e]azulen-5-yl)-1-(2,4,5-trifluoro-benzyl)-propyl]-carbamic acid tert-butyl ester (30 mg, 0.06 mmol) in DCM (3 mL), was added trifluoroacetic acid (0.18 mL, 3 mL/mmol). The reaction mixture was stirred at r.t. for 1 h. When the reaction was complete as confirmed by TLC, excess of trifluoroacetic acid and DCM were removed in vacuo to afford a gummy solid which was crystallised from hexane to afford trifluoroacetic acid salt of (R)-3-amino-1-(4H,6H-3,5,10b-triaza-benzo[e]azulen-5-yl)-4-(2,4,5-trifluoro-phenyl)-butan-1-one (30 mg, 98%)
$^1$H NMR (400 MHz, MeOD): δ 2.52-2.83 (m, 2H), 2.85-2.88 (m, 2H), 3.59-3.65 (m, 1H), 4.51 (s, 1H), 4.58 (s, 1H), 4.72-4.78 (m, 2H), 7.12-7.17 (m, 1H), 7.25-7.29 (m, 1H), 7.53-7.60 (m, 2H), 7.62-7.67 (m, 1H), 7.90 (s, 1H), 7.91-7.99 (m, 1H);
ESIMS (m/z): 424.4 (M+Na), 402.4 (M+1)

Example 9

Preparation of trifluoroacetic acid salt of (R)-3-amino-1-[3-(4-fluoro-phenyl)-4H,6H-1,2,5,10b-tetraaza-benzo[e]azulen-5-yl]-4-(2,4,5-trifluoro-phenyl)-butan-1-one

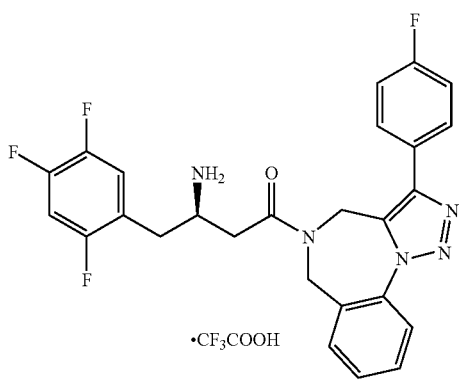 [SMILES: N[C@@H](CC(=O)N1Cc2ccccc2-n2nnc(-c3ccc(F)cc3)c2C1)Cc1cc(F)c(F)cc1F ; "·CF3COOH"]

Step 1: Preparation of 3-(4-fluoro-phenyl)-prop-2-yn-1-ol

To a mixture of 4-fluoroiodobenzene (710.0 mg, 3.82 mmol), bistriphenylphosphine palladium chloride (27.0 mg, 0.038 mmol), CuI (3.64 mg, 0.019 mmol) and propargyl alcohol (214.0 mg, 3.82 mmol), was added diisopropylamine (6.1 mL, 1.6 mL/mmol) under nitrogen atmosphere. The reaction mixture was stirred at r.t. for 6 h. After the completion of the reaction as confirmed by TLC, the crude product was extracted with ethylacetate (50 mL). The organic layer was washed with 10% HCl (20 mL), dried over Na$_2$SO$_4$ and concentrated in vacuo to afford the crude compound which was purified by column chromatography (silica gel, 2:8 EtOAc:Pet.Ether) to afford 3-(4-fluoro-phenyl)-prop-2-yn-1-ol (366.0 mg, 64%) as a viscous oil.

Step 2: Preparation of 1-(3-bromo-prop-1-Ynyl)-4-fluoro-benzene

To a solution of 3-(4-fluoro-phenyl)-prop-2-yn-1-ol (360 mg, 2.4 mmol) in dry DCM (5 mL) at 0° C., was added triethylamine (0.7 mL, 3.6 mmol) under nitrogen atmosphere. The reaction mixture was stirred for 15 min, followed by dropwise addition of methanesulfonyl chloride (0.3 mL, 3.6 mmol). The mixture was stirred at the same temperature for 30 min. After the completion of the reaction as confirmed by TLC, the crude product was extracted with DCM (10 mL). The organic layer was washed with water (10 mL), separated, dried over Na$_2$SO$_4$ and concentrated in vacuo to afford the mesylated product as viscous oil which was used as such for next step. To the resulting compound (600 mg, 21.04 mmol) in dry THF (20 mL) at 0° C., was added solid Lithium bromide (1.8 g, 21.63 mmol) under nitrogen atmosphere. The reaction mixture was stirred at r.t. for 2 h. After the completion of the reaction, as confirmed by TLC, water (20 mL) was added to the reaction mixture and the crude compound was extracted with ethylacetate (20 mL). The organic layer was separated, dried over Na$_2$SO$_4$ and concentrated in vacuo to afford the crude compound, which was purified by column chromatography (silica gel, 2:8 EtOAc:Pet.Ether) to afford 1-(3-bromo-prop-1-ynyl)-4-fluoro-benzene (460 mg, 82.5%) as a viscous oil.
ESIMS (m/z): 214.5 (M+2)

Step 3: Preparation of 3-(4-fluoro-phenyl)-4H,6H-1,2,5,10b-tetraaza-benzo[e]azulene-5-carboxylic acid tert-butyl ester Sodium hydride (80.0 mg, 2.0 mmol; 60% suspension in mineral oil) was washed with hexane (2 mL) in a flame dried round bottomed flask under nitrogen atmosphere. To the resulting free floating powder, was added a solution of (2-azido-benzyl)-carbamic acid tert-butyl ester (250 mg, 1.0 mmol) in dry DMF (3 mL) dropwise at 0° C. under nitrogen atmosphere. The reaction mixture was stirred at this temperature for 30 min followed by dropwise addition of a solution of 1-(3-bromo-prop-1-ynyl)-4-fluoro-benzene (318.0 mg, 1.50 mmol) in dry DMF (1.5 mL). The reaction mixture was stirred at r.t. for 2 h. After the completion of the reaction as confirmed by TLC, the crude compound was extracted with ethylacetate (2×10 mL). The combined organic layer was washed with water (2×10 mL). Organic layer was separated, dried over Na$_2$SO$_4$ and concentrated in vacuo to afford the crude compound which was purified by column chromatography (silica gel, 1:9 EtOAc:Pet.Ether) to afford 3-(4-fluoro-phenyl)-4H, 6H-1,2,5,10b-tetraaza-benzo[e]azulene-5-carboxylic acid tert-butyl ester (70 mg, 12.2%) as a viscous oil.
ESIMS (m/z): 381.6 (M+1).

Step 4: Preparation of [3-[3-(4-fluoro-phenyl)-4H, 6H-1,2,5,10b-tetraaza-benzo[e]azulen-5-yl]-3-oxo-1-(2,4,5-trifluoro-benzyl)-propyl]-carbamic acid tert-butyl ester 3-(4-Fluoro-phenyl)-4H,6H-1,2,5,10b-tetraaza-benzo[e] azulene-5-carboxylic acid tert-butyl ester was deprotected using trifluoroacetic acid and the resulting salt was coupled with (R)-3-[(tert-butoxycarbonyl)amino]-4-(2,4,5-trifluorophenyl)butanoic acid using HOBT, EDC and DIPEA. The desired compound was obtained as a viscous oil.
ESIMS (m/z): 619.1 (M+Na), 596.9 (M+1).

Step 5: Preparation of trifluoroacetic acid salt of (R)-3-amino-1-[3-(4-fluoro-phenyl)-4H,6H-1,2,5,10b-tetraaza-benzo[e]azulen-5-yl]-4-(2,4,5-trifluoro-phenyl)-butan-1-one To a solution of [3-[3-(4-fluoro-phenyl)-4H,6H-1,2,5,10b-tetraaza-benzo[e]azulen-5-yl]-3-oxo-1-(2,4,5-trifluoro-benzyl)-propyl]carbamic acid tert-butyl ester (28.0 mg, 0.047 mmol) in DCM (2 mL), was added trifluoroacetic acid (0.18 mL, 3 mL/mmol). The reaction mixture was stirred at r.t. for 1 h. After the completion of the reaction as confirmed by TLC, excess of trifluoroacetic acid and DCM were evaporated in vacuo to afford a gummy solid which was crystallized from hexane to afford trifluoroacetic acid salt of (R)-3-amino-1-[3-(4-fluoro-phenyl)-4H,6H-1,2,5,10b-tetraaza-benzo[e] azulen-5-yl]-4-(2,4,5-trifluoro-phenyl)-butan-1-one (25 mg, 87%).
1H NMR (400 MHz, MeOD): δ 2.67-2.84 (m, 4H), 3.47-3.53 (m, 1H), 4.56-4.61 (m, 4H), 7.11-7.30 (m, 4H), 7.58-7.79 (m, 5H), 7.98-8.02 (m, 1H)
ESIMS (m/z): 496.7 (M+1)

Example 10

Preparation of trifluoroacetic acid salt of 5-[(R)-3-amino-4-(2,4,5-trifluoro-phenyl)-butyryl]-5,6-dihydro-4H-2,5,10b-triaza-benzo[e]azulene-3-carboxylic acid ethyl ester

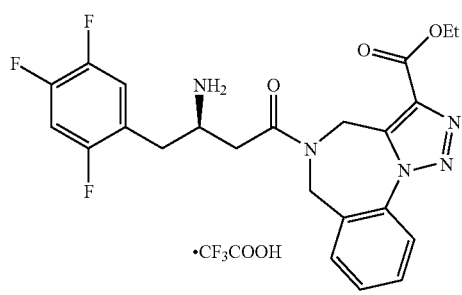 [SMILES: CCOC(=O)c1nnn2c1CN(C(=O)C[C@H](N)Cc1cc(F)c(F)cc1F)Cc1ccccc1-2 ; "·CF3COOH"]

Step 1: Preparation of 4H,6H-2,5,10b-triaza-benzo [e]azulene-3,5-dicarboxylic acid 5-tert-butyl ester 3-ethyl ester To a solution of 2-oxo-1,2,3,5-tetrahydro-benzo[e][1,4]diazepine-4-carboxylic acid tert-butyl ester (10.0 g, 38.16 mmol) in dry THF (300 mL) at 0° C., was added potassium tert-butoxide (6.4 g, 56.76 mmol) under nitrogen atmosphere and the reaction mixture was stirred at this temperature for 30 min followed by dropwise addition of diethylchlorophosphate (11 mL, 76.3.3 mmol). The reaction mixture was stirred at 0° C. for 40 min. This solution was transferred via cannula to a suspension of potassium tert-butoxide (12.86 g, 114.56 mmol) and ethyl isocyanoacetate (11.66 mL, 102.65 mmol) in dry THF (150 mL), kept in a separate flask at 0° C. under nitrogen atmosphere. When the addition was complete, the reaction mixture was allowed to come to r.t. and stirred for 45 min. during which the reaction was complete as confirmed by TLC. Reaction mixture was cooled to 0° C. and quenched with 10% acetic acid solution and stirred for 20 min. The crude compound was extracted with ethylacetate. The organic layer was washed with water, separated, dried over Na$_2$SO$_4$ and concentrated in vacuo to afford the crude compound which was purified by column chromatography (neutral alumina using neutral alumina, 3:7 EtOAc:Pet.Ether) to afford a viscous gel which was further purified by crystallisation from diethyl ether and hexane to afford 4H,6H-2,5,10b-triaza-benzo[e]azulene-3,5-dicarboxylic acid 5-tert-butyl ester 3-ethyl ester a white solid (4.4 g, 33%)
ESIMS (m/z): 380.6 (M+Na), 358.3 (M+1).

Step 2: Preparation of 5,6-dihydro-4H-2,5,10b-triaza-benzo[e]azulene-3-carboxylic acid ethyl ester trifluoroacetate To a solution of 4H,6H-2,5,10b-Triaza-benzo[e]azulene-3,5-dicarboxylic acid 5-tert-butyl ester 3-ethyl ester (300 mg, 1.14 mmol) in DCM (30 mL), was added trifluoroacetic acid (3.42 mL, 3 ml/mmol) and the reaction mixture was stirred for 2 h. After the completion of the reaction as confirmed by TLC, excess of trifluoroacetic acid and DCM were removed in vacuo to afford 5,6-dihydro-4H-2,5,10b-triaza-benzo[e]azulene-3-carboxylic acid ethyl ester trifluoroacetate (295 mg, 93%) as a gummy solid which was used without any further purification for the next step.
ESIMS (m/z): 280.7 (M+Na), 258.3 (M+1).

Step 3: Preparation of (R)-5-[3-tert-butoxycarbonylamino-4-(2,4,5-trifluoro-phenyl)-butyryl]-5,6-dihydro-4H-2,5,10b-triaza-benzo[e]azulene-3-carboxylic acid ethyl ester To a solution of (R)-3-[(tert-butoxycarbonyl)amino]-4-(2, 4,5-trifluoro-phenyl)butanoic acid (80 mg, 0.26 mmol) in dry DCM (15 mL), was added HOBT (42 mg, 0.31 mmol); EDC (60 mg, 0.31 mmol) and DIPEA (0.21 mL, 1.21 mmol) and the reaction mixture was stirred for 10 min. 5,6-Dihydro-4H-2,5,10b-triaza-benzo[e]azulene-3-carboxylic acid ethyl ester trifluoroacetate (98 mg, 0.26 mmol) in DCM (5 mL) was added and the reaction was stirred at r.t. overnight under nitrogen atmosphere. After the completion of the reaction, as confirmed by TLC, the crude product was extracted with DCM (10 mL) and washed with 10% HCl solution (10 mL) and saturated sodium bicarbonate solution (10 mL) sequentially. The organic layer was separated, washed with water, dried over Na$_2$SO$_4$ and concentrated in vacuo to afford the crude compound, which was purified by column chromatography (silica gel, 3:7 EtOAc:Pet.Ether) to afford (R)-5-[3-tert-butoxycarbonylamino-4-(2,4,5-trifluoro-phenyl)-butyryl]-5,6-dihydro-4H-2,5,10b-triaza-benzo[e]azulene-3-carboxylic acid ethyl ester (105 mg, 77%) as a viscous oil.
ESIMS (m/z): 596.0 (M+Na), 573.9 (M+1)

Step 4: Preparation of trifluoroacetic acid salt of 5-[(R)-3-amino-4-(2,4,5-trifluoro-phenyl)-butyryl]-5,6-dihydro-4H-2,5,10b-triaza-benzo[e]azulene-3-carboxylic acid ethyl ester To a solution of (R)-5-[3-tert-butoxycarbonylamino-4-(2,4,5-trifluoro-phenyl)-butyryl]-5,6-dihydro-4H-2,5,10b triaza-benzo[e]azulene-3-carboxylic acid ethyl ester (100 mg, 0.174 mmol) in DCM (5 mL), was added trifluoroacetic acid (0.52 mL, 3 mL/mmol). The reaction mixture was stirred at r.t. for 1 h. After completion of the reaction, as confirmed by TLC, excess of trifluoroacetic acid and DCM were evaporated in vacuo to afford a gummy solid which was crystallised from hexane to afford trifluoroacetic acid salt of 5-[(R)-3-amino-4-(2,4,5-trifluoro-phenyl)-butyryl]-5,6-dihydro-4H-2,5,10b-triaza-benzo[e]azulene-3-carboxylic acid ethyl ester (80 mg, 79%).

$^1$H NMR (400 MHz, MeOD): δ 1.39 (t, J=4.0 Hz, 3H), 2.80-3.06 (m, 2H), 3.05-3.14 (m, 2H), 3.90 (m, 1H), 4.35 (q, J=4.0 Hz, 2H), 4.43-4.62 (m, 3H), 4.77-5.01 (m, 1H), 7.19-7.26 (m, 1H), 7.31-7.37 (m, 1H), 7.51-7.61 (m, 2H), 7.62-7.72 (m, 21H), 8.25 (s, 1H)

ESIMS (m/z): 495.8 (M+Na), 473.5 (M+1)

Example 11

Preparation of trifluoroacetic acid salt of 5-[(R)-3-amino-4-(2,4,5-trifluoro-phenyl)-butyryl]-5,6-dihydro-4H-2,5,10b-triaza-benzo[e]azulene-3-carboxylic acid

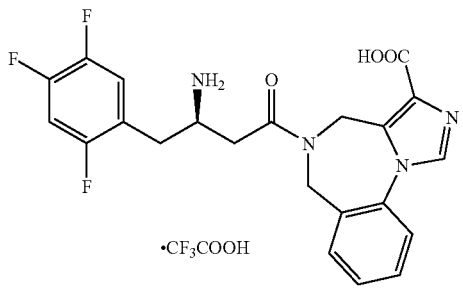 [SMILES: N[C@@H](CC(=O)N1Cc2ccccc2-n2cnc(C(=O)O)c2C1)Cc1cc(F)c(F)cc1F ; "·CF3COOH"]

Step 1: Preparation of 5-[3-tert-butoxycarbonylamino-4-(2,4,5-trifluoro-phenyl)-butyryl]-5,6-dihydro-4H-2,5,10b-triaza-benzo[e]azulene-3-carboxylic acid To a solution of 5-[3-tert-butoxycarbonylamino-4-(2,4,5-trifluoro-phenyl)-butyryl]-5,6-dihydro-4H-2,5,10b-triaza-benzo[e]azulene-3-carboxylic acid ethyl ester (100 mg, 0.17 mmol) in THF (5 mL) and water (5 mL), was added lithium hydroxide (43 mg, 1.03 mmol). The reaction mixture was stirred at r.t. overnight. After the completion of the reaction as confirmed by TLC, the reaction mixture was cooled to 0° C. and neutralized with 10% HCl solution to pH~4. The compound was extracted with ethylacetate (15 mL). The organic layer was washed with water, separated, dried over Na$_2$SO$_4$ and concentrated in vacuo to afford 5-[3-tert-butoxycarbonylamino-4-(2,4,5-trifluoro-phenyl)-butyryl]-5,6-dihydro-4H-2,5,10b-triaza-benzo[e]azulene-3-carboxylic acid (85 mg, 89%) as a viscous gel which was used without further purification for the next step.

ESIMS (m/z): 568.0 (M+Na), 546.0 (M+2)

Step 2: Preparation of trifluoroacetic acid salt or 5-[(R)-3-amino-4-(2,4,5-trifluoro-phenyl)-butyryl]-5,6-dihydro-4H-2,5,10b triaza-benzo[e]azulene-3-carboxylic acid To a solution of (R)-5-[3-tert-butoxycarbonylamino-4-(2,4,5-trifluoro-phenyl)butyryl]-5,6-dihydro-4H-2,5,10b-triaza-benzo[e]azulene-3-carboxylic acid (35 mg, 0.06 mmol) in dry DCM (5 mL), was added trifluoroacetic acid (6.18 mL, 3 mL/mmol). The reaction mixture was stirred at r.t. for 1 h. After the completion of the reaction as confirmed by TLC, excess of trifluoroacetic acid and DCM were evaporated in vacuo to afford a gummy solid was crystallised from hexane to afford trifluoroacetic acid salt of 5-[(R)-3-amino-4-(2,4,5-trifluoro-phenyl)-butyryl]-5,6-dihydro-4H-2,5,10b-triaza-benzo[e]azulene-3-carboxylic acid (28 mg, 78%).

$^1$H NMR (400 MHz, DMSO): δ 2.80-2.99 (m, 4H), 3.72-3.80 (m, 2H), 4.31-5.01 (m, 3H), 7.49-7.54 (m, 3H), 7.71-7.73 (m, 2H), 7.92-7.95 (M, 2H)

ESIMS (m/z): 443.8 (M−1)

Example 12

Preparation of trifluoroacetic acid salt of (R)-3-amino-1-[3-(pyrrolidine-1-carbonyl)-4H,6H-2,5,10b-triaza-benzo[e]azulen-5-yl]-4-(2,4,5-trifluoro-phenyl)-butan-1-one

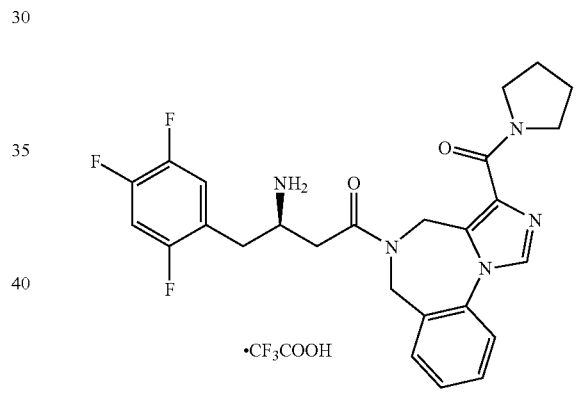

Step 1: Preparation of (R)-[3-oxo-3-[3-(pyrrolidine-1-carbonyl)-4H,6H-2,5,10b-triaza-benzo[e]azulen-5-yl]-1-(2,4,5-trifluoro-benzyl)-propyl]-carbamic acid tert-butyl ester To a solution of (R)-5-[3-tert-butoxycarbonylamino-4-(2,4,5-trifluoro-phenyl)-butyryl]-5,6-dihydro-4H-2,5,10b-triaza-benzo[e]azulene-3-carboxylic acid (60 mg, 0.11 mmol) in dry DCM (15 mL), was added HOBT (19 mg, 0.14 mmol), EDC (27 mg, 0.14 mmol) and DIPEA (0.08 mL; 0.46 mmol) and the reaction mixture was stirred for 10 min. Pyrrolidine (0.02 mL, 0.24 mmol) was added and the reaction was stirred at r.t. overnight under nitrogen atmosphere. After the completion of the reaction, as confirmed by TLC, the crude product was extracted with DCM (15 mL) and washed with 10% HCl solution (10 mL) and saturated sodium bicarbonate solution (10 mL). The organic layer was separated washed with water, dried over Na$_2$SO$_4$ and concentrated in vacuo to afford the crude compound, which was purified by column chromatography (silica gel, 3:7 to 9:1 EtOAc:Pet.Ether) to afford (R)-[3-oxo-3-[3-(pyrrolidine-1-carbonyl)-

4H,6H-2,5,10b-triaza-benzo[e]azulen-5-yl]-1-(2,4,5-trifluoro-benzyl)-propyl]-carbamic acid tert-butyl ester (55 mg, 83%) as a solid.

ESIMS (m/z): 621.0 (M+Na), 599.0 (M+1)

Step 2: Preparation of trifluoroacetic acid salt of (R)-3-amino-1-[3-(pyrrolidine-1-carbonyl)-4H,6H-2,5,10b-triaza-benzo[e]azulen-5-yl]-4-(2,4,5-trifluoro-phenyl)-butan-1-one To solution of (R)-[3-oxo-3-[3-(pyrrolidine-1-carbonyl)-4H,6H-2,5,10b-triaza-benzo-[e]azulen-5-yl]-1-(2,4,5-trifluoro-benzyl)-propyl]-carbamic acid tert-butyl ester (45 mg, 0.08 mmol) in DCM (5 mL) was added trifluoroacetic acid (0.24 mL, 3 mL/mmol). The reaction mixture was stirred at r.t. for 1 h. After the completion of the reaction, as confirmed by TLC, excess of trifluoroacetic acid and DCM were evaporated in vacuo to afford a gummy solid which was crystallized from hexane to afford trifluoroacetic acid salt of (R)-3-amino-1-[3-(pyrrolidine-1-carbonyl)-4H,6H-2,5,10b-triaza-benzo[e]azulen-5-yl]-4-(2,4,5-trifluoro-phenyl)-butan-1-one (40 mg, 86%)

$^1$H NMR (400 MHz, MeOD): δ 1.98-2.02 (m, 4H), 2.97-3.11 (m, 4H), 3.62 (t. J=6.0 Hz, 2H), 3.92-4.05 (m, 3H), 4.41-4.87 (m, 4H), 7.19-7.26 (m, 1H), 7.31-7.37 (m, 1H), 7.51-7.61 (m, 2H), 7.62-7.72 (m, 2H), 8.17 (s, 1H)

ESIMS (m/z): 520.1 (M+Na), 498.6 (M+1)

The compounds listed in Tables 6 to 9 were prepared essentially following the procedures described for Examples 1 to 12:

TABLE 6

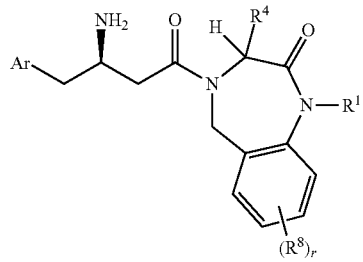

| Example No. | Ar | R$^1$ | R$^4$ | R$^8$ | ESIMS (m/z) |
| --- | --- | --- | --- | --- | --- |
| 13 | 2,5-difluorophenyl | H | H | H | 382.1 (M + Na), 359.8 (M + 1) |
| 14 | 2,4,5-trifluorophenyl | H | H | 8-Cl | 434.1 (M + Na), 412.0 (M + 1) |
| 15 | 2,4,5-trifluorophenyl | H | H | 7-OCH$_3$ | 430.3 (M + Na), |
| 16 | 2,4,5-trifluorophenyl | H | H | 8-F | 418.2 (M + Na), 396.0 (M + 1) |

TABLE 6-continued

| Example No. | Ar | R¹ | R⁴ | R⁸ | ESIMS (m/z) |
|---|---|---|---|---|---|
| 17 | 2,4,5-trifluorophenyl | H | H | 7-F | 396.8 (M + 1) |
| 18 | 2,4,5-trifluorophenyl | H | —CH₃ | H | 392.2 (M + 1) |
| 19 | 2,4,5-trifluorophenyl | H | —CH₂CH(CH₃)₂ | H | 434.4 (M + 1) |
| 20 | 2,4,5-trifluorophenyl | H | —CH₂Ph | H | 468.5 (M + 1) |
| 21 | 2,4,5-trifluorophenyl | H | —CH₂-C₆H₄-OH (4-OH) | H | 484.4 (M + 1) |
| 22 | 2,4,5-trifluorophenyl | —CH₃ | H | 8-F | 432.3 (M + Na), 410.9 (M + 1) |

TABLE 6-continued
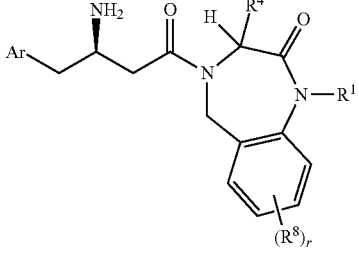
| Example No. | Ar | R¹ | R⁴ | R⁸ | ESIMS (m/z) |
|---|---|---|---|---|---|
| 23 | 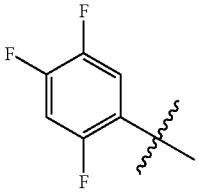 [SMILES: *c1cc(F)c(F)cc1F] |  | H | H | 406.4 (M + 1) |
| 24 | 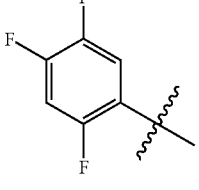 |  | H | 8-F | 446.2 (M + Na), 423.8 (M + 1) |
| 25 | 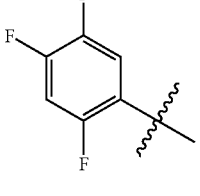 | 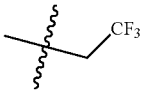 | H | H | 482.2 (M + Na), 460.3 (M + 1) |
| 26 | 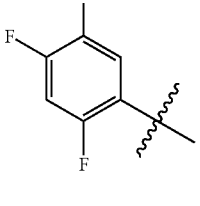 | 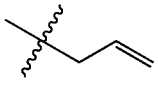 | H | H | 440.3 (M + Na), 417.7 (M + 1) |
| 27 | 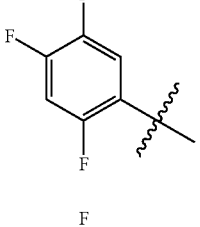 |  | H | H | 454.4 (M + Na), 432.4 (M + 1) |
| 28 | 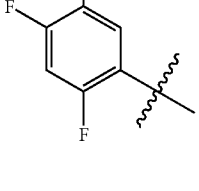 | 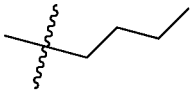 [SMILES: *CCCC] | H | H | 456.4 (M + Na), |

TABLE 6-continued

| Example No. | Ar | R¹ | R⁴ | R⁸ | ESIMS (m/z) |
|---|---|---|---|---|---|
| 29 | 2,4,5-trifluorophenyl | benzyl | H | H | 490.3 (M + Na), 468.1 (M + 1) |
| 30 | 2,4,5-trifluorophenyl | phenethyl | H | H | 504.4 (M + Na), 482.0 (M + 1) |
| 31 | 2,4,5-trifluorophenyl | 2-(trifluoromethyl)benzyl | H | H | 558.3 (M + Na), 536.3 (M + 1) |
| 32 | 2,4,5-trifluorophenyl | 4-methoxybenzyl | H | H | 521.2 (M + Na), 499.4 (M + 1) |
| 33 | 2,4,5-trifluorophenyl | 2-cyanobenzyl | H | H | 15.3 (M + Na), 492.8 (M+) |
| 34 | 2,4,5-trifluorophenyl | 2,4,5-trifluorobenzyl | H | H | 544.2 (M + Na), 521.9 (M + 1) |

TABLE 6-continued

| Example No. | Ar | R¹ | R⁴ | R⁸ | ESIMS (m/z) |
|---|---|---|---|---|---|
| 35 | 2,4,5-trifluorophenyl | -CH₂C(CH₃)₂-C(O)OEt | H | H | 486.3 (M + Na), 463.9 (M + 1) |
| 36 | 2,4,5-trifluorophenyl | -CH₂C(CH₃)₂-C(O)NH-iPr | H | H | 499.4 (M + Na), |
| 37 | 2,4,5-trifluorophenyl | -CH₂C(CH₃)₂-C(O)NH-tBu | H | H | 513.3 (M + Na), |
| 38 | 2,4,5-trifluorophenyl | -CH₂C(CH₃)₂-C(O)NH-cyclopropyl | H | 8-F | 515.2 (M + Na), 493.3 (M + 1) |
| 39 | 2,4,5-trifluorophenyl | -CH₂C(CH₃)₂-C(O)N(CH₃)-cyclopropyl | H | H | 511.3 (M + Na), |
| 40 | 2,4,5-trifluorophenyl | -CH₂C(CH₃)₂-C(O)NH-CH₂-(4-OCH₃-phenyl) | H | H | 577.3 (M + Na), 555.4 (M + 1) |

TABLE 6-continued
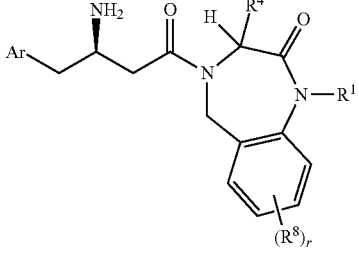
| Example No. | Ar | R¹ | R⁴ | R⁸ | ESIMS (m/z) |
|---|---|---|---|---|---|
| 41 | 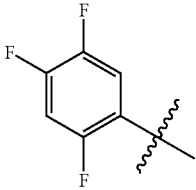 [SMILES: *c1cc(F)c(F)cc1F] | 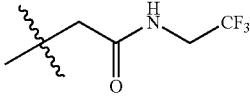 [SMILES: *CC(=O)NCC(F)(F)F] | H | H | 539.3 (M + Na), 517.1 (M + 1) |
| 42 | 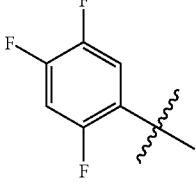 | 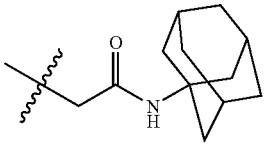 [SMILES: *CC(=O)NC12CC3CC(CC(C3)C1)C2] | H | H | 591.4 (M + Na), 569.0 (M + 1) |
| 43 | 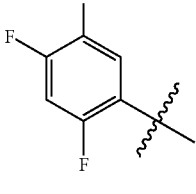 | 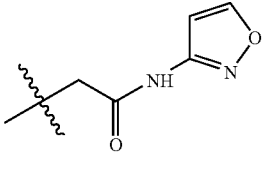 [SMILES: *CC(=O)Nc1ccon1] | H | H | 524.3 (M + Na), |
| 44 | 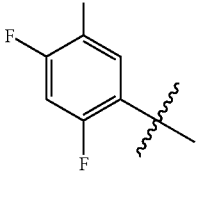 | 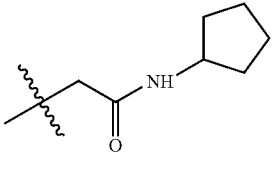 [SMILES: *CC(=O)NC1CCCC1] | H | H | 525.3 (M + Na), 503.3 (M + 1) |
| 45 | 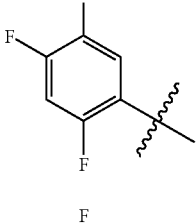 | 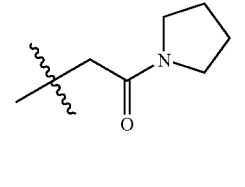 [SMILES: *CC(=O)N1CCCC1] | H | H | 511.3 (M + Na), 489.1 (M + 1) |
| 46 | 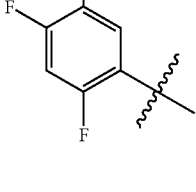 | 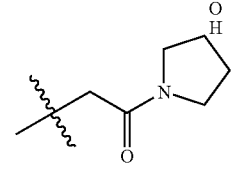 [SMILES: *CC(=O)N1CCCC1] | H | H | 527.0 (M + Na), 505.1 (M + 1) |

TABLE 6-continued
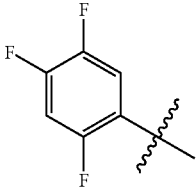 [SMILES: *c1cc(F)c(F)cc1F]
| Example No. | Ar | R¹ | R⁴ | R⁸ | ESIMS (m/z) |
|---|---|---|---|---|---|
| 47 | 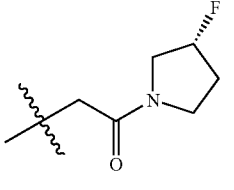 [SMILES: *CC(=O)N1CC[C@@H](F)C1] | 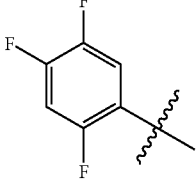 | H | H | 529.3 (M + Na), |
| 48 | 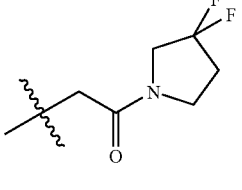 | 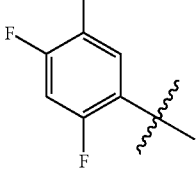 | H | H | 547.3 (M + Na), 525.2 (M + 1) |
| 49 | 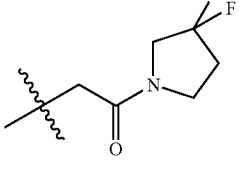 | 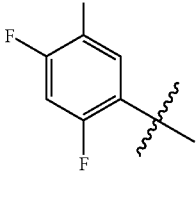 | H | 8-F | 565.4 (M + Na), 542.8 (M + 1) |
| 50 | 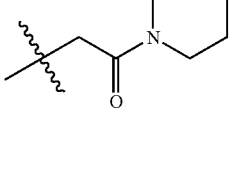 | 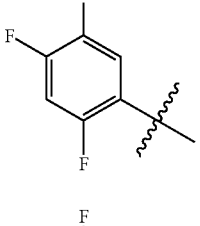 | H | H | 525.3 (M + Na), 503.8 (M + 1) |
| 51 | 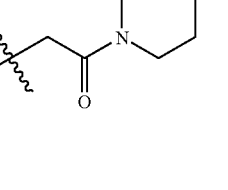 | 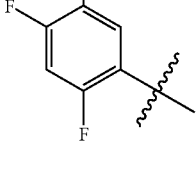 | H | H | 539.4 (M + Na), 517.3 (M + 1) |
| 52 | 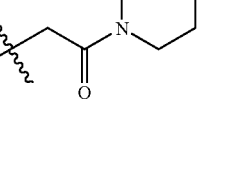 | | H | H | 543.4 (M + Na), 521.4 (M + 1) |

TABLE 6-continued

| Example No. | Ar | R¹ | R⁴ | R⁸ | ESIMS (m/z) |
|---|---|---|---|---|---|
| 53 | 2,4,5-trifluorophenyl | 4,4-difluoropiperidinyl-acetyl (gem-dimethyl) | H | H | 561.4 (M + Na), 539.3 (M + 1) |
| 54 | 2,4,5-trifluorophenyl | morpholinyl-acetyl (gem-dimethyl) | H | H | 527.2 (M + Na), 505.2 (M + 1) |
| 55 | 2,4,5-trifluorophenyl | 2,3-dihydro-1,4-benzoxazin-4-yl-acetyl (gem-dimethyl) | H | H | 553.4 (M + Na), 553.4 (M + 1) |
| 56 | 2,4,5-trifluorophenyl | thiomorpholinyl-acetyl (gem-dimethyl) | H | H | 543.2 (M + Na), 520.9 (M + 1) |
| 57 | 2,4,5-trifluorophenyl | 1,2,3,4-tetrahydroisoquinolin-2-yl-acetyl (gem-dimethyl) | H | H | 573.4 (M + Na), 551.1 (M + 1) |
| 58 | 2,4,5-trifluorophenyl | 6,7-dimethoxy-1,2,3,4-tetrahydroisoquinolin-2-yl-acetyl (gem-dimethyl) | H | H | 633.4 (M + Na), 610.9 (M + 1) |

TABLE 7
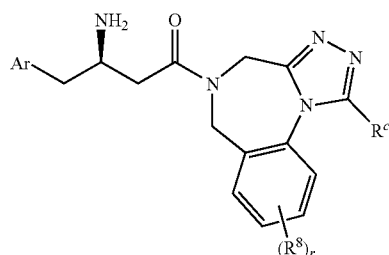
| Example No. | Ar | R⁸ | Rᶜ | ESIMS (m/z) |
|---|---|---|---|---|
| 59 | 2,4,5-trifluorophenyl | H | H | 424.3 (M + Na), 401.8 (M + 1) |
| 60 | 2,4,5-trifluorophenyl | 8-F | H | 420.5 (M + 1) |
| 61 | 2,4,5-trifluorophenyl | 8-F, 9-F | H | 460.2 (M + Na), 438.2 (M + 1) |
| 62 | 2,4,5-trifluorophenyl | H | —CF₃ | 492.9 (M + Na), 470.3 (M + 1) |
| 63 | 2,4,5-trifluorophenyl | H | —CH₃ | 416.1 (M + 1) |
| 64 | 2,4,5-trifluorophenyl | 9-F | —CH₃ | 456.3 (M + Na), 434.8 (M + 1) |

TABLE 7-continued
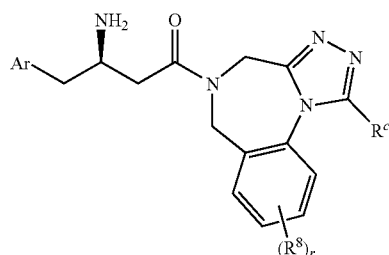
| Example No. | Ar | R⁸ | Rᶜ | ESIMS (m/z) |
|---|---|---|---|---|
| 65 | 2,4,5-trifluorophenyl | H | —CH₂CH₃ | 452.4 (M + Na), 429.8 (M + 1) |
| 66 | 2,4,5-trifluorophenyl | H | —CH₂F | 456.6 (M + Na), 434.7 (M + 1) |
| 67 | 2,4,5-trifluorophenyl | H | —CHF₂ | 474.3 (M + Na), 452.3 (M + 1) |
| 68 | 2,4,5-trifluorophenyl | H | —C(CH₃)₃ | 480.3 (M + Na), |
| 69 | 2,4,5-trifluorophenyl | H | cyclopropyl | 464.4 (M + Na, 442.1 (M + 1) |
| 70 | 2,4,5-trifluorophenyl | H | —Ph | 500.6 (M + Na), 478.3 (M + 1) |

TABLE 7-continued
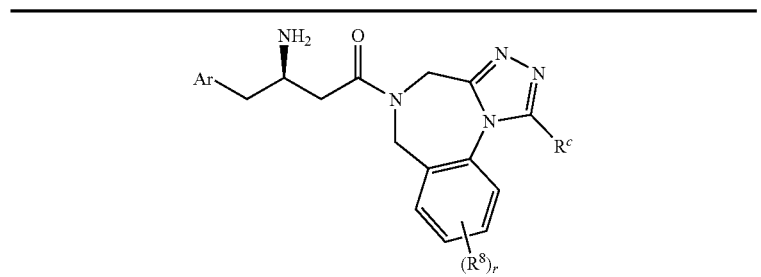
| Example No. | Ar | $R^8$ | $R^c$ | ESIMS (m/z) |
|---|---|---|---|---|
| 71 | 2,4,5-trifluorophenyl | 9-Cl | H | 458.3 (M + Na), 436.5 (M + 1) |
| 72 | 2,4,5-trifluorophenyl | H | 2-methoxyphenyl | 530.3 (M + Na), 507.9 (M + 1) |
TABLE 8
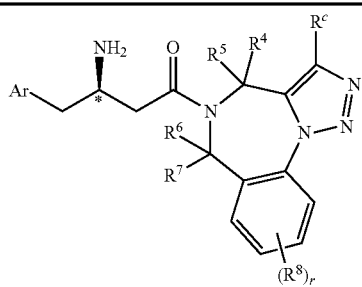
| Example No. | Ar | $R^8$ | $R^c$ | ESIMS (m/z) |
|---|---|---|---|---|
| 73 | 2,4,5-trifluorophenyl | 8-OCH$_3$ | H | 454.3 (M + Na), 432.8 (M + 1) |
| 74 | 2,4,5-trifluorophenyl | 9-F | H | 442.2 (M + Na), 420.6 (M + 1) |

TABLE 8-continued
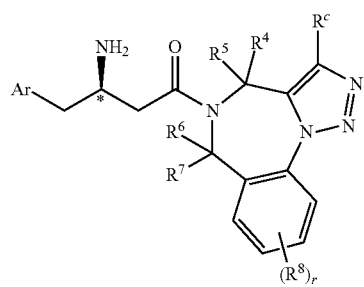
| Example No. | Ar | R⁸ | R^c | ESIMS (m/z) |
|---|---|---|---|---|
| 75 | 2,4,5-trifluorophenyl | H | phenyl | 500.9 (M + Na), 5478.6 (M + 1) |
| 76 | 2,4,5-trifluorophenyl | H | 2-methoxyphenyl | 530.9 (M + Na), 508.6 (M + 1) |
| 77 | 2,4,5-trifluorophenyl | H | CH₂OCH₃ | 468.8 (M + Na), 446.8 (M + 1) |
| 78 | 2,4,5-trifluorophenyl | H | CH₂F | 456.4 (M + Na), 434.4 (M + 1) |
| 79 | 2,4,5-trifluorophenyl | H | CHF₂ | 452.8 (M + 1) |

TABLE 9
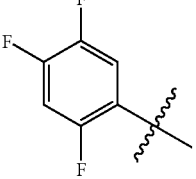
| Example No. | Ar | R⁸ | R$^c$ | ESIMS (m/z) |
|---|---|---|---|---|
| 80 | 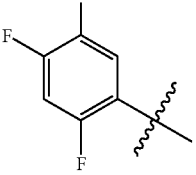 | 9-F | —COOEt | 513.9 (M + Na), 491.9 (M + 1) |
| 81 | 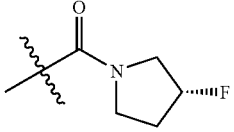 [SMILES: *C(=O)N1CC[C@@H](F)C1] | H | 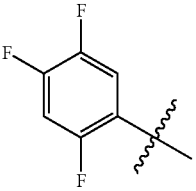 [SMILES: *c1cc(F)c(F)cc1F] | 538.9 (M + Na), 516.5 (M + 1) |
| 82 | 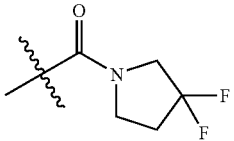 [SMILES: *C(=O)N1CCC(F)(F)C1] | H | 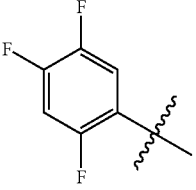 [SMILES: *c1cc(F)c(F)cc1F] | 556.8 (M + Na), 534.9 (M + 1) |
| 83 | 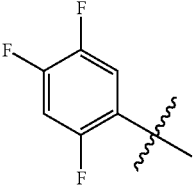 [SMILES: *c1cc(F)c(F)cc1F] | H | —CONH$_2$ | 466.8 (M + Na), 444.6 (M + 1) |
| 84 | 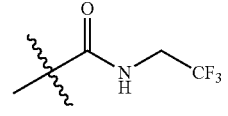 [SMILES: *C(=O)NCC(F)(F)F] | H | 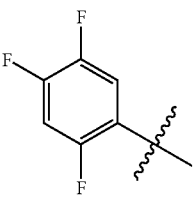 [SMILES: *c1cc(F)c(F)cc1F] | 549.0 (M + Na), 526.8 (M + 1) |
| 85 | 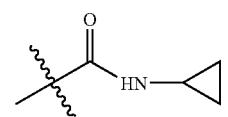 [SMILES: *C(=O)NC1CC1] | H |  | 506.9 (M + Na), 484.7 (M + 1) |

TABLE 9-continued

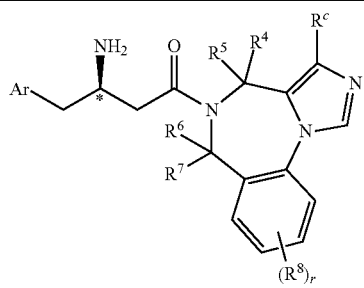

| Example No. | Ar | R⁸ | Rᶜ | ESIMS (m/z) |
|---|---|---|---|---|
| 86 | 2,4,5-trifluorophenyl | H | 2-methyl-1-morpholino-1-oxopropan-2-yl | 536.9 (M + Na), 514.4 (M + 1) |
| 87 | 2,4,5-trifluorophenyl | H | N,N-diethyl-2-methylpropanamide | 522.9 (M + Na), 500.6 (M + 1) |
| 88 | 2,4,5-trifluorophenyl | H | N-(2-(trifluoromethyl)benzyl)-2-methylpropanamide | 624.9 (M + Na), 602.9 (M + 1) |
| 89 | 2,4,5-trifluorophenyl | H | 1-(4,4-difluoropiperidin-1-yl)-2-methylpropan-1-one | 548.2 (M + 1) |
| 90 | 2,4,5-trifluorophenyl | 9-F | 2-methyl-1-morpholino-1-oxopropan-2-yl | 555.0 (M + Na), 532.4 (M + 1) |
| 91 | 2,4,5-trifluorophenyl | 8-F | 2-methyl-1-morpholino-1-oxopropan-2-yl | 550.0 (M + Na), 532.6 (M + 1) |

TABLE 9-continued

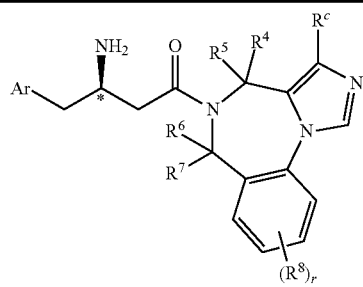

| Example No. | Ar | R⁸ | Rᶜ | ESIMS (m/z) |
|---|---|---|---|---|
| 92 | F (2,4,5-trifluorophenyl) | 8-F, 9-F | morpholine amide | 579.2 (M + Na), 550.5 (M + 1) |

In Vitro Studies

Protocol for In-Vitro DPP-IV Assay

DPP-IV activity was determined by the rate of cleavage of p-nitro aniline (pNA) from synthetic substrate Glycine-Proline-pNA. The assay was conducted by adding 1 μg of porcine kidney or human recombinant DPP-IV enzyme (Sigma Aldrich, USA) in 100 μL of the assay buffer (100 mM Tris, pH 7.4, 140 mM NaCl, 10 mM KCl, 1% BSA) to 96 well Cellstar flat bottom microtitre plates (Greiner Bio-one, Germany). The reaction was initiated by adding 80 μl of 500 μM substrate Gly-Pro-pNA. The incubation was carried out in the kinetic mode at 30° C. for 30 min. Absorbance was measured using Synergy HT Biotek Multiplate reader at 410 nm. Test compounds and solvent controls were added as 10 μL additions. A standard curve of free p-nitro, aniline (pNA) was generated using 0-2000 μM pNA in the assay buffer. In addition DPP-IV activity was also determined by using Fluorogenic substrate (Gly-Pro-AMC) using human recombinant DPP-IV enzyme (Sigma Aldrich USA).

Tests for $IC_{50}$ Studies:

Test compounds dissolved in DMSO at 9-10 different concentrations were tested in triplicates along with the solvent control and blank samples. % age inhibition was calculated at each concentration with respect to the solvent control (no test compound added). $IC_{50}$ values were calculated from 3 experiments using the Graph Pad Prism or Sigma Stat software.

TABLE 10

| S. No. | Compound No. | % Inhibition |
|---|---|---|
| 1 | 2 | Y |
| 2 | 3 | Y |
| 3 | 16 | Y |
| 4 | 19 | Y |
| 5 | 24 | X |
| 6 | 27 | Y |
| 7 | 28 | Y |
| 8 | 39 | Y |
| 9 | 34 | Y |
| 10 | 38 | Y |
| 11 | 50 | Y |
| 12 | 52 | Y |

TABLE 10-continued

| S. No. | Compound No. | % Inhibition |
|---|---|---|
| 13 | 53 | Y |
| 14 | 59 | Y |
| 15 | 62 | Y |
| 16 | 65 | Y |
| 17 | 70 | Y |
| 18 | 76 | Y |
| 19 | 77 | X |
| 20 | 78 | Y |
| 21 | 86 | Y |
| 22 | 88 | Y |
| 23 | 89 | Y |
| 24 | 95 | Y |

X: 0-49% DPP-IV inhibition at 100 nM
Y: 50-100% DPP-IV inhibition at 100 nM

TABLE 11

| S. No. | Compound No. | $IC_{50}$ (nM) |
|---|---|---|
| 1 | 2 | A |
| 2 | 3 | A |
| 3 | 19 | A |
| 4 | 28 | A |
| 5 | 34 | A |
| 6 | 38 | A |
| 7 | 52 | A |
| 8 | 53 | A |
| 9 | 76 | A |
| 10 | 78 | A |
| 11 | 86 | A |
| 12 | 95 | A |

A: $IC_{50}$ value is 1-100 nM

In Vivo Studies

Oral Glucose Tolerance Test (OGTT) in C57BL/6J Mice

The oral glucose tolerance test (OGTT) measures the body's ability to use glucose that is the body's main source of energy. OGTT serves as a primary in-vivo screen to select efficacious test compounds for their antidiabetic activity. Compounds were formulated in 0.25% CMC with a drop of tween 80 (optional). C57BL/6J male mice (8-9 weeks) were fasted overnight and randomized into different groups (n=6) on body weigh basis. At $T_{-15}$ min blood was collected from each group for glucose estimation. At $T_0$ compounds or vehicle were administered with simultaneous administration of glucose (2 g/kg p.o.) to each group. RO water was administered to no glucose control group. Blood samples were collected from retro-orbital plexus at 15, 30, 60 and 120 min post dosing for glucose estimation. The AUC for glucose was calculated to get the reduction in glucose excursion.

TABLE 12

| S. No. | Compound No. | % Reduction in glucose excursion* | $ED_{50}$ (mg/kg p.o.) |
|---|---|---|---|
| 1. | 2 | 51% | 0.4 |
| 2. | 3 | 37% | 0.7 |

*OGTT in C57BL/6J mice at 3 mg/kg body weight

The invention claimed is:
1. A compound of Formula I,

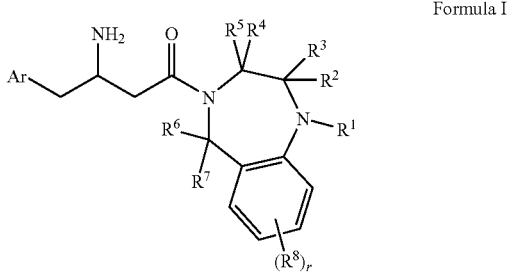

Formula I or a pharmaceutically acceptable salt or a stereoisomer thereof, wherein:

Ar represents phenyl; which may further be unsubstituted or may be optionally substituted at any available position by one or more substituents selected from halogen, CN, hydroxyl, $NH_2$, $C_{1-12}$ alkyl or $C_{1-12}$ alkoxy;

$R^1$ is selected from the group consisting of $(CH_2)_n CONR^a R^b$, $(CH_2)_n COOR^a$, $(CH_2)_n NR^a R^b$, $(CH_2)_n NR^a COR^b$, $(CH_2)_n C(=L)R^a$ (wherein L is O or S), $(CH_2)_n OR^a$ (wherein each methylene group may be substituted by one or more halogen atoms), —(CO)$R^a$, —(CO)NR$^a$R$^b$, hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, $C_{6-10}$ aryl, heteroaryl, $(CH_2)_n$—$C_{3-8}$ cycloalkyl, $(CH_2)_n$-heterocyclyl, $(CH_2)_n$-aryl, $(CH_2)_n$-heteroaryl, each of which may be optionally substituted at any available position by one or more substituents selected from hydrogen, halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, oxo, —OR$^a$, —SR$^a$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, $C_{3-8}$ cycloalkyl, S(O)$_m$R$^a$, SO$_2$NR$^a$R$^b$; cycloalkyl which may be optionally substituted at any available position by one or more substituents independently selected from R$^c$ or R$^{c'}$; aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

$R^2$ and $R^3$ together represents a single oxygen or sulphur atom which is linked to the diazepine ring by a double bond; or $R^1$ and $R^2$ together forms a double bond in the diazepine ring and $R^3$ represents the group —NR$^a$R$^b$; or $R^1$ and $R^3$ together with the nitrogen atom to which $R^1$ is attached forms a heterocyclic or heteroaryl ring which may additionally contain from one to three heteroatoms independently selected from O, S and N; the ring formed may optionally be substituted with one or more substituents selected from R$^c$ or R$^{c'}$ and R$^2$ represent hydrogen or a double bond;

$R^4$ and $R^5$ are independently selected from the group consisting of hydrogen, halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, —OR$^a$, —SR$^a$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, $C_{3-8}$ cycloalkyl, S(O)$_m$R$^a$, SO$_2$NR$^a$R$^b$; cycloalkyl which may be optionally substituted at any available position by one or more substituents independently selected from R$^c$ or R$^{c'}$; $C_{6-10}$ aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

$R^6$ and $R^7$ are independently selected from the group consisting of hydrogen, halogen, CN, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{2-12}$ haloalkenyl, $C_{2-12}$ haloalkynyl, $C_{1-12}$ alkylcarbonyl, $C_{1-12}$ alkoxycarbonyl, —OR$^a$, —SR$^a$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, $C_{3-8}$ cycloalkyl, S(O)$_m$R$^a$, SO$_2$NR$^a$R$^b$; $C_{3-8}$ cycloalkyl which may be optionally substituted at any available position by one or more substituents independently selected from R$^c$ or R$^{c'}$; $C_{6-10}$ aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

$R^8$ is independently selected from hydrogen, halogen, CN, $C_{1-12}$ alkyl, $C_{1-12}$ haloalkyl, $C_{1-12}$ alkoxy, $C_{1-12}$ haloalkoxy, $C_{2-12}$ haloalkenyl, $C_{1-12}$ alkylcarbonyl, $C_{1-12}$ alkoxycarbonyl, —OR$^a$, —SR$^a$, —CF$_3$, —OCF$_3$, —NO$_2$, —NR$^a$R$^b$, N(R$^a$)(CO)R$^b$, N(R$^a$)(CO)OR$^b$, N(R$^a$)(CO)NR$^a$R$^b$, —(CO)R$^a$, —(CO)NR$^a$R$^b$, —O(CO)R$^a$, —O(CO)NR$^a$R$^b$, —COOR$^a$, C$_{3-6}$ cycloalkyl, S(O)$_m$R$^a$, SO$_2$NR$^a$R$^b$; C$_{3-8}$ cycloalkyl which may be optionally substituted at any available position by one or more substituents independently selected from R$^c$ or R$^{c'}$; C$_{6-10}$ aryl which may be optionally substituted at any available position by one or more substituents independently selected from R$^c$ or R$^{c'}$; heteroaryl which may be optionally substituted at any available position by one or more substituents independently selected from R$^c$ or R$^{c'}$; or heterocyclyl which may be optionally substituted at any available position by one or more substituents independently selected from R$^c$ or R$^{c'}$;

R$^a$ and R$^b$ are independently selected from hydrogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-8}$ cycloalkyl, heterocyclyl, C$_{6-10}$ aryl, heteroaryl, (CH$_2$)$_n$-cycloalkyl, (CH$_2$)$_n$-heterocyclyl, (CH$_2$)$_n$-aryl, (CH$_2$)$_n$-heteroaryl; each of which may be optionally substituted with halogen, hydroxyl, C$_{1-12}$ alkyl, C$_{2-12}$ alkenyl, C$_{2-12}$ alkynyl, C$_{1-12}$ alkoxy, C$_{1-12}$ alkylcarbonyl, C$_{1-12}$ alkoxycarbonyl, C$_{3-8}$ cycloalkyl, C$_{1-12}$ haloalkyl, C$_{1-12}$ haloalkoxy, C$_{2-12}$ haloalkenyl, C$_{6-10}$ aryl, heterocyclyl, heteroaryl, (CH$_2$)$_n$-aryl, (CH$_2$)$_n$-heterocyclyl, (CH$_2$)$_n$-heteroaryl, (CH$_2$)$_n$-cycloalkyl, oxo, —CN, —OR$^9$, —NO$_2$, —NR$^9$R$^{10}$, N(R$^9$)(CO)R$^{10}$, N(R$^9$)(CO)OR$^{10}$, N(R$^9$)(CO)NR$^9$R$^{10}$, —C(=L)R (wherein L is O or S), —(CO)NR$^9$R$^{10}$, —O(CO)R$^9$, —O(CO)NR$^9$R$^{10}$, —COOR$^9$, —SR$^9$, S(O)$_m$R$^9$, SO$_2$NR$^9$R$^{10}$; SO$_3$H, NHSO$_2$R$^9$, P(O)R$^9$R$^{10}$; or R$^a$ and R$^b$ may be joined together along with the nitrogen atom to which they are attached to form a heterocyclic or heteroaryl ring which may additionally contain from one to three heteroatoms independently selected from O, S and N, the ring formed may optionally be substituted with one or more substituents selected from hydrogen, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-8}$ cycloalkyl, heterocyclyl, C$_{6-10}$ aryl, heteroaryl, (CH$_2$)$_n$-cycloalkyl, (CH$_2$)$_n$-heterocyclyl, (CH$_2$)$_n$-aryl, (CH$_2$)$_n$-heteroaryl, C$_{1-12}$ alkylcarbonyl, C$_{1-12}$ alkoxycarbonyl, oxo, CN, —OR$^9$, —CF$_3$, —OCF$_3$CH$_2$CF$_3$, CF$_2$CF$_3$, —NO$_2$, —NR$^9$R$^{10}$, N(R$^9$)(CO)R$^{10}$, N(R$^9$)(CO)OR$^{10}$, N(R$^9$)(CO)NR$^9$R$^{10}$, —C(=L)R$^9$ (wherein L is O or S), —(CO)NR$^9$R$^{10}$, —O(CO)C$_1$-C$_{12}$ alkyl, —O(CO)NR$^9$R$^{10}$, —COOR$^9$, —SR$^9$, S(O)$_m$R$^9$, SO$_2$NR$^9$R$^{10}$; SO$_3$H, NHSO$_2$R$^9$, P(O)R$^9$R$^{10}$; the ring thus formed may further be fused with 3 to 7 membered unsaturated or saturated ring, which may contain from one to three heteroatoms independently selected from O, S or N, the fused ring may optionally be substituted with one or more substituents R$^c$ or R$^{c'}$;

R$^c$ or R$^{c'}$ is independently selected from the group consisting of hydrogen, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{1-12}$ alkoxy, C$_{1-12}$ haloalkoxy, C$_{3-8}$ cycloalkyl, heterocyclyl, C$_{6-10}$ aryl, heteroaryl, (CH$_2$)$_n$-cycloalkyl, (CH$_2$)$_n$-heterocyclyl, (CH$_2$)$_n$-aryl, (CH$_2$)$_n$-heteroaryl, C$_{1-12}$ alkylcarbonyl, C$_{1-12}$ alkoxycarbonyl, CN, —OR$^9$, —OCF$_3$, —NO$_2$, =NOR$^{10}$, —NR$^9$R$^{10}$, N(R$^9$)(CO)R$^{10}$, N(R$^9$)(CO)OR$^{10}$, N(R$^9$)(CO)NR$^9$R$^{10}$, —C(=L)R$^9$ (wherein L is O or S), —(CO)NR$^9$R$^{10}$, —O(CO)R$^9$, —O(CO)NR$^9$R$^{10}$, —COOR$^9$, —SR$^9$, S(O)$_m$R$^9$, SO$_2$NR$^9$R$^{10}$; SO$_3$H, NHSO$_2$R$^9$, P(O)R$^9$R$^{10}$;

R$^9$ and R$^{10}$ are independently selected from hydrogen, C$_{1-12}$ alkyl, C$_{2-12}$ alkenyl, C$_{2-12}$ alkynyl, C$_{1-12}$ haloalkyl, C$_{2-12}$ haloalkenyl, C$_{3-8}$ cycloalkyl, heterocyclyl, C$_{6-10}$ aryl, heteroaryl, (CH$_2$)$_n$-cycloalkyl, (CH$_2$)$_n$-heterocyclyl, (CH$_2$)$_n$-aryl, (CH$_2$)$_n$-heteroaryl, each of which may be optionally substituted with halogen, hydroxyl or C$_{1-6}$ alkoxy, or R$^9$ and R$^{10}$ may be joined together to form a heterocyclic or heteroaryl ring, which may optionally be substituted with one or more substituents independently selected from R$^c$ or R$^{c'}$;

m represents 1 or 2;

n represents 1, 2, 3 or 4;

r represents 1, 2, 3 or 4;

wherein said heterocyclyl is chosen from oxazolidinyl, tetrahydrofuranyl, dihydrofuranyl, dihydropyridinyl, dihydroisooxazolyl, dihydrobenzofuryl, azabicyclohexyl, dihydroindonyl, piperidinyl, piperazinyl, morpholinyl, thiomorpholinyl, benzomorpholinyl, fluoropyrrolidinyl, difluoropyrrolidinyl, piperidinyl, fluoropiperidinyl, difluoropiperidinyl, piperidinonyl, hydroxy pyrrolidinyl, tetrahydroisoquinolinyl, dimethoxytetrahydroisoquinolinyl, and pyrrolidinyl; and wherein said heteroaryl is chosen from oxazolyl, imidazolyl, pyrrolyl, 1,2,3,-triazolyl, 1,2,4-triazolyl, tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, and benzoxazolyl.

2. The compound according to claim 1 having the Formula Ia, wherein

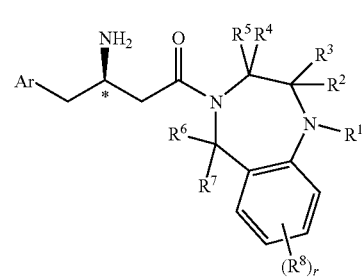

Formula Ia r, Ar, R$^1$, R$^2$, R$^3$, R$^4$, R$^5$, R$^6$, R$^7$ and R$^8$ are as defined in claim 1; or a pharmaceutically acceptable salt or a stereoisomer thereof.

3. The compound according to claim 1 having the Formula Ib, wherein

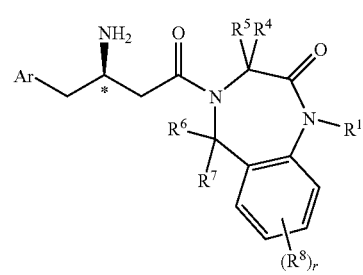

Formula Ib r, Ar, R$^1$, R$^4$, R$^5$, R$^6$, R$^7$ and R$^8$ are as defined in claim 1; or a pharmaceutically acceptable salt or a stereoisomer thereof.

4. The compound according to claim 1 having the Formula Ic, wherein

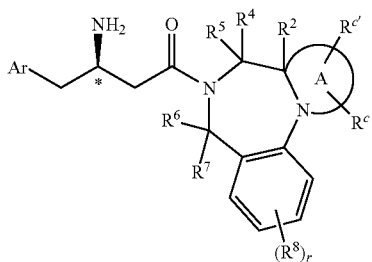

Formula Ic ring A is optionally substituted at any available position by one or more substituents independently selected from $R^c$ or $R^{c'}$; $R^2$ either represents hydrogen or a double bond; r, Ar, $R^4$, $R^5$, $R^6$, $R^7$, $R^8$, $R^c$ and $R^{c'}$ are as defined in claim 1; or a pharmaceutically acceptable salt or a stereoisomer thereof.

5. The compound according to claim 1 having the Formula Id, wherein

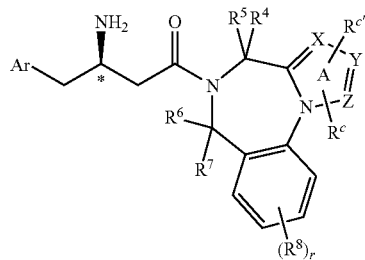

Formula Id

X, Y and Z are independently selected from the group consisting of N and —CH; the ring A is optionally substituted at any available position by one or more substituents independently selected from $R^c$ or $R^{c'}$; r, Ar, $R^4$, $R^5$, $R^6$, $R^7$, $R^8$, $R^c$ and $R^{c'}$ are as defined in claim 1; or a pharmaceutically acceptable salt or a stereoisomer thereof.

6. The compound according to claim 1 having the Formula Ie, wherein

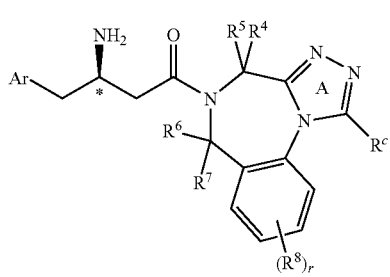

Formula Ie ring A is substituted by $R^c$; r, Ar, $R^4$, $R^5$, $R^6$, $R^7$, $R^8$ and $R^c$ are as defined in claim 1; or a pharmaceutically acceptable salt or a stereoisomer thereof.

7. The compound according to claim 1 having the Formula If, wherein

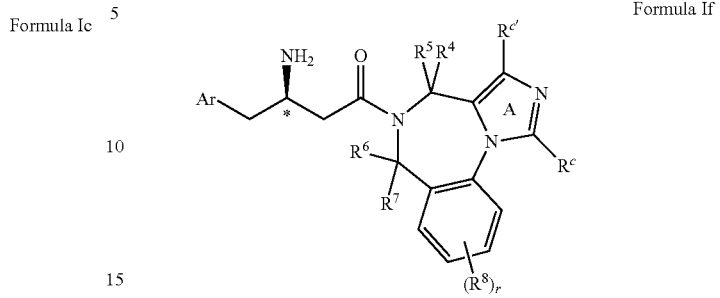

Formula If ring A is substituted by $R^c$ or $R^{c'}$; r, Ar, $R^4$, $R^5$, $R^6$, $R^7$, $R^8$, $R^c$ and $R^{c'}$ are as defined in claim 1; or pharmaceutically acceptable salt or a stereoisomer thereof.

8. The compound according to claim 1 having the Formula Ig, wherein

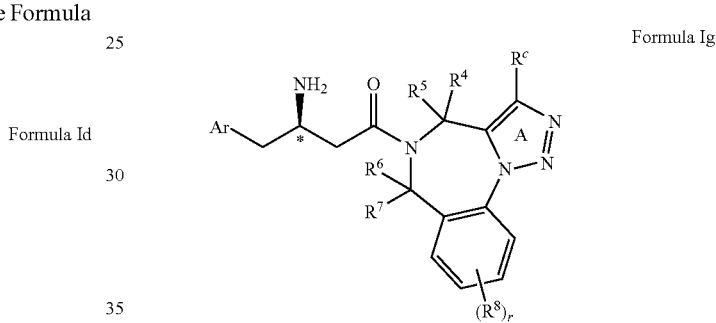

Formula Ig ring A is substituted by $R^c$; r, Ar, $R^4$, $R^5$, $R^6$, $R^7$, $R^8$ and $R^c$ are as defined in claim 1; or a pharmaceutically acceptable salt or a stereoisomer thereof.

9. The compound according to claim 1 having the Formula Ih, wherein

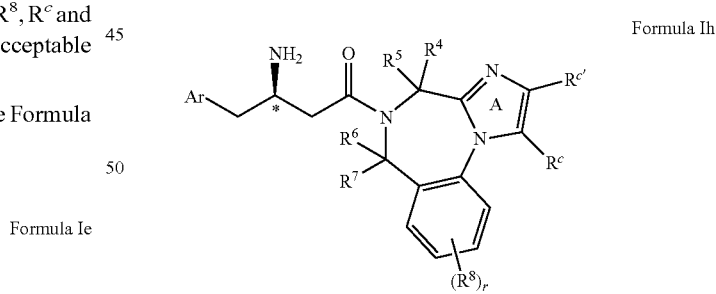

Formula Ih ring A is substituted by $R^c$ or $R^{c'}$; r, Ar, $R^4$, $R^5$, $R^6$, $R^7$, $R^8$, $R^c$ and $R^{c'}$ are as defined in claim 1; or a pharmaceutically acceptable salt or a stereoisomer thereof.

10. The compound according to claim 1, wherein Ar is selected from the group consisting of 2,4,5-trifluorophenyl, 2-fluorophenyl, 3,4-difluorophenyl and 2,5-difluorophenyl.

11. The compound according to claim 1, wherein $R^8$ is selected from the group consisting of hydrogen, fluoro, chloro and methoxy.

12. The compound according to claim 1, wherein $R^1$ is selected from the group consisting of: hydrogen, $C_{1-12}$ alkyl, $C_{2-12}$ alkenyl, $C_{2-12}$ alkynyl, $C_{1-12}$ haloalkyl, $C_{1-12}$ haloalkoxy, $C_{2-12}$ haloalkenyl, $(CH_2)_n$-aryl,
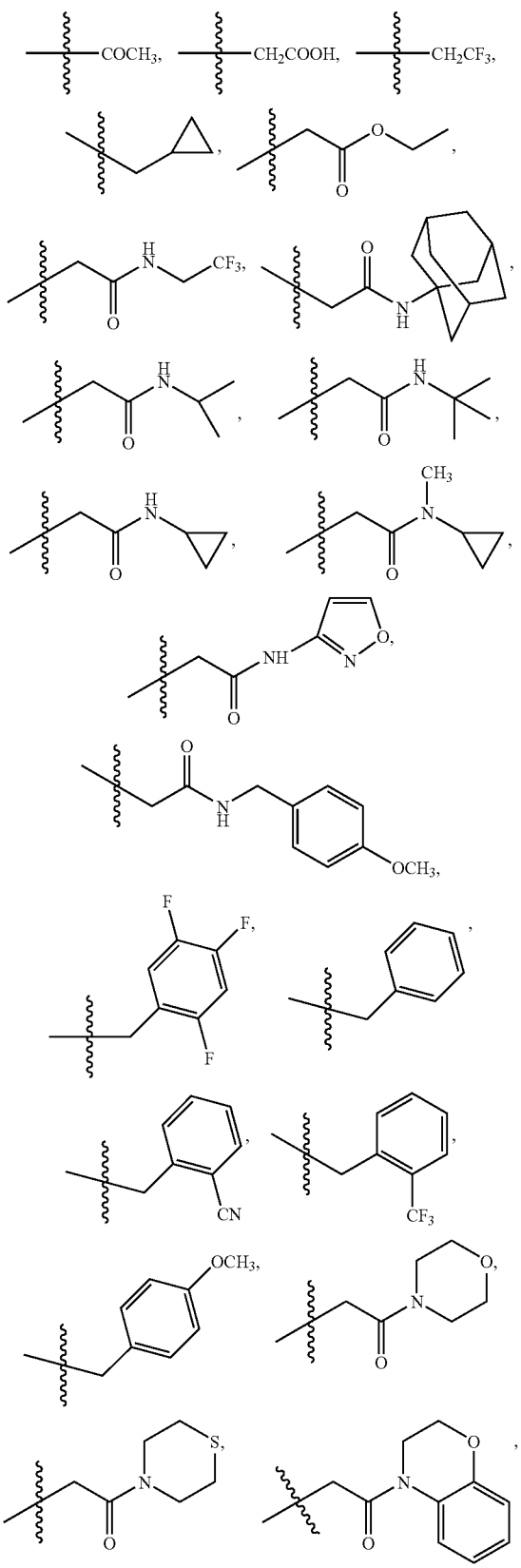
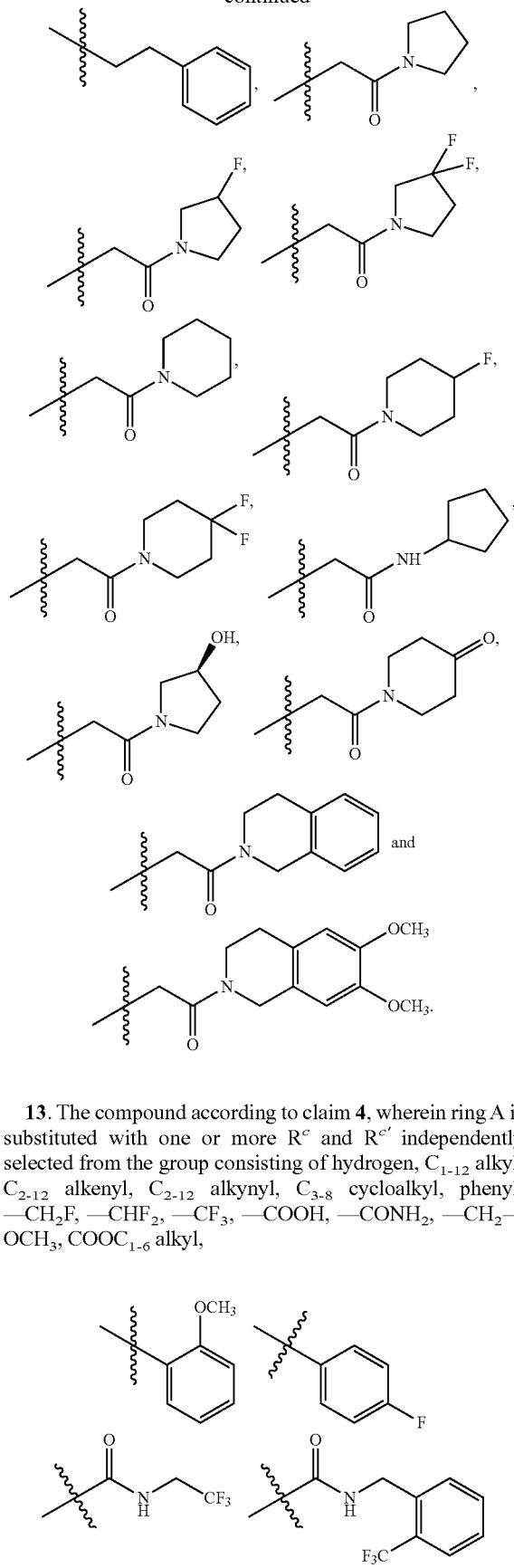
13. The compound according to claim 4, wherein ring A is substituted with one or more $R^c$ and $R^{c'}$ independently selected from the group consisting of hydrogen, $C_{1-12}$ alkyl, $C_{2-12}$ alkenyl, $C_{2-12}$ alkynyl, $C_{3-8}$ cycloalkyl, phenyl, —$CH_2F$, —$CHF_2$, —$CF_3$, —COOH, —$CONH_2$, —$CH_2$—$OCH_3$, $COOC_{1-6}$ alkyl,

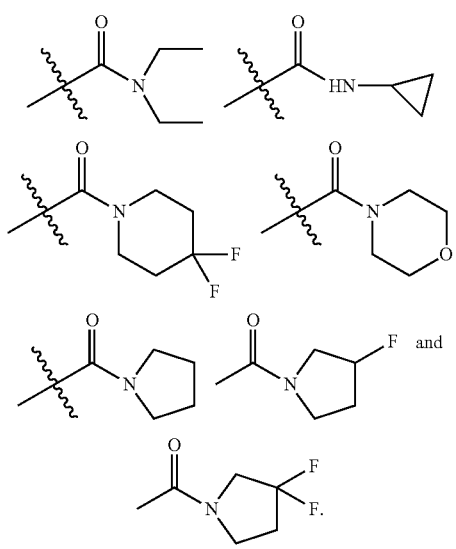
14. The compound according to claim 1, wherein $R^4$ and $R^5$ are both hydrogen.
15. The compound according to claim 1, wherein $R^6$ and $R^7$ are both hydrogen.
16. A compound which is selected from the group consisting of:
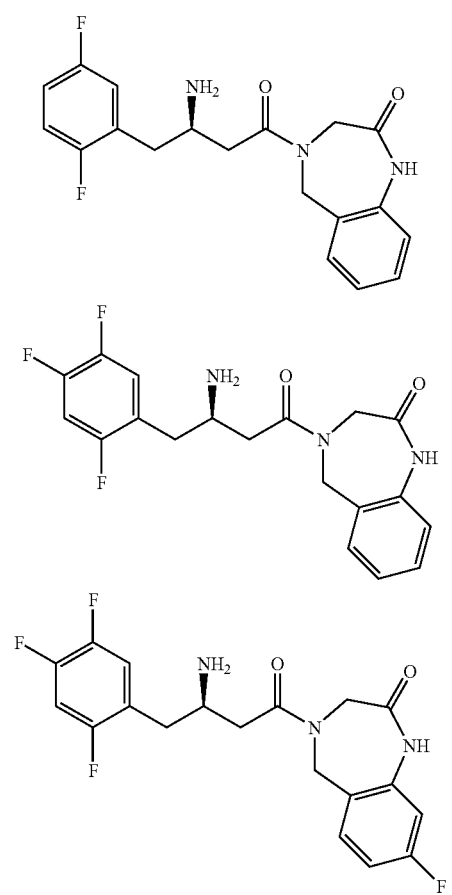
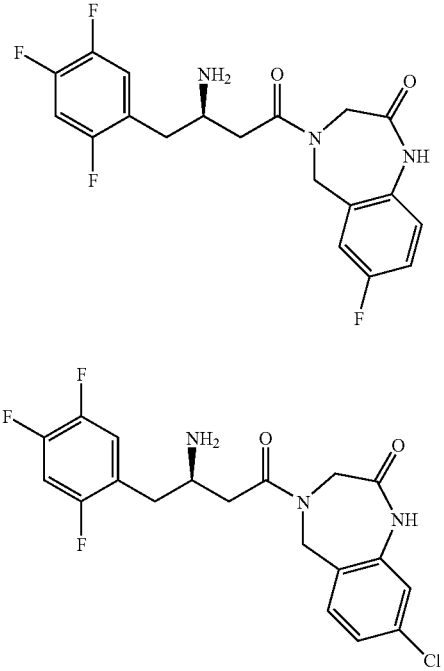
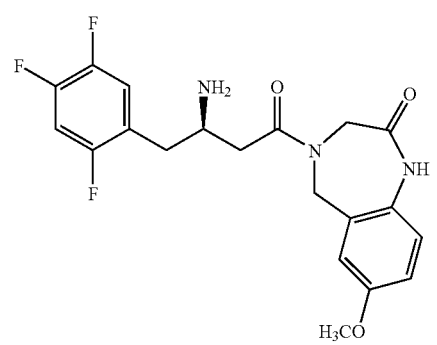
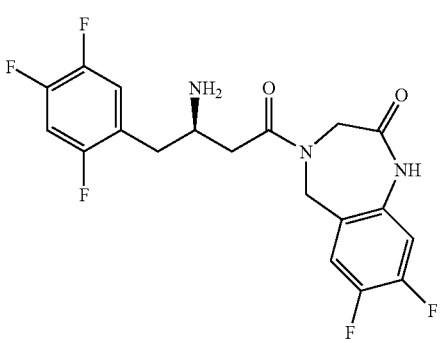
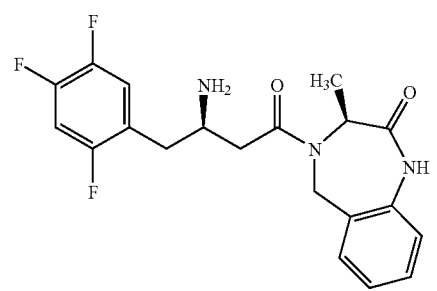

149
-continued
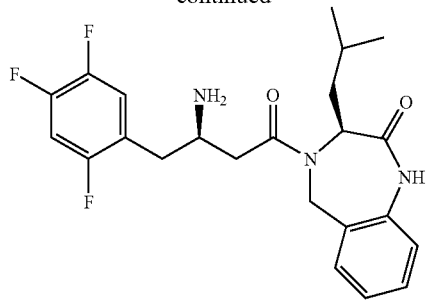
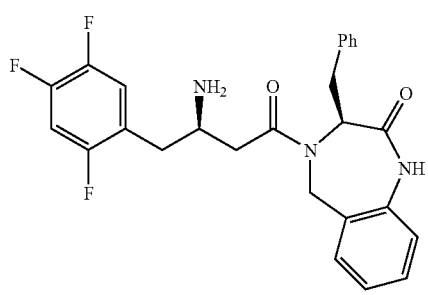
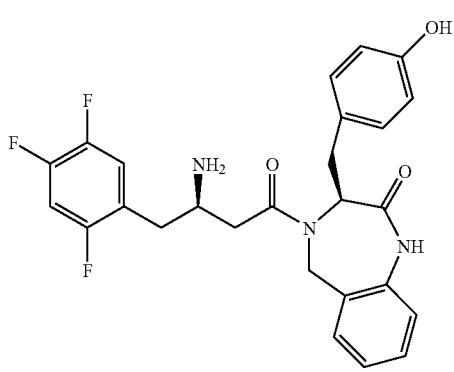
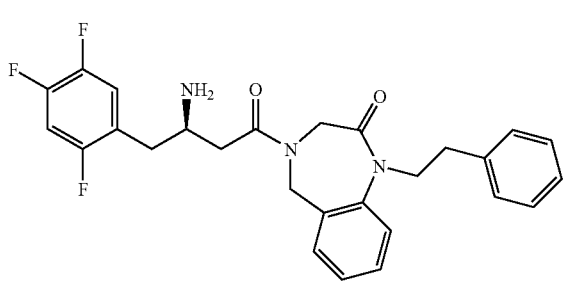
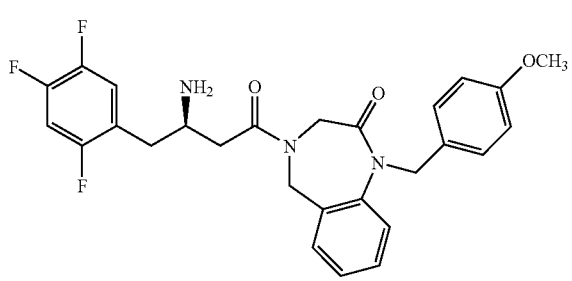
150
-continued
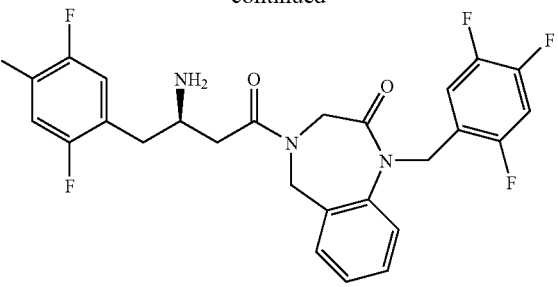
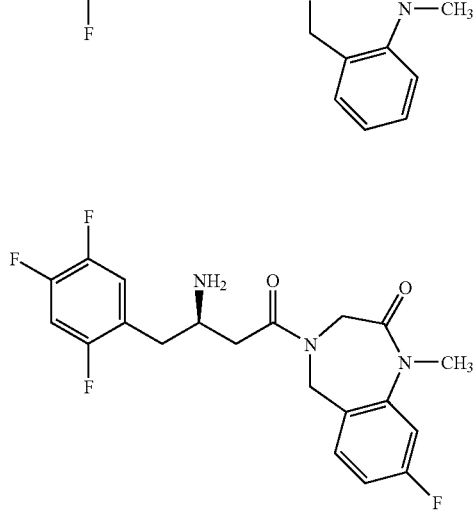
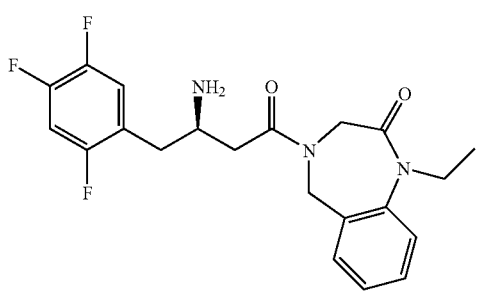
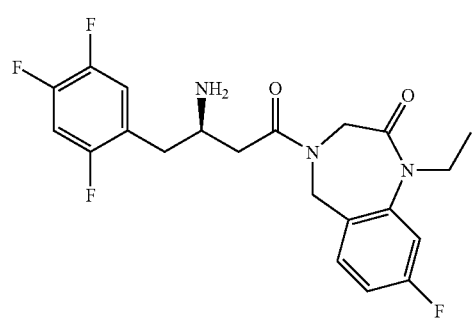

151
-continued
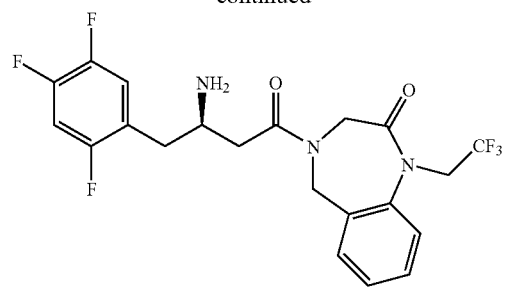
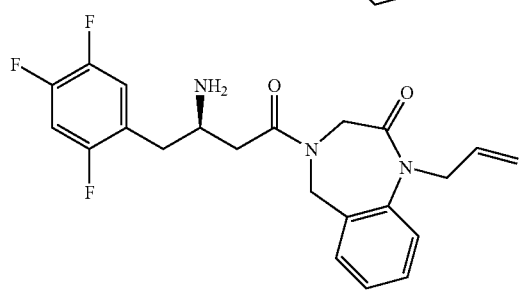
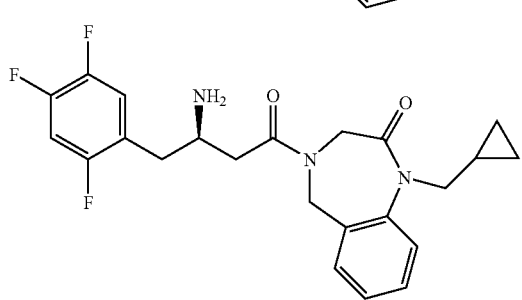
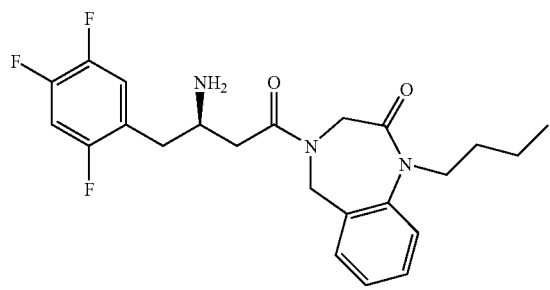
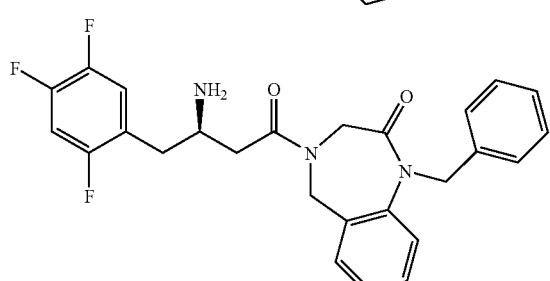
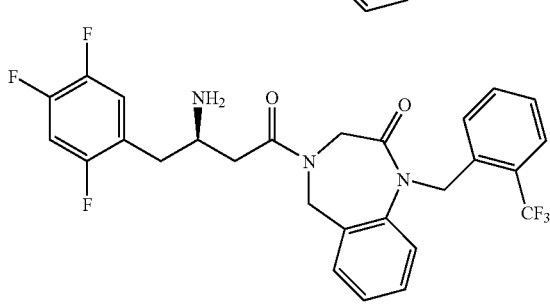
152
-continued
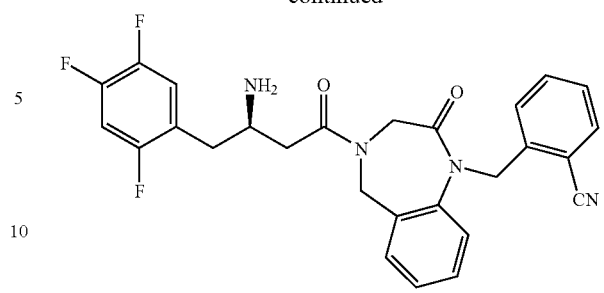
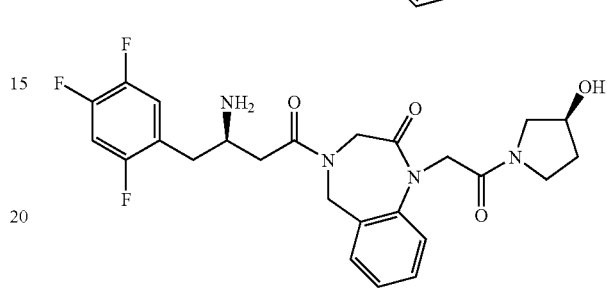
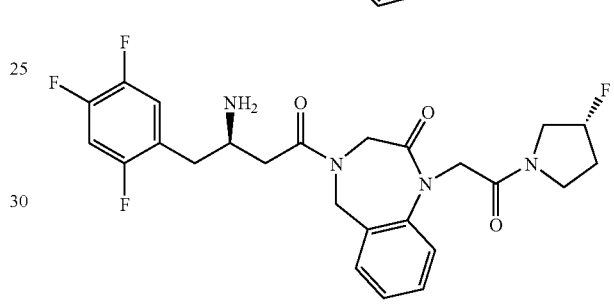
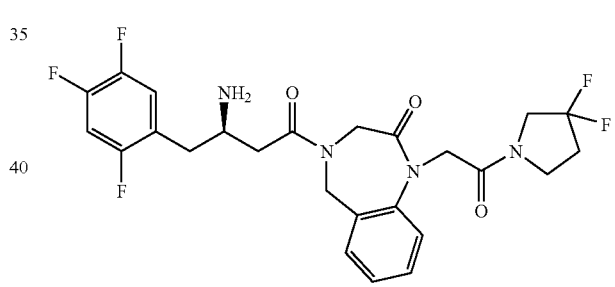
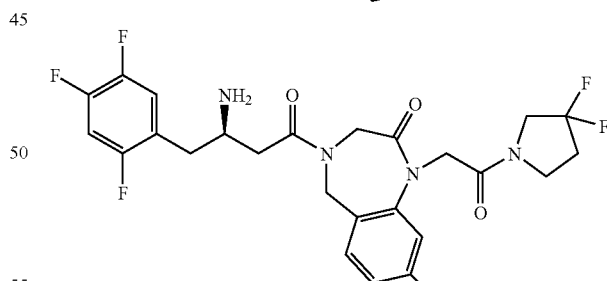
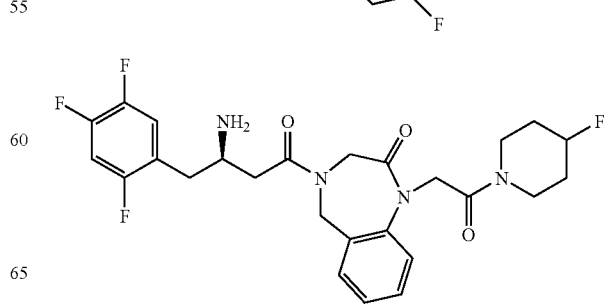

153
-continued
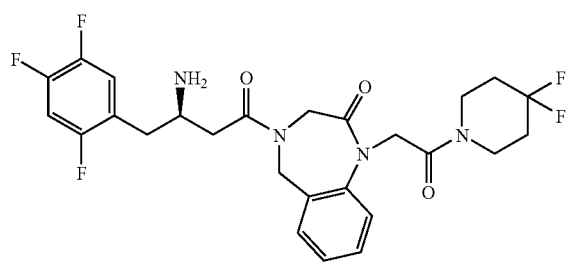
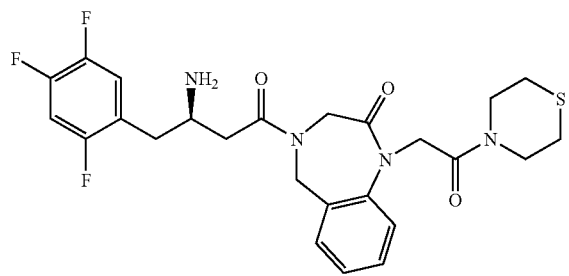
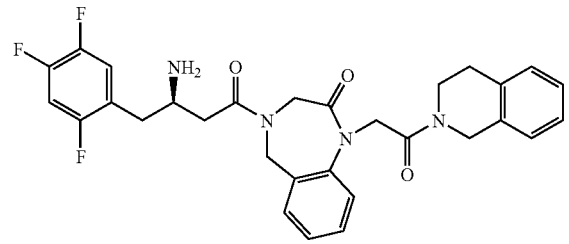
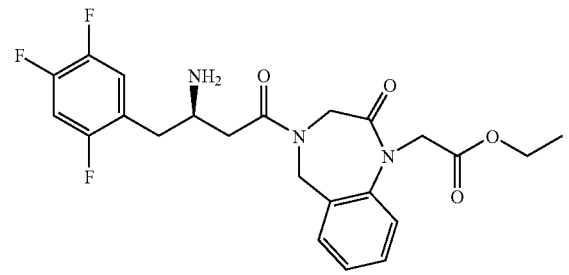
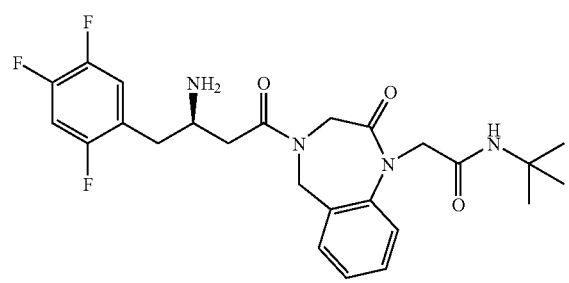
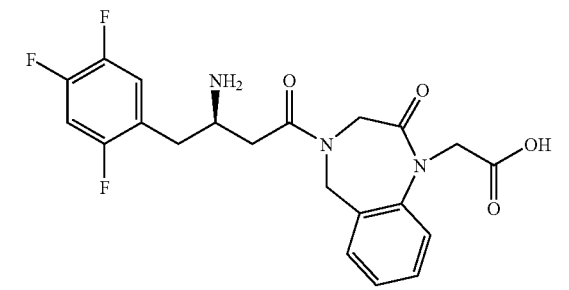
154
-continued
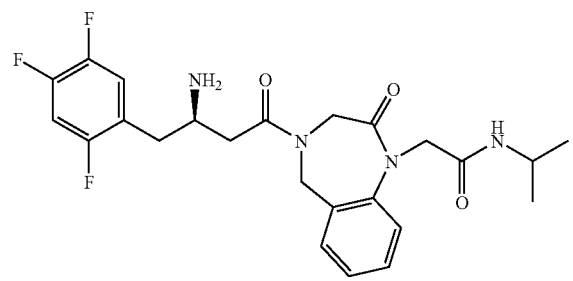
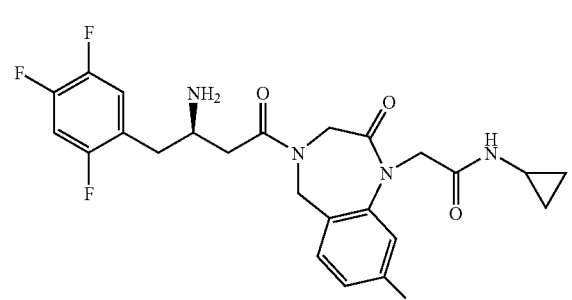
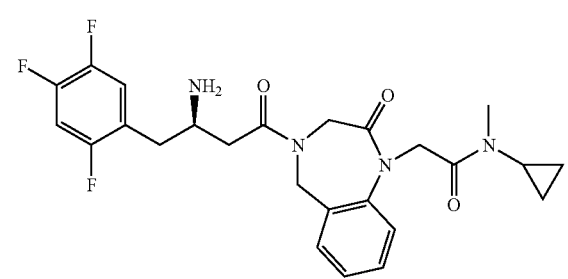
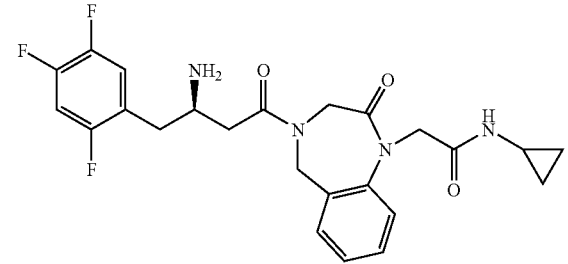
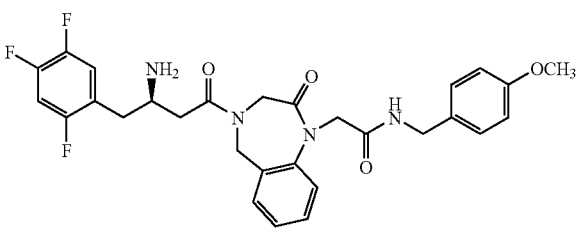
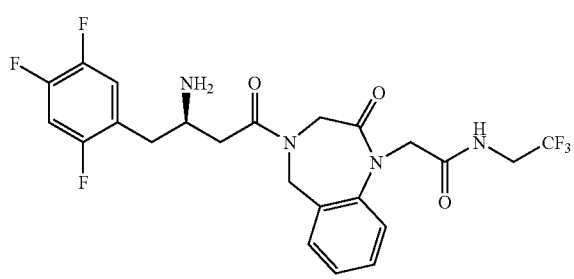

155
-continued
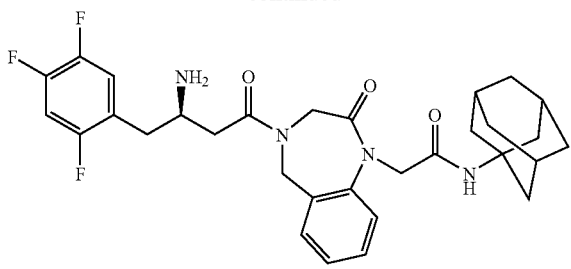
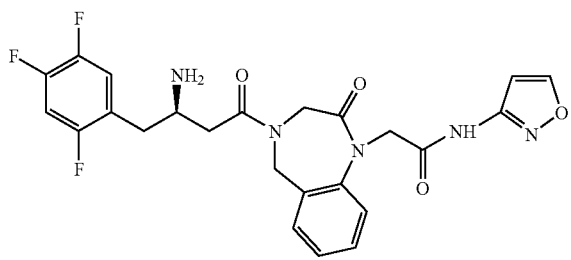
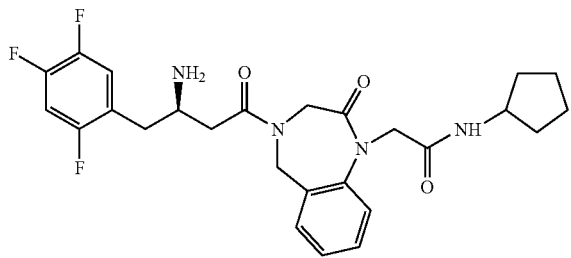
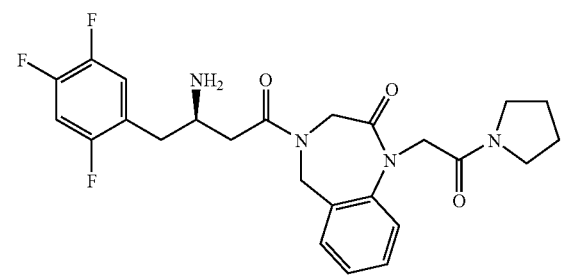
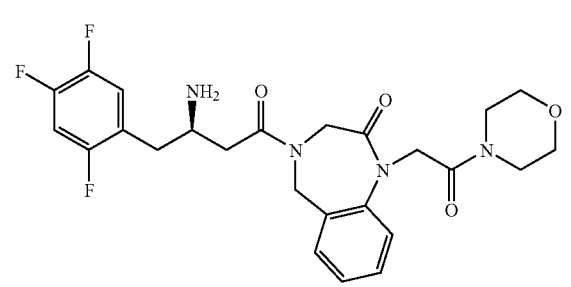
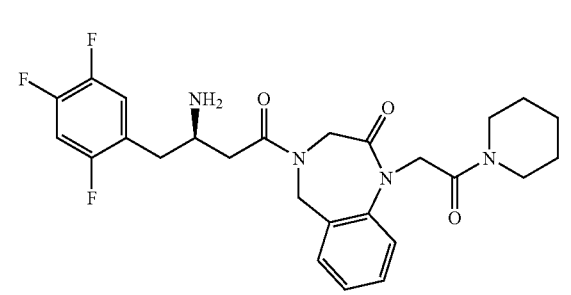
156
-continued
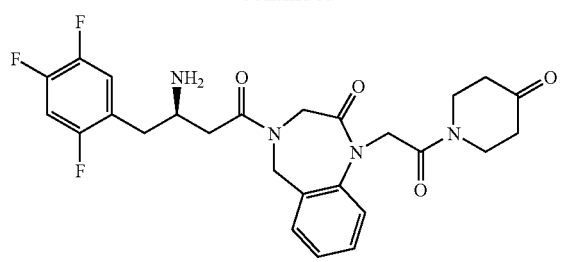
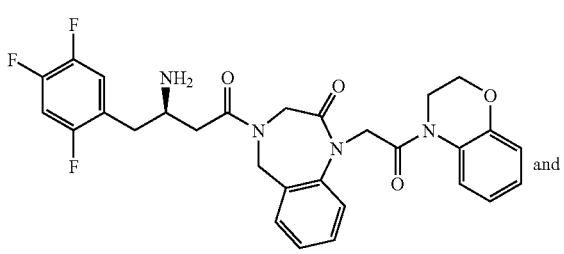
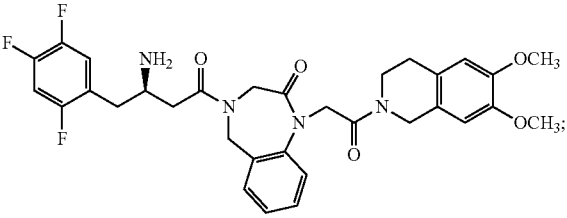 [SMILES: COc1cc2c(cc1OC)CN(C(=O)CN1C(=O)CN(C(=O)C[C@H](N)Cc3cc(F)c(F)cc3F)Cc3ccccc31)CC2]
and pharmaceutically acceptable salts thereof.
17. A compound which is selected from the group consisting of:
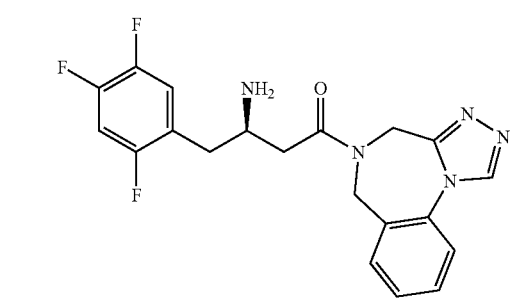
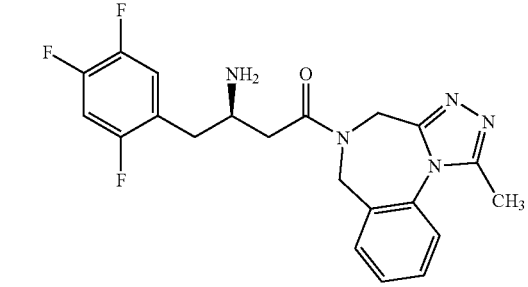

157
-continued
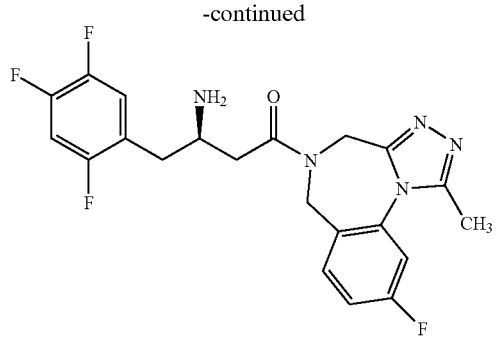
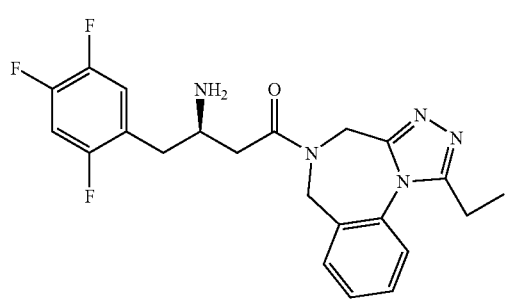
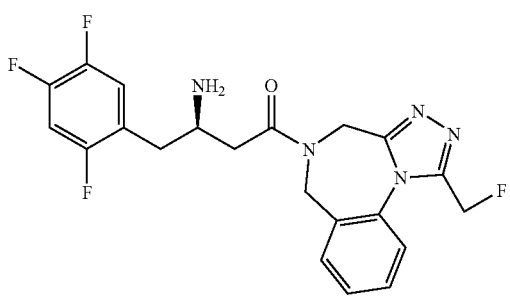
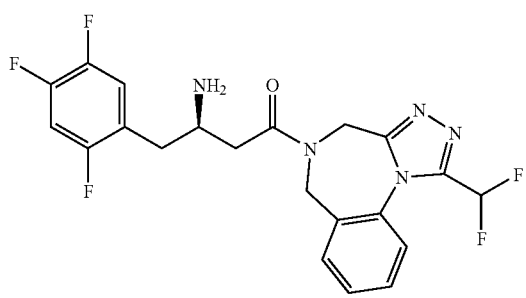
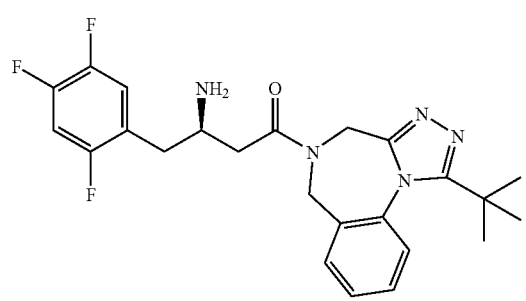
158
-continued
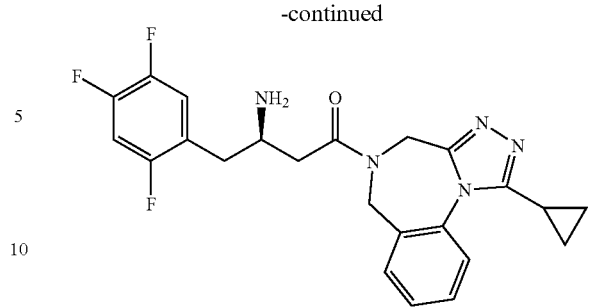
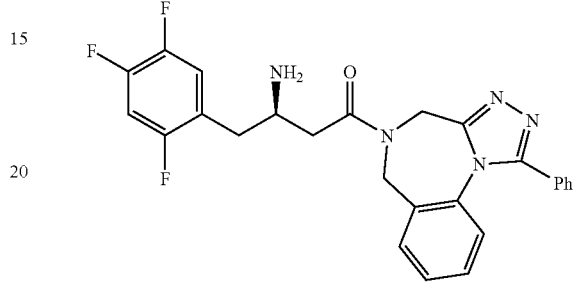
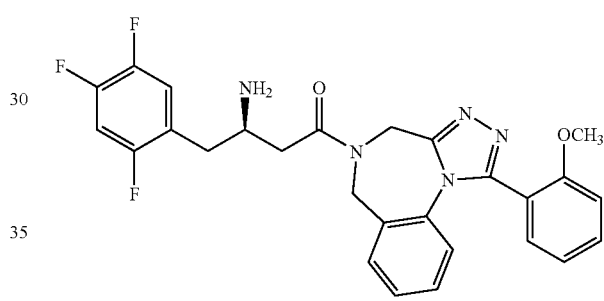
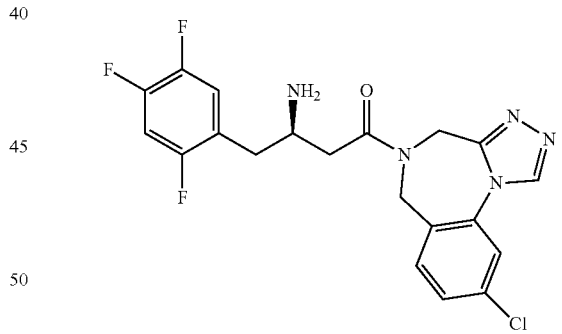
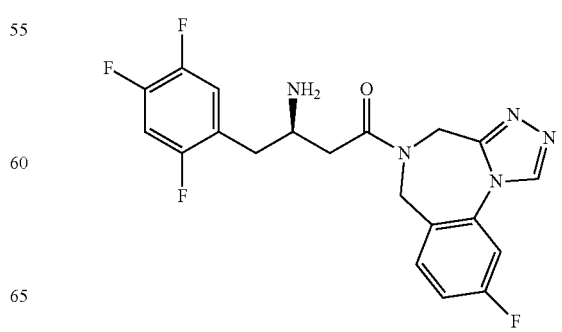

159
-continued
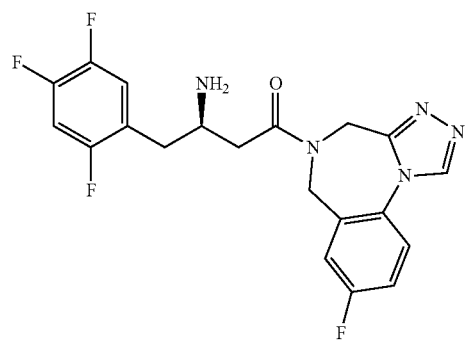
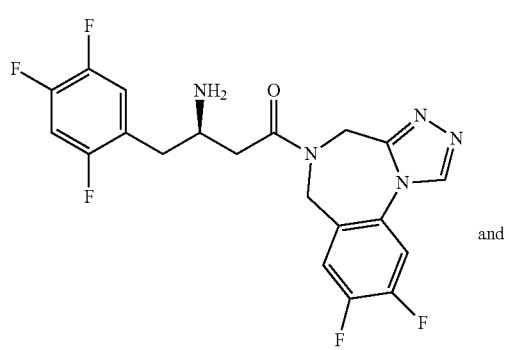
and
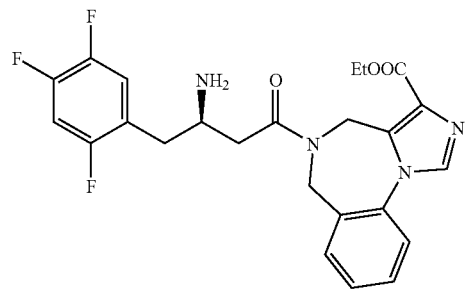
and pharmaceutically acceptable salts thereof.
18. A compound which is selected from the group consisting of:
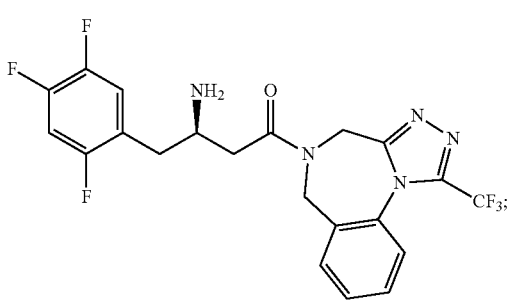
160
-continued
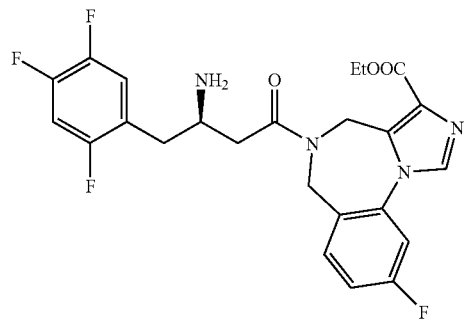
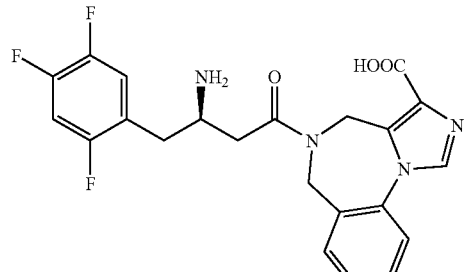
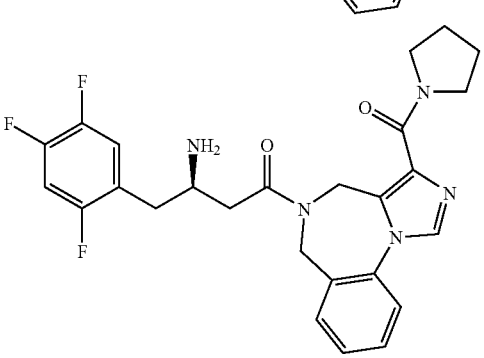
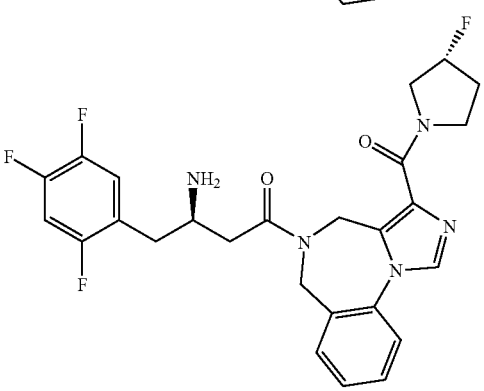
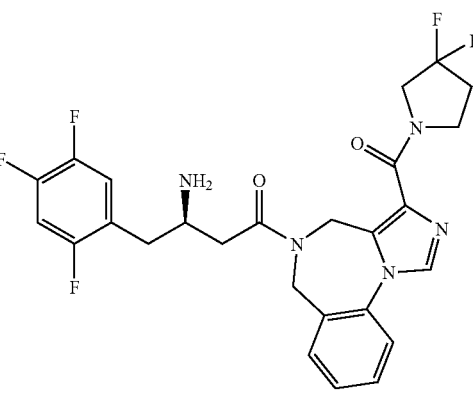

161
-continued
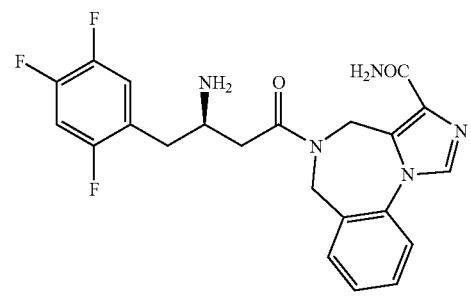
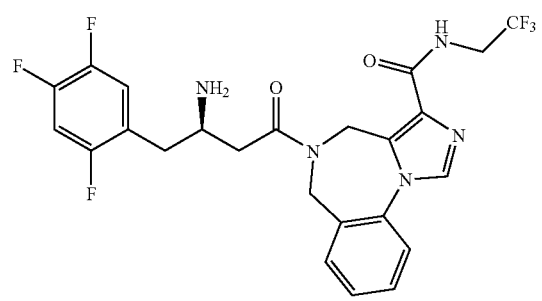
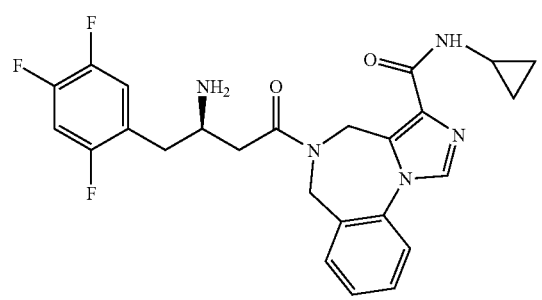
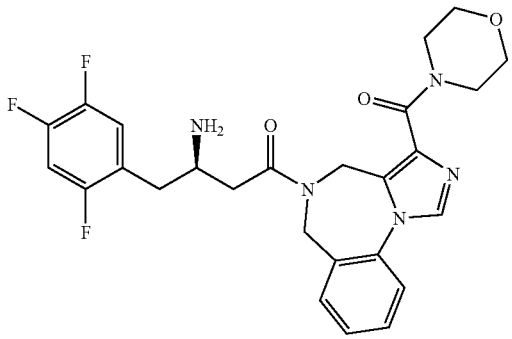
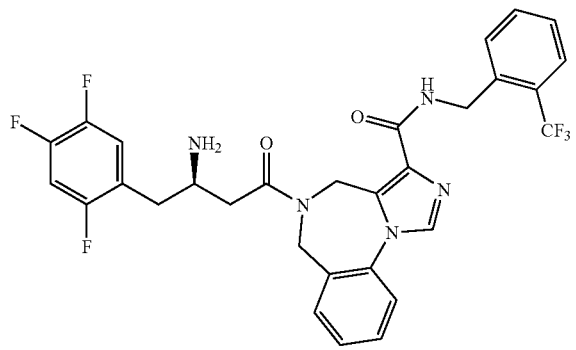
162
-continued
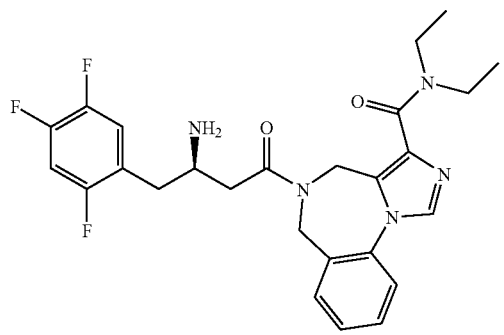
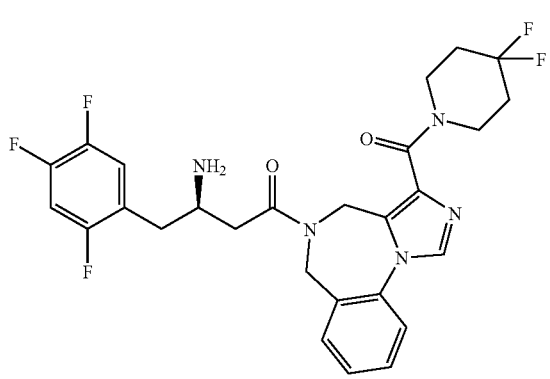
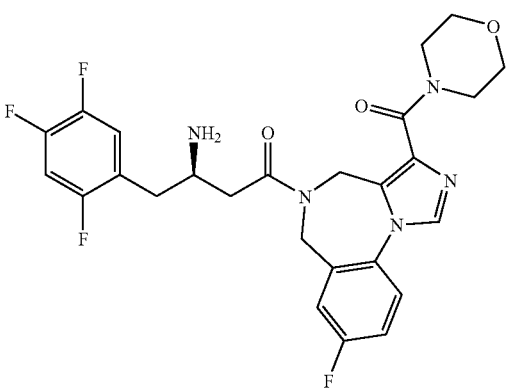
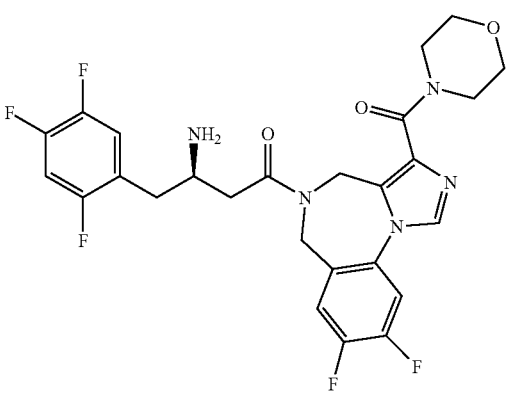

163
-continued
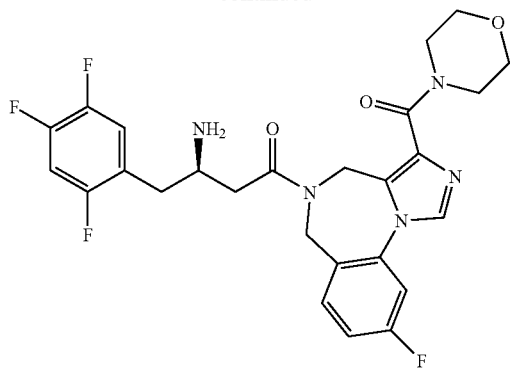
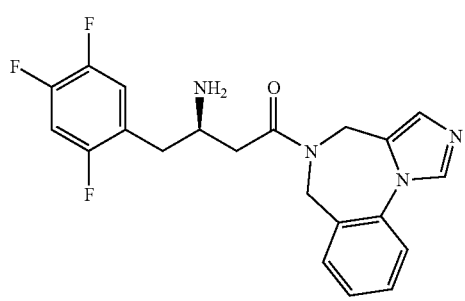
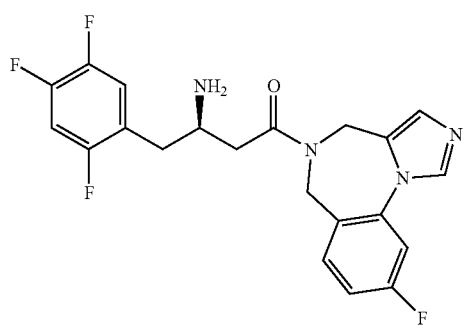
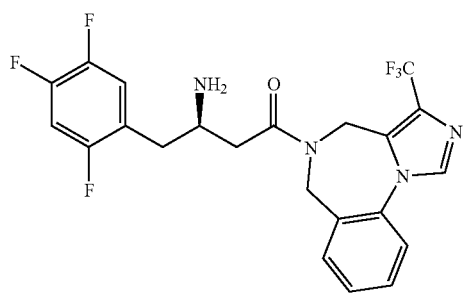
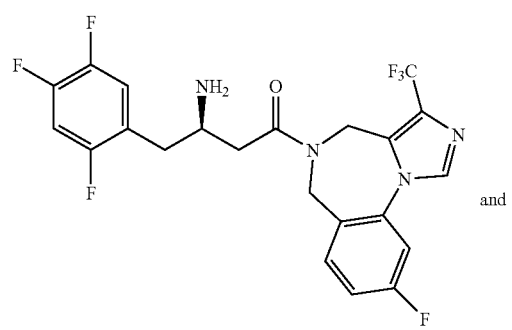
and
164
-continued
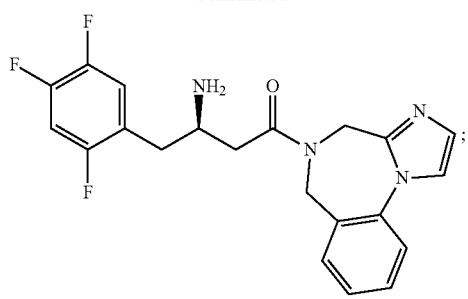 [SMILES: N[C@@H](CC(=O)N1Cc2ccccc2-n2ccnc2C1)Cc1cc(F)c(F)cc1F]
and pharmaceutically acceptable salts thereof.
19. A compound which is selected from the group consisting of:
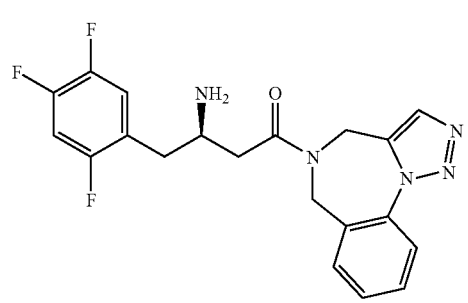
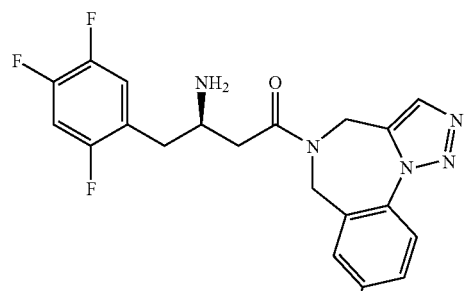
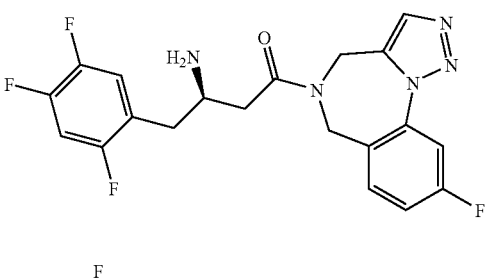
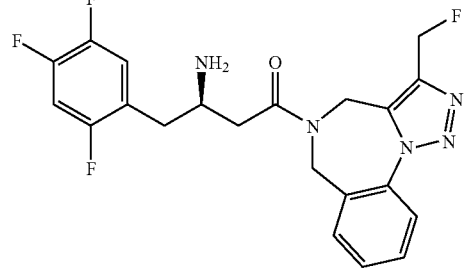

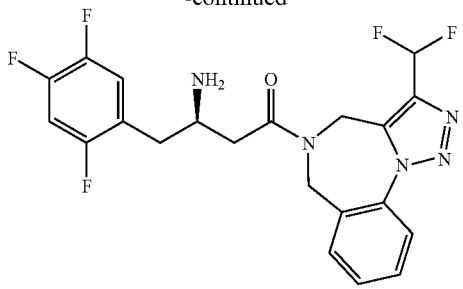

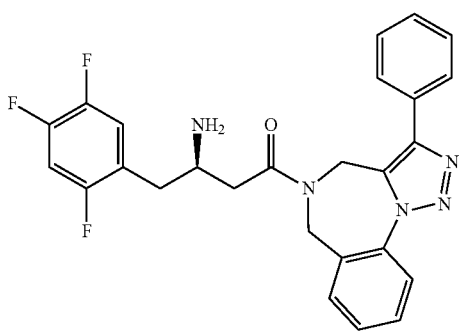

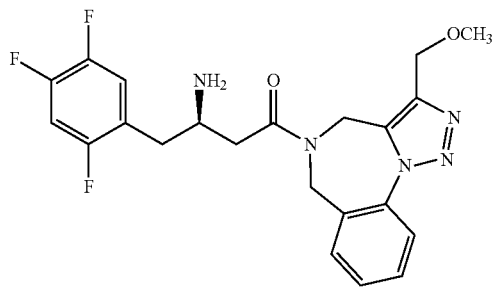

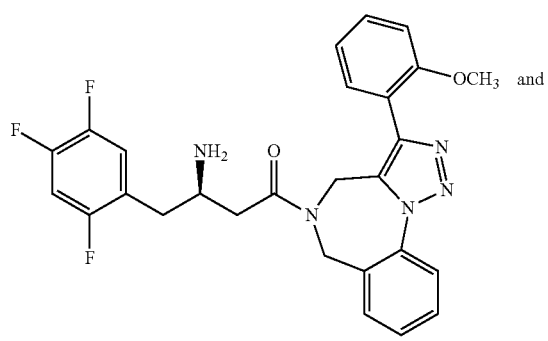

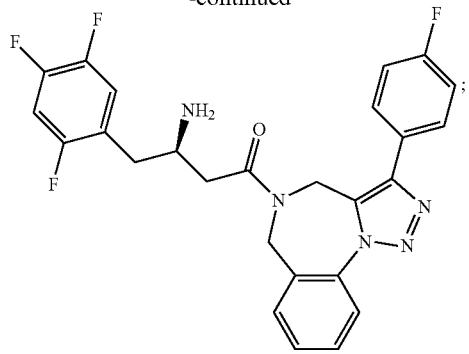

and pharmaceutically acceptable salts thereof.

20. A process for the preparation of a compound of claim 1, which comprises the following steps:

a) coupling of a compound of Formula II

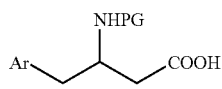

Formula II wherein PG is a protecting group, with a compound of Formula III

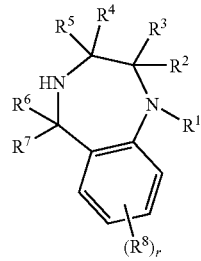

Formula III using coupling conditions;

b) removing the protecting group (PG) using deprotecting reagent;

wherein r, Ar, $R^1$, $R^2$, $R^3$, $R^4$, $R^5$, $R^6$, $R^7$, and $R^8$ are as defined in claim 1.

21. A pharmaceutical composition, comprising a compound according to claim 1, in combination with one or more pharmaceutically acceptable carriers.

22. A method for the treatment of Type 2 diabetes or Type 2 diabetes mellitus in a subject in need thereof which comprises administering a therapeutically effective amount of compound according to claim 1.

* * * * *